US008354447B2

(12) United States Patent
Markou et al.

(10) Patent No.: US 8,354,447 B2
(45) Date of Patent: Jan. 15, 2013

(54) MGLU RECEPTORS ANTAGONISTS FOR TREATING DISORDERS ASSOCIATED WITH MGLU RECEPTORS INCLUDING ADDICTION AND DEPRESSION

(75) Inventors: Athina Markou, Del Mar, CA (US); Paul Kenny, San Diego, CA (US); Neil Paterson, Encinitas, CA (US); Svetlana Semenova, Carlsbad, CA (US)

(73) Assignee: The Scripps Research Institute, La Jolla, CA (US)

( * ) Notice: Subject to any disclaimer, the term of this patent is extended or adjusted under 35 U.S.C. 154(b) by 746 days.

(21) Appl. No.: 10/527,525

(22) PCT Filed: Sep. 10, 2003

(86) PCT No.: PCT/EP03/10061
§ 371 (c)(1),
(2), (4) Date: Oct. 14, 2005

(87) PCT Pub. No.: WO2004/024150
PCT Pub. Date: Mar. 25, 2004

(65) Prior Publication Data
US 2006/0148835 A1 Jul. 6, 2006

Related U.S. Application Data

(60) Provisional application No. 60/409,867, filed on Sep. 10, 2002.

(51) Int. Cl.
*A01N 43/16* (2006.01)
*A01N 43/40* (2006.01)
*A61K 31/35* (2006.01)
*A61K 31/435* (2006.01)

(52) U.S. Cl. ...................... 514/454; 514/277
(58) Field of Classification Search .............. 514/1, 217, 514/454
See application file for complete search history.

(56) References Cited

U.S. PATENT DOCUMENTS

| 6,407,094 B1 * | 6/2002 | Adam et al. .......... 514/221 |
| 6,916,821 B2 * | 7/2005 | Bear et al. ............ 514/277 |
| 2003/0195139 A1 * | 10/2003 | Corsi et al. .......... 514/1 |

FOREIGN PATENT DOCUMENTS

WO WO 01/66113 A1 9/2001

OTHER PUBLICATIONS

Schulz, B.; Fendt, M.; Gasparini, F.; Lingenhohl, K.; Kuhn, R.; Koch, M. "The metabotropic glutamate receptor antagonist 2-methyl-6-(phenylethynyl)-pyridine (MPEP) blocks fear conditioning in rats", 2001, Neuropharmacology, 41, pp. 1-7.*
Fundytus, M.E.; Ritchie, J.; Coderre, T.J. "Attenuation of morphine withdrawal symtoms by subtype-selective metabotropic glutamate receptor antagonists", 1997, British Journal of Pharmacology, vol. 120, pp. 1015-1020.*
Chiamulera, C.; Epping-Jordan, M.P.; Zocchi, A.; Marcon, C.; Cottiny, C.; Tacconi, S.; Corsi, M.; Orzi, F.; Conquet, F. "Reinforcing and locomotor stimulant effects of cocaine are absent in mGluR5 null mutant mice", Sep. 2001, Nature Neuroscience, vol. 4(9), pp. 873-874.*
Bradley et al. "The development of an opiate withdrawal scale (OWS)", Addiction, Oct. 1987, vol. 82, No. 10, p. 1139-1142.*
Tatarczynska, et al., "Potential Anxiolytic- and Antidepressant-like Effects of MPEP, a Potent, Selective and Systemically Active mGlu5 Receptor Antagonist" *British Journal of Pharmacology* 132: 1423-1430 (2001).
Waterhouse, et al., *Society for Neuroscience Abstracts* 27, No. 2: 2358 (2001).
Ahmed, et al., "Neurobiological Evidence for Hedonic Allostasis Associated with Escalating Cocaine Use", *Nature Neuroscience* 5, No. 7: 625-626 (2002).
Harrison, et al., "Fluoxetine Combined with a Serotonin-1A Receptor Antagonist Reversed Reward Deficits Observed during Nicotine and Amphetamine Withdrawal in Rats", *Neuropsychopharmacology* 25, No. 1: 55-71 (2001).
Harrison, et al., "Nicotine Potentiation of Brain Stimulation Reward Reversed by DHβE and SCH 23390, but not by Eticlopride, LY 314582 or MPEP in Rats", *Psychopharmacology* 160: 56-66 (2002).
Cryan, et al., "Bupropion Enhances Brain Reward Function and Reverses the Affective and Somatic Aspects of Nicotine Withdrawal in the Rat", *Psychopharmacology* 168: 347-358 (2003).
Shigemoto, et al., "Differential Presynaptic Localization of Metabotropic Glutamate Receptor Subtypes in the Rat Hippocampus", *The Journal of Neuroscience* 17, No. 19: 7503-7522 (1997).

* cited by examiner

*Primary Examiner* — Sreeni Padmanabhan
*Assistant Examiner* — Kendra D Carter
(74) *Attorney, Agent, or Firm* — Hugh Wang; Thomas Fitting; Lisa A. Haile

(57) ABSTRACT

Methods are provided for treating disorders associated with mGlu receptors by simultaneously inhibiting at least two mGluRs belonging to at least two different groups. In one embodiment, there are provided methods for treating a disorder associated with mGlu receptors 2, 3, and 5, including administering to a subject in need thereof an effective amount of at least one antagonist which modulates mGluR2, mGluR3, and mGluR5. The disorders treated by the method include, for example, nicotine addiction, cocaine addiction, and depression.

10 Claims, 25 Drawing Sheets a b p-MPPI + PAROXETINE

MGLU RECEPTORS ANTAGONISTS FOR TREATING DISORDERS ASSOCIATED WITH MGLU RECEPTORS INCLUDING ADDICTION AND DEPRESSION

CROSS REFERENCE TO RELATED APPLICATIONS

This application claims the benefit of priority under 35 USC §365(c) of International Application No. PCT/EP2003/010061, with an international filing date of Sep. 10, 2003, which claims priority to U.S. Application No. 60/409,867 filed Sep. 10, 2002, which are incorporated herein by reference in their entirety.

STATEMENT OF GOVERNMENT SUPPORT

This invention was made in part by grant number DA 11946 from the National Institute on Drug Abuse. The U.S. Government therefore has certain rights in the invention.

FIELD OF THE INVENTION

The present invention relates generally to methods for treating disorders associated with metabotropic glutamate receptors, and more specifically to methods for treating disorders associated with metabotropic glutamate receptors 2, 3, and 5.

BACKGROUND INFORMATION

Glutamate receptors play a role in numerous neurological, neurodegenerative, psychiatric, and psychological disorders, and a variety of mammalian disease states are associated with aberrant activity of these receptors. Glutamate receptors have been classified as either "ionotropic" or "metabotropic". Ionotropic receptors are directly coupled to the opening of cation channels in the cell membranes of the neuron. Metabotropic receptors belong to the family of G-protein-coupled receptors and are coupled to systems that lead to enhanced phosphoinositide hydrolysis, activation of phospholipase D, increases or decreases in cAMP formation, and changes in ion channel function.

Metabotropic glutamate receptors (mGluRs) are divided into three groups based on amino acid sequence homology, transduction mechanism and binding selectivity: Group I, Group II and Group III. Group I includes metabotropic glutamate receptors 1 and 5 (mGluR1 and mGluR5), Group II includes metabotropic glutamate receptors 2 and 3 (mGluR2 and mGluR3), and Group III includes metabotropic glutamate receptors 4, 6, 7, and 8 (mGluR4, mGluR6, mGluR7 and mGluR8). Each mGluR type may be found in several subtypes. For example, subtypes of mGluR1 include mGluR1a, mGluR1b and mGluR1c.

It is only recently that researchers have begun to elucidate physiological roles for each mGluR group. For example, Group II metabotropic glutamate receptors (mGluII), including mGlu2 and mGlu3 receptors, are inhibitory autoreceptors located primarily on glutamatergic afferents throughout the mammalian brain where they decrease excitatory glutamate transmission (Cartmell and Schoepp, J Neurochem 75:889-907, 2000). $GABA_B$ receptors, which share close structural and functional homology to mGluII receptors (Schoepp, *J. Pharmacol. Exp. Ther.*, 299:12-20, 2001), also negatively regulate glutamate transmission. Recently, activation of mGluII and $GABA_B$ receptors was shown to decrease excitatory glutamate transmission in the ventral tegmental area (VTA) and nucleus accumbens (NAcc) (Bonci et al., *Eur. J. Neurosci.*, 9:2359-2369, 1997; Xi et al., *J. Pharmacol. Exp. Ther.*, 300:162-171, 2002; Erhardt et al., Naunyn Schmiedebergs *Arch. Pharmacol.*, 365:173-180, 2002), suggesting that these receptors may regulate the activity of the brain's reward circuitry. Accordingly, LY314582 and CGP44532, agonists at mGluII and $GABA_B$ receptors respectively, were shown to elevate intracranial self-stimulation (ICSS) reward thresholds in drug-naïve rats (Macey et al., *Neuropharmacology*, 40:676-685, 2001; Harrison et al., *Psychopharmacology*, 160:56-66, 2002), demonstrating that mGluII and $GABA_B$ receptors negatively regulate brain reward function.

Moreover, there is accumulating evidence that the function of mGluII and $GABA_B$ receptors increases during the development of drug dependence. For example, prolonged morphine, cocaine or amphetamine treatment increased inhibitory regulation of glutamate transmission by mGluII and $GABA_B$ receptors located in the VTA and NAcc (Manzoni and Williams, *J. Neurosci.*, 19:6629-6636, 1999; Xi et al., *Soc. Neurosci., Abstr* 27: 2596, 2001; Giorgetti et al., *Neuroscience*, 109:585-595, 2002).

Attempts at elucidating the physiological roles of Group I mGluRs suggest that activation of these receptors elicits neuronal excitation. Evidence indicates that this excitation is due to direct activation of postsynaptic mGluRs, but it also has been suggested that activation of presynaptic mGluRs occurs, resulting in increased neurotransmitter release (Baskys, *Trends Pharmacol. Sci.* 15:92, 1992, Schoepp, *Neurochem. Int.* 24:439, 1994, Pin et al., *Neuropharmacology* 34:1, 1995.) Thus, it has been proposed that antagonists for the Group I mGluRs may be useful in treating neurological disorders such as senile dementia, Parkinson's disease, Alzheimer's disease, Huntington's Chorea, pain, epilepsy, and head trauma.

However, less is known about the potential therapeutic benefits that may be realized as a result of simultaneous antagonism of mGluRs belonging to different groups. Furthermore, little is known about whether antagonists of mGluRs are useful for treating disorders such as substance abuse and depression. The invention addresses these issues and further provides related advantages.

SUMMARY OF THE INVENTION

The present invention provides methods for treating disorders associated with metabotropic glutamate receptors (mGluRs) by simultaneously inhibiting at least two mGluRs belonging to at least two different groups. In one embodiment, there are provided methods for treating a metabotropic glutamate disorder, including administering to a subject in need thereof an effective amount of at least one antagonist which modulates mGluR2, mGluR3, and mGluR5.

In another embodiment, the present invention provides methods for treating a metabotropic glutamate disorder including administering to a subject in need thereof an effective amount of at least one antagonist which modulates mGluR2 and mGluR5, thereby treating the disorder.

In still another embodiment, the present invention provides methods for treating a metabotropic glutamate disorder, including administering to a subject in need thereof an effective amount of at least one antagonist which modulates mGluR3 and mGluR5, thereby treating the disorder.

In still another embodiment, the present invention provides methods for treating substance abuse. In one aspect, a method according to this embodiment includes administering to a subject in need thereof an effective amount of at least one antagonist which modulates mGluR2, mGluR3, and mGluR5, wherein the effective amount is sufficient to diminish, inhibit or eliminate desire for said substance in said subject.

In still another embodiment, the present invention provides methods for treating depression, including administering to a subject in need thereof an effective amount of at least one antagonist which modulates mGluR2, mGluR3 and/or mGluR5, thereby treating the depression. The depression can be either drug-induced or non-drug induced depression.

In another embodiment, the present invention provides a method of screening for an agent that improves the ability of an mGluR2, mGluR3, and/or mGluR5 antagonist to at least partially normalize a deficit in brain reward function reflected in intracranial self-stimulation (ICSS) threshold of a non-human mammalian subject. The method includes:
 a) affecting the ICSS threshold of the subject;
 b) administering to the subject, a sufficient amount of the known inhibitor to at least partially normalize the ICSS threshold when administered alone or in combination with another inhibitor, wherein the known inhibitor is an antagonist of at least one of mGluR2, mGluR3, and mGluR5;
 b) administering to the non-human mammalian subject, an effective amount of a test agent, wherein the test agent is a known or suspected antagonist of at least one of mGluR2, mGluR3, and mGluR5; and
 c) determining whether the test agent improves the ability of the known inhibitor to at least partially normalize the ICSS threshold, thereby identifying an agent that improves the ability of the known inhibitor to at least partially normalize ICSS threshold.

In one aspect, the method includes administering an mGluR2 and/or mGluR3 inhibitor, such as LY341495, simultaneously with a test agent that is known or suspected to be an antagonist of mGluR5. In another aspect, the method includes administering an mGluR5 inhibitor, such as MPEP, simultaneously with a test agent that is know or suspected to be an antagonist of mGluR2 and/or mGluR3.

BRIEF DESCRIPTION OF THE FIGURES

FIG. 2A, Data are expressed as mean (±SEM) percentage change from baseline threshold. FIG. 2B, Data are expressed as mean (±SEM) percentage change from baseline response latency. **P<0.01, different from nicotine-treated rats after vehicle injection. ##P<0.01, different from control rats after injection with same dose of LY314582.

FIG. 3A, Data are expressed as mean (±SEM) percentage change from baseline threshold. FIG. 3B, Data are expressed as mean (±SEM) percentage change from baseline response latency. ***P<0.001, different from nicotine-treated rats after vehicle injection. ##P<0.01, #p<0.05, different from control rats after injection with same dose of LY314582.

FIG. 4A, Data are expressed as mean (±SEM) percentage change from baseline threshold in rats undergoing nicotine withdrawal. FIG. 4B, Data are expressed as mean (±SEM) percentage change from baseline threshold in control rats. ICSS thresholds and response latencies were tested 12, 18, 24, 36, 48 and 72 h after surgical removal of osmotic mini-pumps delivering nicotine (FIG. 3A) or vehicle (FIG. 3B). Rats received a single injection of LY341495 (1 mg/kg) or vehicle 30 min before the 18 h time-point (indicated by black arrow). ***P<0.001, different from rats undergoing nicotine withdrawal treated with vehicle 30 min before the 18 h time-point.

FIG. 9A shows development of escalation In cocaine Intake In the LgA rats; data are express as raw values. FIG. 9B shows the effects of MPEP In ShA and LgA rats as percent of baseline responding (mean±SEM). Panel C Indicates the effects of MPEP on cocaine self-administration (data expressed as percent of baseline responding (mean+SEM) with ShA and LgA rats combined). Asterisks indicate significant differences from control conditions for each reinforcer (*P<0.05, **P<0.01).

FIGS. 20A-20C depict thresholds of saline-exposed subjects treated acutely with the various treatments; for clarity the same saline-exposed vehicle-treated control group is presented in each panel. FIGS. 20D-20F depict thresholds of amphetamine-exposed subjects; the same amphetamine-exposed vehicle-treated group is presented in each figure. The arrow indicates the time-point at which the acute drug treatment was administered. Asterisks (*) denote statistically significant differences between the drug combination- and saline-treated groups (p<0.05) (triangles). Hashes (#) denote significant differences from the saline-exposed vehicle-treated rats (p<0.05) (squares).

FIG. 22B (p-MPPI (3 mg/kg) treatment), n=10, FIG. 22C (Paroxetine (1.25 mg/kg) treatment), n=10; and FIG. 22D [p-MPPI (3 mg/kg) and paroxetine (1.25 mg/kg) treatment], n=12.

As illustrated in FIG. 26A, in saline pretreated animals, bupropion treatment resulted in a lowering of brain reward thresholds at all doses (10 mg/kg, n=8; 20 mg/kg, n=8; 40 mg/kg, n=10) compared with vehicle-treated subjects (n=12). This threshold lowering was short lived as all animals returned to baseline thresholds at the next testing point that was 6 h later. All nicotine-pretreated animals exhibited elevated thresholds 12 h following withdrawal. Bupropion treatment before the 18-h time point resulted in a lowering of brain reward thresholds at all doses tested (10 mg/kg, n=9; 20 mg/kg, n=9; 40 mg/kg, n=9) compared with vehicle-treated subjects that were exposed to nicotine (n=11). This reversal of threshold elevations was significantly prolonged in animals treated with the higher bupropion dose (40 mg/kg) that were previously treated with nicotine; these animals exhibited thresholds significantly lower than saline-treated nicotine withdrawing subjects at the 24-h withdrawal time point (6.5 h post-bupropion administration). All data points represent mean values with vertical lines indicating 1 SEM. * indicates groups that differed significantly from corresponding vehicle treated animals; $P<0.05$. # indicates groups that differed significantly from relevant chronic saline-pretreated controls; $P<0.05$. Open squares indicate vehicle; Up arrows indicate 10 mg/kg bupropion; Down arrows indicate 20 mg/kg bupropion; Circles represent 40 mg/kg bupropion. FIG. 26B illustrates that the area under the curve analysis also shows that animals pretreated with nicotine had elevated brain reward thresholds after termination of nicotine administration. (i.e., withdrawal). Furthermore, this analysis clearly demonstrates that acute treatment with bupropion (40 mg/kg) reversed this elevation in thresholds. All bars represent mean values with vertical lines indicating 1 SEM. * indicates groups that differed significantly from corresponding vehicle-treated animals; $P<0.05$. # indicates groups that differed significantly from relevant chronic saline pretreated controls; $P<0.05$. Open bar is Vehicle; upper left to lower right lined bar is 10 mg/kg; lower left to upper right lined bar is 20 mg/kg; cross-hatched bar is 40 mg/kg.

As illustrated in FIG. 27A, six hours following withdrawal from chronic nicotine administration, there was a significant increase in the amount of total somatic signs of abstinence. Bupropion treatment 30 min prior to the 12-h withdrawal time point resulted in a reversal of the expression of somatic signs (5 mg/kg, n=8; 10 mg/kg, n=7; 20 mg/kg, n=7; 40 mg/kg, n=8) compared with vehicle treatment (n=6). FIG. 27B illustrates the effects of bupropion on the individual clusters of signs of withdrawal 12 h following minipump removal. All bars represent mean values with vertical lines indicating 1 SEM. * indicates groups that differed significantly from vehicle-treated animals; $P<0.05$. # indicates groups that differed significantly from baseline (6 h following initiation of withdrawal) level; $P<0.05$. Open bars represent Vehicle; horizontal bars represent 5 mg/kg bupropion; upper left to lower right lined bars represent 10 mg/kg; lower left to upper right lined bars represent 20 mg/kg; cross-hatched bars represent 40 mg/kg.

DETAILED DESCRIPTION OF THE INVENTION

Figure 1:
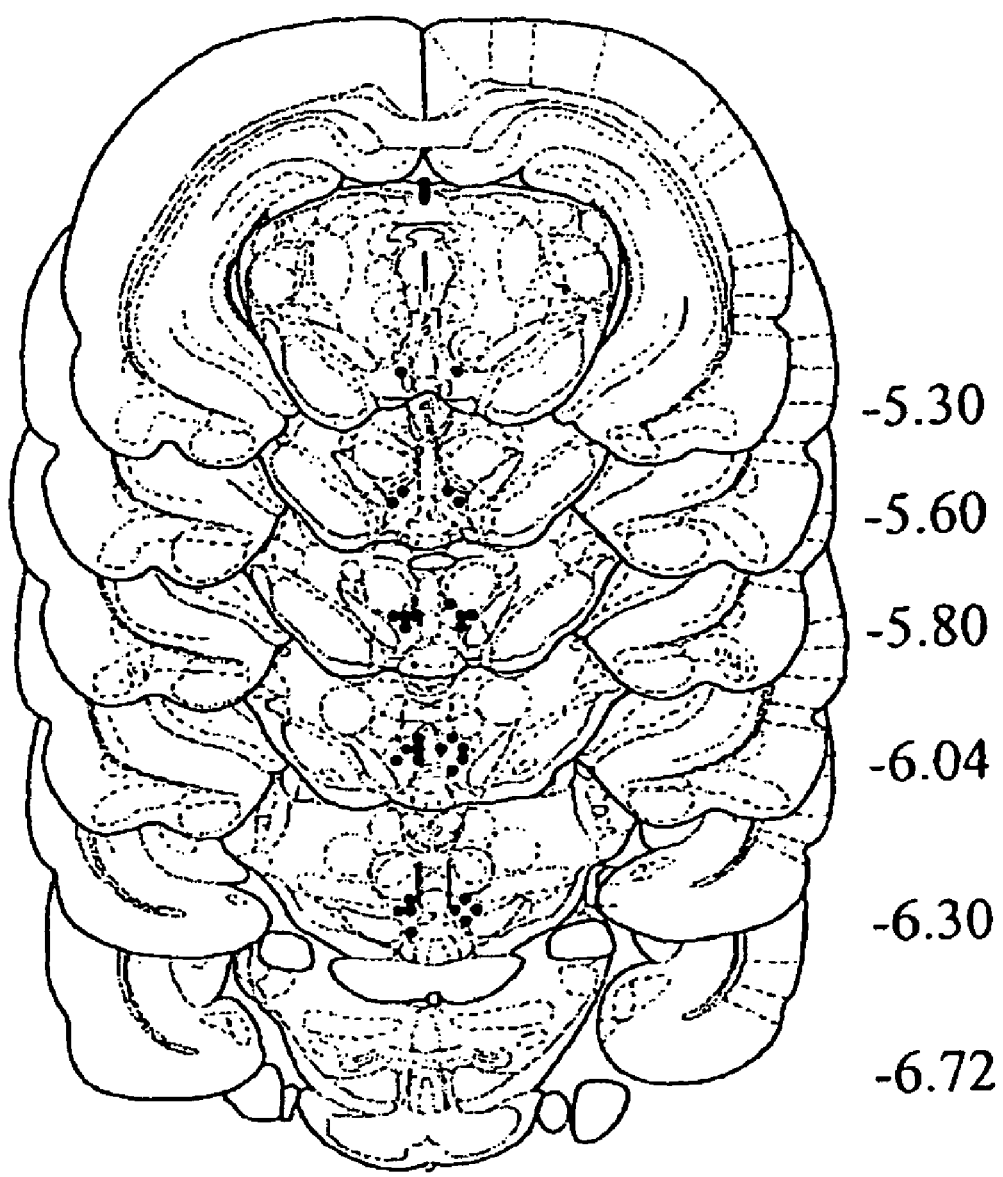
FIG. 1 is a diagrammatic representation of coronal sections from the rat brain showing histological reconstruction of the injection sites in the ventral tegmental area (5.30-6.72 mm posterior to bregma, according to the atlas of Paxinos and Watson, 1986). Black circles indicate locations of injection tips located inside the VTA and included in statistical analysis. Data from rats with injection sites located outside the VTA were removed from the analyses.

The present invention is based on the following findings:

a) Blockade of mGlu2 and mGlu3 receptors by an antagonist of mGluR2 and mGluR3 (also referred to herein as an "mGlu2/3 receptor antagonist"), for example by administration of the mGlu2/3 receptor antagonist LY341495, attenuates the depression-like aspects of nicotine withdrawal in rats;

b) Treatment with an mGlu5 receptor antagonist, such as MPEP, decreases cocaine and nicotine consumption in rats and mice.

c) Treatment with an antagonist of mGlu2 and mGlu3 receptors, such as LY341495, decreases nicotine consumption in rats;

d) Co-administration of a dose of an mGlu5 receptor antagonist, such as MPEP at 1 mg/kg, that has no effects on cocaine or nicotine self-administration potentiates the inhibitory effects of an mGlu2/3 receptor antagonist, such as LY341495 (0.5 mg/kg or 1 mg/kg), on nicotine self-administration; and e) The combination of an mGlu5 receptor antagonist at a concentration that decreases either cocaine or nicotine self-administration when administered alone, e.g., 9 mg/kg MPEP, when combined with an mGlu2/3 receptor antagonist at a concentration that decreases nicotine self-administration when administered alone, such as 1 mg/kg LY341495, is more effective at decreasing nicotine self-administration than any one drug alone.

Based on these findings, the present invention provides a method for treating a metabotropic glutamate disorder that includes administering to a subject in need thereof, an effective amount of at least one antagonist which modulates mGluR2, mGluR3, and mGluR5, thereby treating the disorder. In another embodiment, methods are provided for treating a metabotropic glutamate disorder including administering to a subject in need thereof an effective amount of at least one antagonist which modulates mGluR2 and mGluR5, thereby treating the disorder. In still another embodiment, methods are provided for treating a metabotropic glutamate disorder including administering to a subject in need thereof an effective amount of at least one antagonist which modulates mGluR3 and mGluR5, thereby treating the disorder. In still another embodiment, methods are provided for treating a metabotropic glutamate disorder including administering to a subject in need thereof an effective amount of at least one antagonist which modulates mGluR2 and mGluR3 and one antagonist that modulates mGluR5, thereby treating the disorder. In still another embodiment, methods are provided for treating a metabotropic glutamate disorder including administering to a subject in need thereof an effective amount of at least one antagonist which modulates mGluR2 and mGluR3, thereby treating the disorder. Because of the known similarities of mGluR1 and mGluR5 (both belonging to Group I), an antagonist of mGluR1 can be used in place of an mGluR5 antagonist in any of the methods of the present invention.

In certain embodiments of the invention, simultaneous antagonism of metabotropic glutamate receptors 2, 3 and 5, is accomplished by administering to a subject in need thereof, one antagonist which acts as an inhibitor of all three receptors. Alternatively, a combination of antagonists can be used to achieve inhibition of receptors 2, 3, and 5. For example, administration of an antagonist of mGluR2 and mGluR3 in combination with an antagaonist of mGluR 5 is used in certain aspects of the invention, to achieve inhibition of mGluRs 2, 3, and 5. For example, the mGluR2 and mGluR3 antagonist LY341495, in combination with the mGluR5 antagonist MPEP, can be administered to a subject.

Furthermore, the present invention provides a combination comprising (a) at least one active ingredient selected from a metabotropic glutamate receptor 2 antagonist and a metabotropic glutamate receptor 3 antagonist, and (b) at least one metabotropic glutamate receptor 5 antagonist, in which the active ingredients are present in each case in free form or in the form of a pharmaceutically acceptable salt, and optionally at least one pharmaceutically acceptable carrier; for simultaneous, separate or sequential use, especially in the treatment of an addictive disorder or depression;

a combination comprising (a) at least one active ingredient which exhibits antagonistic activity against the metabotropic glutamate receptor 2 and the metabotropic glutamate receptor 3, and (b) at least one metabotropic glutamate receptor 5 antagonist, in which the active ingredients are present in each case in free form or in the form of a pharmaceutically acceptable salt, and optionally at least one pharmaceutically acceptable carrier; for simultaneous, separate or sequential use, especially in the treatment of an addictive disorder or depression;

a combination comprising (a) at least one metabotropic glutamate receptor 2 antagonist, and (b) at least one active ingredient which exhibits antagonistic activity against the metabotropic glutamate receptor 3 and the metabotropic glutamate receptor 5, in which the active ingredients are present in each case in free form or in the form of a pharmaceutically acceptable salt, and optionally at least one pharmaceutically acceptable carrier; for simultaneous, separate or sequential use, especially in the treatment of an addictive disorder or depression; and a combination comprising (a) at least one metabotropic glutamate receptor 3 antagonist, and (b) at least one active ingredient which exhibits antagonistic activity against the metabotropic glutamate receptor 2 and the metabotropic glutamate receptor 5, in which the active ingredients are present in each case in free form or in the form of a pharmaceutically acceptable salt, and optionally at least one pharmaceutically acceptable carrier; for simultaneous, separate or sequential use, especially in the treatment of an addictive disorder or depression.

The combinations mentioned above can be applied in the form of a combined preparation or a pharmaceutical composition.

Additionally, the present invention relates to the following aspects:

a method of treating a warm-blooded animal having an addictive disorder or depression comprising administering to the animal a combination according defined above in a quantity which is jointly therapeutically effective against an addictive disorder or depression and in which the compounds can also be present in the form of their pharmaceutically acceptable salts;

a pharmaceutical composition comprising a quantity, which is jointly therapeutically effective against an addictive disorder or depression, of a pharmaceutical combination as defined above and at least one pharmaceutically acceptable carrier;

the use of a combination as defined above for the preparation of a medicament for the treatment of an addictive disorder or depression; and a commercial package comprising a combination defined above together with instructions for simultaneous, separate or sequential use thereof in the treatment of an addictive disorder or depression.

The term "a combined preparation", as used herein defines especially a "kit of parts" in the sense that the first and second active ingredient as defined above can be dosed independently or by use of different fixed combinations with distinguished amounts of the ingredients, i.e., simultaneously or at different time points. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the active ingredients. The ratio of the total amounts of the active ingredient 1 to the active ingredient 2 to be administered in the combined preparation can be varied, e.g., in order to cope with the needs of a patient sub-population to be treated or the needs of the single patient which different needs can be due to age, sex, body weight, etc. of the patients. Preferably, there is at least one beneficial effect, e.g., a mutual enhancing of the effect of the first and second active ingredient, in particular a synergism, e.g. a more than additive effect, additional advantageous effects, less side effects, a combined therapeutic effect in a non-effective dosage of one or both of the first and second active ingredient, and especially a strong synergism the first and second active ingredient.

The pharmacological activity of a combination as defined above may, for example, be evidenced in preclinical studies known as such, e.g. in analogy to those described in the Examples.

The pharmacological activity of a combination as defined above may, for example, also be demonstrated in a clinical study. Such clinical studies are preferably randomized, double-blind, clinical studies in patients with addictive disorders or depression. Such studies demonstrate, in particular, the synergism of the active ingredients of the combination as defined above. The beneficial effects on addictive disorders or depression can be determined directly through the results of these studies or by changes in the study design which are known as such to a person skilled in the art.

Antagonists and agonists of mGlu receptors are known in the art. Examples of some known antagonists and agonists are provided in the Table below and in the following paragraphs. Agonists include non-selective agonists: 1S,3 R-ACPD; 1S,3 S-ACPD; L-CCG-I. Antagonists include broad-spectrum, non-selective antagonists such as (S)-MCPG. It will be understood that based on the teachings of the present invention, virtually any mGluR 1, 2, 3, and/or 5 antagonist can be used with the methods of the present invention. However, preferably for the present invention, antagonists that are selective for mGluR1, R2, R3 and/or R5 are used. Antagonists of mGluR2 are known in the art and include, for example, the compounds disclosed in U.S. Pat. No. 6,407,094 (Adam et al., (2002), incorporated in its entirety herein by reference) and 1-[(Z)-2-Cycloheptyloxy-2-(2,6-dichloro-phenyl)-vinyl]-1H-[1,2,4]triazole (Kolczewski et al. *Bioorg. Med. Chem. Lett.* 1999, 9, 2173-2176). Antagonists of both mGluR2 and mGluR3 are known in the art and include, for example, LY341495 (Kingston et al. *Neuropharm.* 1998, 37, 1-12), LY366457 (O'Neill M. F., et al., *Neuropharmacology*, 45(5): 565-74 (2003)), (2S)-alpha-ethylglutamic acid (EGLU) (See e.g., Neto, F. L., et al., *Neurosci. Lett.* 15; 296(1):25-8 (2000)), and (2S,4S)-amino-4-(2,2-diphenylethyl)pentanedioic acid (Escribano, A., et al., *Bioorg. Med. Chem. Lett.,* 7; 8(7):765-70 (1998)). Antagonists of mGluR5 are known in the art and include, for example, MPEP (2-methyl-6-(phenylethynyl)pyridine) and MTEP (3-(2-Methyl-thiazol-4-ylethynyl)-pyridine (Cosford, N. D., et al., *J. Med. Chem.,* 46(2):204-6 (2003)). Antagonists of mGluR1 include, for example, 3-methyl-aminothiophene dicarboxylic acid (3-MATIDA), (Moroni, F., *Neuropharmacology,* 42(6):741-51 (2002)). Antagonists of mGluR1 and mGluR5 (Group I antagonists), include, for example, 1-aminoindan-1,5-dicarboxylic acid (AIDA) (See e.g., Renaud, J., et al., *Epilepsia,* 43(11):1306-17 (2002)), (3aS,6aS)-6a-naphtalen-2-ylmethyl-5-methyliden-hexahydro-cyclopenta[c]furan-1-on (BAY 36-7620) (See e.g., De Vry, J., et al., *Eur. J. Pharmacol.* 5; 428(2):203-14 (2001)), and the cyclobutylglycine (+/−)-2-amino-2-(3-cis and trans-carboxycyclobutyl-3-(9-thioxanthyl)propionic acid) (LY393053) (Chen, U., et al., *Neuroscience,* 95(3):787-93 (2000)). Other mGluR antagonists that can be used in the present invention include those disclosed in WO99/08678, incorporated in its entirety herein by reference.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

TABLE

Table of mGluR Agonists and Antagonists

| Group | Receptor Subtype | Receptor Agonist | Receptor Antagonist |
|---|---|---|---|
| Group I | mGlu1 | (S)-3,5-DHPG | LY 367385 |
| | | Quisqualate | (S)-4-CPG |
| | | | CPCCOEt |
| | mGlu5 | (S)-3,5-DHPG | MPEP |
| | | (RS)-CHPG | (S)-4-CPG |
| | | Z-CBQA | MTEP |
| | | Quisqualate | |
| Group II | mGlu2 | LY354740 | LY341495 |
| | | LY379268 | ADED |
| | | (2R,4R)-APDC | EGlu |
| | | DCG-IV | MSOP |
| | mGlu3 | LY354740 | LY341495 |
| | | LY379268 | ADED |
| | | (2R,4R)-APDC | |
| | | DCG-IV | |
| Group III | mGlu4 | L-AP4 | DCG-IV |
| | | LY379268 | MAP4 |
| | | L-SOP | MSOP |
| | | (RS)-PPG | MPPG |
| | | | CPPG |
| | mGlu6 | L-AP4 | DCG-IV |
| | | L-SOP | |
| | | (RS)-PPG | |
| | | (S)-HomoAMPA | |
| | mGlu7 | L-SOP | DCG-IV |
| | | (RS)-PPG | MPPG |
| | mGlu8 | L-AP4 | DCG-IV |
| | | LY354740 | MAP4 |
| | | LY379268 | |
| | | L-SOP | |
| | | (RS)-PPG | |

MPEP can be prepared according to the chemical procedures described in WO99/02497 or purchased from Tocris, Ballwin, Mo. LY341495 (2S-2-amino-2-(1S,2S-2-carboxy-cyclopropan-1-yl)-3-(xanth-9-yl)propionic acid) can be purchased from Tocris (Ballwin, Mo.). NBQX disodium (2,3-dioxo-6-nitro-1,2,3,4-tetrahydrobenzo(f)quinoxaline-7-sulphonamide disodium) can be purchased from Tocris, Ballwin, Mo.

As used herein, an "effective amount" of an antagonist is an amount that modulates the normal activity of mGlu receptors 2, 3, or 5 in a subject. A "normal" activity of mGlu receptor represents a level of activity in a cell or subject not having an mGluR-related disorder and can be determined using methods known in the art, some of which are disclosed herein. For example, LY341495 can be administered at a concentration of about 0.1-50 mg/kg, in certain aspects between 0.1 and 5 mg/kg. In some aspects of the invention, an effective amount of LY341 495 is at least 0.5 mg/kg, for example, 0.5 mg/kg to about 10 mg/kg, or 0.5 mg/kg to about 5 mg/kg. In certain aspects of the invention, LY341495 is administered at a concentration of about 0.5 mg/kg or 1 mg/kg.

MPEP, in certain aspects of the invention, is administered in an amount of between about 0.01 and 25 mg/kg body weight. In certain aspects, MPEP is administered at a concentration equal to or greater than 1 mg/kg, for example between about 3 and about 20 mg/kg. In other aspects, MPEP is administered at a concentration of between about 5 and about 15 mg/kg. In other aspects, MPEP is administered at between about 7 and about 12 mg/kg, for example at 9 mg/kg.

In one aspect of the invention, two or more antagonists are administered at sub-effective amounts, below which one or more of the antagonists are effective at treating the disorder on their own. For example, an mGluR5 antagonist can be administered at a sub-effective amount and an mGluR2/mGluR3 antagonist can be administered at an effective amount, or vice versa. MPEP can be administered at 1 mg/kg or less and LY341495 can be administered at an effective concentration, as indicated above. For example, MPEP can be administered at 0.1-3 mg/kg and LY341495 can be administered at 0.5-5 mg/kg. In one aspect illustrated in Example 3, MPEP is administered at 1 mg/kg and LY341495 is administered at 0.5 mg/kg. In addition, other specific aspects of the present invention include the combination of 1 mg/kg LY341495 and 1 mg/kg MPEP; and 1 mg/kg LY341495 and 9 mg/kg MPEP. As illustrated in Example 3, when used in combination, an mGluR5 antagonist enhances the effectiveness in treating an addictive disorder, such as nicotine addiction, of an mGluR2/R3 antagonist. As also illustrated in Example 3, when used in combination, an mGluR2/3 antagonist enhances the effectiveness in treating an addictive disorder, such as nicotine addiction, of an mGluR5 antagonist. It will be understood that the present invention provides a basis for further studies in humans to more precisely determine effective amounts in humans. Doses used in the Examples section for rodent studies provide a basis for the ranges of doses indicated herein for humans and other mammals.

In certain aspects of the invention, for example, an amount of one or more mGluR2, 3, and/or 5 antagonist is administered that is sufficient to diminish, inhibit, or eliminate desire for an addictive substance such as cocaine or nicotine. Furthermore, in certain aspects, an amount of an mGluR2, 3, and/or 5 antagonist is administered that is sufficient to diminish, inhibit, or eliminate the reinforcing properties of an addictive substance, such as cocaine or nicotine. Furthermore, in certain aspects, an amount of an mGluR2 and/or 3 antagonist is administered that is sufficient to diminish, inhibit, or eliminate depression, such as the depression associated with withdrawal from an addictive substance, such as cocaine or nicotine, or depression associated with drug use, or depression not associated with any drug use. Diminution, inhibition, and/or elimination of any of these characteristics of the diseases targeted by the methods of the present invention indicate effective treatment of a metabotropic glutamate disorder.

Disorders that can be effectively treated by modulating the activity of mGluRs 2, 3, and 5, referred to herein as metabotropic glutamate disorders, include addictive disorders and depression. Metabotropic glutamate disorders include disorders that involve one or both of a Group I metabotropic glutamate receptor (mGluR) and one or both of a Group II mGluR. Addictive metabotropic glutamate disorders include, for example, nicotine addiction, alcohol addiction, opiate addiction, amphetamine addiction, cocaine addiction, methamphetamine addiction, and the like.

It will be understood that the data provided in the Examples section for certain drugs of abuse, such as cocaine and nicotine, is applicable to other drugs of abuse as well. It has been extensively hypothesized that dependence on all major drugs of abuse is mediated by the same neurobiological and behavioral mechanisms (Markou et al. 1998; Markou A & Kenny P J 2002 Neuroadaptations to chronic exposure to drugs of abuse: Relevance to depressive symptomatology seen across psychiatric diagnostic categories, *Neurotoxicity Research*, 4(4), 297-313; Koob & Le Moal, *Neuropsychopharmacology*, 24(2):97-129 2001; Barr, A. M., Markou, A. and Phillips, A. G. (2002) A "crash" course on psychostimulant withdrawal as a model of depression, *Trends in Pharmacological Sciences*, 23(1), 475-482, incorporated in its entirety by reference; Cryan, J. F., Markou, A. and Lucki, I. (2002) Assessing antidepressant activity in rodents: Recent developments and future needs, *Trends in Pharmacological Sciences*, 23(5), 238-245). Thus, one would expect that a compound effective in treating one drug addiction is likely to be effective in treating another addiction also. For example, increase in serotonergic neurotransmission by co-administration of the selective serotonin reuptake inhibitor fluoxetine+the serotonin-1A receptor antagonist p-MPPI reversed the depression-like aspects of both amphetamine and nicotine withdrawal (Harrison, Liem & Markou, *Neuropsychopharmacology* 2001; incorporated in its entirety by reference). Further, withdrawal from all major drugs of abuse (nicotine, cocaine, amphetamine, alcohol, opiates, phencyclidine) results in elevations in brain reward thresholds reflecting a depression-like state (references in reviews Markou et al. 1998; Markou & Kenny 2002; Barr et al. 2002; Cryan et al. 2002; and original research reference for phencycline: Spielewoy, C. & Markou, A. 2003, Withdrawal from chronic treatment with phencyclidine induces long-lasting depression in brain reward function, *Neuropsychopharmacology*, 28, 1106-1116 and cocaine: Ahmed et al. 2002). Thus, treating such depression-like aspects of drug dependence and withdrawal may assist people in abstaining from drug use.

In one aspect, the addictive disorder is nicotine addiction. In another aspect, the addictive disorder is cocaine addiction. In another aspect, the addictive disorder is alcohol addiction. In another aspect, the addictive disorder is opiate addiction. In another aspect, the addictive disorder is methamphetamine addiction. In another aspect, the addictive disorder is amphetamine addiction.

In another aspect, the metabotropic glutamate disorder is depression. Example 1 illustrates that blockade of mGluR2/3 receptors has antidepressant properties as reflected in reversal of the negative affective (depression-like) aspects of nicotine withdrawal. Thus, blockade of mGluR2 and mGluR3 reverses depression-like symptoms observed during drug withdrawal, and possibly depression observed during drug dependence (Ahmed, S. H., et al. *Nature Neuroscience*, 5: 625-626 (2002), incorporated in its entirety by reference). Therefore, administration of an effective amount of an antagonist of mGluR2 and mGlurR3 is likely to be efficacious for treating non-drug-induced depressions, based on the known neurobiological similarities mediating drug- and non-drug-induced depressions (Markou et al. 1998, incorporated in its entirety by reference; Barr et al., 2002, incorporated in its entirety by reference; Cryan et al., 2002; incorporated in its entirety by reference; Harrison et al., *Neuropsychopharmacology*, 25:55-71 (2001), incorporated in its entirety by reference; Markou A and Kenny P J 2002, Neuroadaptations to chronic exposure to drugs of abuse: Relevance to depressive symptomatology seen across psychiatric diagnostic categories, *Neurotoxicity Research*, 4(4), 297-313; incorporated in its entirety by reference). Additional observations further support the conclusion that results presented in Example 1 related to depression-like symptoms of withdrawal of an addictive substance, establish that antagonists of mGluR2 and/or mGluR3 can be used to effectively treat non-drug-induced depressions, as well. First, it has been shown that co-administration of the selective serotonin reuptake inhibitor fluoxetine and the serotonin-1A receptor antagonist p-MPPI, a clinically proven antidepressant drug treatment, reverses the depression-like aspects of both nicotine and amphetamine withdrawal (Harrison et al., (2001); incorporated in its entirety by reference). Second, as shown in Example 4, co-administration of the selective serotonin reuptake inhibitor paroxetine and the serotonin-1A receptor antagonist p-MPPI, another clinically proven antidepressant drug treatment, also reversed amphetamine withdrawal. Third, bupropion, another clinically proven antidepressant treatment, reverses the depression-like aspects of nicotine withdrawal (Cryan, J. F., et al., *Psychopharmacology*, 168, 347-358 (2003); Example 5). Thus, clinically proven antidepressant treatments reverse the depression-like aspects of drug withdrawal in the model presented in Examples 1 and 4. Therefore, it can be inferred that a treatment (e.g., mGluR2/3 antagonist) that normalized thresholds in the model, would be a clinically effective treatment. Further, the reversal of both amphetamine and nicotine withdrawal by the same antidepressant treatment indicates that there are commonalities in various types of depression, independent of what the depression-induction mechanism is and/or the primary site of action of the drug of abuse (nicotinic receptor for nicotine, monoaminergic transporters for amphetamine).

The present invention in another embodiment, provides a method for treating depressive symptoms and anxiety symptoms of depression. The method includes administering to a subject in need thereof, an effective amount of at least one antagonist which modulates mGluR2, mGluR3, and mGluR5, thereby treating the depressive symptoms and anxiety symptoms. In another aspect of this embodiment of the invention, at least one antagonist of mGluR2 and/or R3 is administered during a depressed time period, wherein the subject experiences symptoms of depression, whereas an mGluR5 antagonist is administered during time periods when the subject experiences symptoms of anxiety. Depression is characterized by both depressive symptoms and anxiety symptoms. Thus, the present invention, which provide an mGluR2/3/5 combination treatment provides an effective antidepressant, with the mGluR2/3 antagonism ameliorating depressive symptoms and the mGluR5 antagonist ameliorating anxiety symptoms. Accordingly, this embodiment takes advantage of the anti-depressive properties of mGluR2/3 antagonists and the anxiolytic properties of mGluR5 antagonists (See e.g., Cosford, N. D., et al., *J. Med. Chem.* 16; 46(2):204-6 (2003); Brodkin J., et al., *Eur. J. Neurosci.*, 16(11):2241-4 (2002); and Brodkin J., et al., *Pharmacol. Biochem. Behav.* 73(2):359-66 (2002)). Since anxiety is known to be a major symptom of the overall syndrome of depression, this embodiment of the invention is effective at treating the anxiety symptoms of depression.

Depressive symptoms and anxiety symptoms are well known in the art. Methods of this embodiment of the invention treat one or more symptoms of depression and one or more symptoms of anxiety. Symptoms of depression, include, for example, but are not limited to, the following: a persistent sad, anxious or "empty" mood; sleeping too little or sleeping too much; reduced appetite and weight loss, or increased appetite and weight gain; loss of interest or pleasure in activities once enjoyed; restlessness or irritability; persistent physical symptoms that don't respond to treatment (e.g., headaches, chronic pain, or constipation and other digestive disorders); difficulty concentrating, remembering, or making decisions; fatigue or loss of energy; feeling guilty, hopeless or worthless; and thoughts of death or suicide.

Symptoms of anxiety include, but are not limited to, the following:

excessive worry, occurring more days than not, over a period of months, for example over a period of at least six months; unreasonable worry about a number of events or activities, such as work or school and/or health; the inability to control worry; restlessness, feeling keyed-up or on edge; tiredness; problems concentrating; irritability; muscle tension; and trouble falling asleep or staying asleep, or restless and unsatisfying sleep.

In certain aspects of embodiments of the present invention directed at methods for treating a metabotropic glutamate disorder, the subject is a mammalian subject, for example a human subject afflicted with a metabotropic glutamate receptor disorder, for example nicotine addiction, cocaine addiction, or depression. The examples herein illustrate the methods of the present invention in rodents. However, it will be understood that the methods are expected to be efficacious in human subjects as well, due to the similarity between rodents and humans in the physiology of addictive disorders and depression (Markou et al. 1998; Markou and Kenny 2002, incorporated in its entirety by reference), and the structure of mGlu receptors (Schoepp et al. *Neuropharm.* 1999, 38, 1431-1476); Schoepp D D (2001), J Pharmacol Exp Ther 299:12-20).

"Simultaneous administration" of two or more antagonists is administration of the agonists to a subject within a short enough time period such that a sufficient concentration of each of the antagonists is present in the subject at the same time to modulate their respective mGlu receptor targets. Therefore, it will be recognized that the maximum time difference between administrations of antagonists that represent simultaneous administration depends on the half-life of the antagonists administered, the amount of antagonist administered, and the method and location by which the antagonists are administered, for example.

For certain aspects of the methods of the present invention, the antagonists are administered for periods of weeks, months, years, and possibly indefinitely for subjects exhibiting failure to abstain from drug use or for chronic depressive disorders that may be unrelated to drug use or induced by drug use, but not remitting spontaneously without the methods suggested herein.

The present invention, in another embodiment, provides a method for inhibiting drug-taking behavior, treating depression, and/or treating the depression-like state associated with drug use and dependence (Ahmed et al., 2002, incorporated herein in its entirety by reference), or with addictive drug withdrawal, that includes administering to a subject in need thereof, an effective amount of at least one antagonist which modulates mGluR2 and/or mGluR3, thereby treating consumption of the addictive substance, depression, or the depression-like state of the addictive drug dependence or drug withdrawal states. This embodiment is based on the experimental evidence provided in Example 3 that treatment with an antagonist at mGlu2/3 receptors, such as LY341495, decreases addictive drug (e.g., nicotine) consumption in rats, as well as the evidence provided in Example 1 that treatment with an mGlu2/3 receptor antagonist, such as LY341495, can reverse the depression-like state associated with drug withdrawal. The addictive substance for example, is nicotine or cocaine. In certain aspects, the effective amount of at least one antagonist is administered to decrease nicotine consumption. For example, in one aspect an effective amount of an antagonist of mGluR2 and mGluR3, such as LY341495, is administered to decrease nicotine consumption. In certain aspects of the invention, an inhibitor of mGluR2 and/or mGluR3 is administered while a subject is experiencing withdrawal. In another aspect of the invention, an inhibitor of mGluR2 and/or mGluR3 is administered during a time period when a subject is actively using an addictive substance. In another aspect of the invention, an inhibitor of mGluR2 and/or mGluR3 is administered during a time period when a subject is actively experiencing depression associated with drug use or not associated with drug use.

The present invention, in another embodiment, provides a method for antagonizing at least two of mGluR2, mGluR3, and mGluR5, that includes simultaneously administering to a subject in need thereof, an amount of at least two antagonists that modulate at least two of mGluR2, mGluR3, and mGluR5. The amount of each antagonist is sufficient to modulate its target mGluR. This amount may be less than an effective amount of the antagonist when administered alone. However, the amount administered in these embodiments is sufficient so that the combination of antagonists is effective for treating a metabotropic disorder. In certain aspects, each antagonist is provided at an effective amount for treating a metabotropic glutamate disorder. In certain aspects, the subject is afflicted with depression, a nicotine addiction, or a cocaine addiction. In certain aspects, an antagonist that modulates mGluR2 and mGluR3 is administered along with an antagonist that modulates mGluR5. For example, an effective amount of MPEP can be administered along with an effective amount of LY341495. In another embodiment, a sub-effective amount of MPEP is administered along with an effective amount of LY341495. In another embodiment, an effective amount of MPEP is administered along with a sub-effective amount of LY341495. In another embodiment, a sub-effective amount of MPEP is administered along with a sub-effective amount of LY341495.

The present invention in another embodiment provides a method for treating an addictive disorder, also referred to herein as substance abuse, that includes administering to a subject in need thereof, an effective amount of at least one antagonist that modulates at least one of mGluR2, 3, and 5 during a first time period, followed by administering at least one antagonist that modulates at least one of mGluR2 and/or 3 during a second time period. The first time period, for example, is a time period wherein the subject expects to be in an environment wherein, or exposed to stimuli in the presence of which, the subject habitually uses an addictive substance, or wherein the subject is actively using the addictive substance. The second time period, for example, is a time period wherein the subject is suffering from withdrawal and/or depression. One aspect of this embodiment of the invention, for example, includes administering MPEP and/or LY341495 during a first time period, and administering LY341495 during a withdrawal or depression period.

This embodiment is based on the finding presented in the Examples herein that administration of an antagonist of mGluR5 and/or an antagonists of mGluR213 decrease self-administration of an addictive drug such as nicotine or cocaine. Furthermore, this embodiment is based on the finding that administration of an antagonist of mGluR2/3 reverses at least some of the negative effects of nicotine withdrawal. In one aspect of this embodiment, an antagonist of mGluR5 and an antagonist of mGluR2 and/or mGluR3 are administered and the depression-like symptoms of drug dependence and withdrawal are monitored. If withdrawal symptoms or depression symptoms become too intense, administration of the mGluR5 antagonist can be terminated at least temporarily, while the mGluR2/3 antagonist can continue to be administered.

In certain embodiments of the invention, an addictive or depressive disorder is treated by administering an effective amount of an AMPA/Kainate receptor agonist or partial agonist to a subject. In certain aspects of this embodiment, one or more agonists or partial agonists are administered to the subject that modulate the AMPA/Kainate receptor as well as at least one of the mGluR2, mGluR3, and mGluR5 receptors. Typically, one agonist or partial agonist of the AMPA/Kainate receptor is administered along with at least one antagonist of mGluR2, mGluR3, and/or mGluR5. In certain embodiments one or more agonists or partial agonists are administered that modulate the AMPA/Kainate receptor and antagonists that modulate the mGluR5, for example by administration of AMPA/Kainate agonists or partial agonists and MPEP. In another embodiment one or more agonists or partial agonists are administered that modulate the AMPA/Kainate receptor, along with one or more antagonists that modulate mGluR2 and/or mGluR3.

AMPA/Kainate receptor agonists or partial agonists include, for example, CPCCOet (7-hydroxyiminocyclopropan[b]chromen-1a-carboxylic acid ethyl ester (Litschig S., et al., Molecular Pharmacology 55(3):453-561 (1999)). The use of AMPA/Kainate receptor partial agonists provides an advantage over AMPA/Kainate agonists, that the partial agonists generally have better side-effect profiles.

The route of delivery of the antagonists or agonists employed by invention methods is determined by the particular disorder. Antagonists or agonists may be delivered orally, intravenously, intraperitoneally, intramuscularly, subcutaneously, intranasally, and intradermally, as well as, by transdermal delivery (e.g., with a lipid-soluble carrier in a skin patch placed on skin), or even by gastrointestinal delivery (e.g., with a capsule or tablet). Furthermore, antagonists or agonists used in the methods of the present invention, in certain aspects are delivered directly to the brain or certain regions of the brain to activate or inhibit receptors at specific brain sites producing the desirable effect without inhibiting or activating receptors at other brain sites, thus avoiding undesirable side-effects or actions that may counteract the beneficial therapeutic action mediated by the former site(s). The dosage will be sufficient to provide an effective amount of an antagonist either singly or in combination, as discussed above. Some variation in dosage will necessarily occur depending upon the condition of the patient being treated, and the physician will, in any event, determine the appropriate dose for the individual patient. The dose will depend, among other things, on the body weight, physiology, and chosen administration regimen.

The antagonists employed in invention methods are administered alone or in combination with pharmaceutically acceptable carriers, in either single or multiple doses. Suitable pharmaceutical carriers include inert solid diluents or fillers, sterile aqueous solutions, and various nontoxic organic solvents. The pharmaceutical compositions formed by combining one or more antagonist with the pharmaceutically acceptable carrier are then readily administered in a variety of dosage forms such as tablets, lozenges, syrups, injectable solutions, and the like. These pharmaceutical carriers can, if desired, contain additional ingredients such as flavorings, binders, excipients, and the like. Thus, for purposes of oral administration, tablets containing various excipients such as sodium citrate, calcium carbonate, and calcium phosphate are employed along with various disintegrants such as starch, and preferably potato or tapioca starch, alginic acid, and certain complex silicates, together with binding agents such as polyvinylpyrolidone, sucrose, gelatin, and acacia. Additionally, lubricating agents, such as magnesium stearate, sodium lauryl sulfate, and talc are often useful for tableting purposes. Solid compositions of a similar type may also be employed as fillers in salt and hard-filled gelatin capsules. Preferred materials for this purpose include lactose or milk sugar and high molecular weight polyethylene glycols.

When aqueous suspensions of elixirs are desired for oral administration, the antagonists may be combined with various sweetening or flavoring agents, colored matter or dyes, and if desired, emulsifying or suspending agents, together with diluents such as water, ethanol, propylene glycol, glycerin, and combinations thereof. For parenteral administration, solutions of preparation in sesame or peanut oil or in aqueous polypropylene glycol are employed, as well as sterile aqueous saline solutions of the corresponding water soluble pharmaceutically acceptable metal salts previously described. Such an aqueous solution should be suitably buffered if necessary and the liquid diluent first rendered isotonic with sufficient saline or glucose. These particular aqueous solutions are especially suitable for intravenous, intramuscular, subcutaneous, and intraperitoneal injection. The sterile aqueous media employed are all readily obtainable by standard techniques well known to those skilled in the art.

In another embodiment, the present invention provides a method of screening for an agent that improves the ability of a known inhibitor to at least partially normalize intracranial self-stimulation (ICSS) threshold and/or improves the ability of a known inhibitor to inhibit consumption of an addictive substance for a non-human, mammalian subject. The method includes:

a) affecting the ICSS threshold of the subject;
   b) administering to the subject, a sufficient amount of the known inhibitor to inhibit consumption of an addictive substance and/or at least partially normalize the ICSS threshold when administered alone or in combination with another inhibitor, wherein the known inhibitor is an antagonist of mGluR2 and/or mGluR3 and/or mGluR5;
   c) administering to the subject, an effective amount of a test agent, wherein the test agent is a known or suspected antagonist of mGluR2 and/or mGluR3 and/or mGluR5; and
   d) determining whether the test agent improves the ability of the known inhibitor, to at least partially normalize the ICSS threshold, and optionally to inhibit one or both of consumption of the addictive substance, thereby identifying an agent that improves the ability of the known inhibitor to normalize ICSS threshold and/or improves the ability of a known inhibitor to inhibit consumption of an addictive substance, or, alternatively, determining whether the test agent improves the ability of the known inhibitor, to at least decrease consumption of an addictive substance, and optionally to partially normalize the ICSS threshold or both thereby identifying an agent that improves at least the ability of the known inhibitor to inhibit consumption of an addictive substance and/or normalize ICSS threshold.

Intracranial self-stimulation (ICSS) thresholds are at least partially normalized when an increase or decrease on ICSS threshold caused by a metabotropic glutamate disorder is at least partially inhibited (i.e. adjusted back to the ICSS threshold of a subject that is not afflicted with the metabotropic glutamate disorder). For example, withdrawal from chronic nicotine administration (Kenny et al., 2003) or chronic self-administration of cocaine (Ahmed et al. 2002, incorporated in its entirety by reference) are known to elevate an ICSS threshold (see e.g., Kenny et al. 2003). Therefore, partial normalization of an ICSS threshold during cocaine administration or during nicotine withdrawal will lower the ICSS threshold from the elevated threshold, reflecting a depressed state, normally found during chronic cocaine administration or nicotine withdrawal, closer to that found in a normal subject. Accordingly, methods of this embodiment of the invention can utilize chronic administration of an addictive substance (e.g., cocaine) or termination of administration of an addictive substance (e.g., nicotine) to affect (i.e., denormalize) the ICSS threshold before or during administration of the known inhibitor and the test agent. Acute administration of an addictive substance typically decreases the ICSS threshold, while chronic administration of an addictive substance and/or termination of administration of an addictive substance typically increases the ICSS threshold.

In addition to the methods above, the ICSS threshold can be affected by other known methods. For example, the chronic mild stress procedure can be used to induce threshold elevations reversible by antidepressant treatments (Moreau J. L., Bos M., Jenck F., Martin J. R., Mortas P. and Wichmann J. (1996), *Eur Neuropsychopharmacology*, 6, 169-175; Moreau J. L., Bourson A., Jenck F., Martin J. R. and Mortas P. (1994), *J Psychiatry Neurosci* 19, 51-56; Moreau J. L., Jenck F., Martin J. R., Mortas P. and Haefely W. E. (1992), *Eur Neuropsychophartnacoogy*, 2, 43-49).

Methods for self-administration of an addictive agent and for analyzing ICSS are disclosed in the Examples section. The methods of the present invention not only can be used to identify an agent that is effective at improving the effectiveness of a known inhibitor, but also can be used to determine which of the characteristics/symptoms/aspects associated with substance abuse or withdrawal are effected by the test agent, as illustrated in the Examples, and discussed further in the following paragraphs.

Methods analyzing consumption of an addictive substance can be performed under a self-administration fixed ratio schedule of reinforcement or under a progressive schedule of reinforcement, examples of which are provided in Examples 2 and 3. In a fixed ration schedule, an animal responds a 'fixed' number of times on an active lever to obtain a drug infusion. Fixed ratio (FR) schedules of reinforcement provide important information as to whether a drug is reinforcing. In contrast, under a progressive ratio (PR) schedule of reinforcement, each time an animal responds on the active lever to receive a drug infusion, the number of times that the animal must subsequently respond to receive the next infusion is progressively increased. By determining how hard an animal is willing to work for a drug injection, while limiting total intake, the PR schedule allows better separation of motivation for drug consumption from possible satiating effects of cumulative drug doses (Stafford et al. 1998).

These characteristics result in theoretically different interpretations of the factors controlling drug-seeking and drug-taking behavior on a PR compared with a FR schedule of reinforcement. For example, some researchers have suggested that FR schedules measure the pleasurable or hedonic effects of a drug (McGregor and Roberts 1995; Mendrek et al. 1998), whereas PR schedules provide a better measure of the incentive or the 'motivation' to obtain a drug (Markou et al., 1993). After acquisition of cocaine or nicotine self-administration under an FR schedule, as described above, rodents, such as rats or mice, can be switched to a PR schedule of reinforcement in which an increasing sequence of level presses can be required to receive each subsequent infusion of an addictive substance such as nicotine or cocaine, or trained from the beginning on the PR schedule For example, 5, 10, 17, 24, 32, 42, 56, 73, 95, 124, 161, 208, etc. level presses can be required to receive each subsequent infusion under a progressive ratio schedule of reinforcement. In certain aspects, a test agent can be administered to a non-human subject for a period of time, for example, 15 minutes, 30, minutes, 45 minutes, 1 hour, etc. before the subject is placed in a PR of FR schedule of reinforcement session. The session can be conducted for a fixed period of time (e.g., 1 hour, 2 hours, 3 hours, 4 hours, etc.). A break-point can be determined for each session. Break-point is defined as the highest ratio (i.e., the highest number of lever presses emitted for a drug injection within the time period allowed, usually 1 hour since the last drug injection was earned) achieved before the session is terminated; the session is terminated if the subject failed to earn a drug infusion during one hour.

Screening methods of the invention can also be used to determine whether a test agent reduces the hedonic actions of cocaine. Cocaine-induced lowering of ICSS thresholds represents an accurate measure of cocaine's hedonic and euphorigenic actions. Thus, to test the hypothesis that a test agent attenuates the hedonic actions of cocaine, a test agent's effect on cocaine-induced lowering of ICSS thresholds can be determined. Cocaine can be used at an amount sufficient to lower an ICSS threshold, for example 10 mg/kg, without affecting performance in the ICSS procedure (Kenny et al., 2002b; Markou & Koob 1992).

Furthermore, depression-like symptoms of withdrawal and drug dependence can be measured by measuring the increase in ICSS reward threshold that occurs after termination of administration of an addictive substance and during (or closely timely related, such as immediately before and/or after) drug consumption. Therefore, a test agent's ability to inhibit these depression-like symptoms can be measured by determining whether the test agent at least partially inhibits the increase in ICSS reward threshold that occurs during drug use or withdrawal (i.e. normalized the threshold). Methods for determining ICSS thresholds are known in the art and disclosed in the Example section. Therefore, screening methods of this embodiment of the invention not only identify agents that improve the inhibition by a known inhibitor, they also can be used to identify the specific characteristics of an addiction (e.g., hedonic effects of a drug, motivation to take a drug, depression associated with drug dependence and/or following drug withdrawal) that are improved by the test agent.

In certain aspects of this embodiment, a test agent known or suspected to antagonize mGluR2 and/or mGluR3 is analyzed in combination with a known inhibitor that is an antagonist of mGluR5. Conversely, in other aspects of this embodiment, a test agent known or suspected to antagonize mGluR5, is analyzed with a known inhibitor that is an antagonist of mGluR2 and/or mGluR3. In certain aspects, the known inhibitor is MPEP and the test agent is known or suspected of being an antagonist of mGluR2 and/or mGluR3. In other aspects, the known inhibitor is LY341495 and the test agent is known or suspected of being an antagonist of mGluR5.

For screening embodiments of the invention, the subject is a non-human mammalian subject, for example a primate or a rodent, such as a mouse or a rat. The non-human subject is afflicted with a metabotropic glutamate receptor disorder, for example nicotine addiction, cocaine addiction, or depression. The disease can be induced using methods known in the art, as illustrated by the Examples, or by using lines of organisms that are known to be at increased risk for developing the disorder.

The term "test agent" is used herein to mean any agent that is being examined for the ability to improve the ability of the known inhibitor to inhibit consumption of an addictive substance or normalize ICSS thresholds. The method generally is used as a screening assay to identify molecules that can act as a therapeutic agent for treating depressive disorders or addictive disorders such as cocaine addiction or nicotine addiction. As indicated above, the test agent can be an agent known to inhibit mGluR2, mGluR3, and/or mGluR5. Furthermore, the screening methods of the present invention can be combined with other methods that analyze test agents for the ability to antagonize mGluR2, mGluR3, and/or mGluR5. For example, a cell based high throughput assay can be used to screen for test agents that are antagonists for mGluR2, mGluR3, and/or mGluR5, using methods known in the art. Test agents identified as antagonists of mGluR2, mGluR3, and/or mGluR5 can then be analyzed in the screening method provided in this embodiment of the invention, to determine whether the test agents improve the ability of the known inhibitor to inhibit consumption of an addictive substance or affect ICSS reward thresholds.

A test agent can be any type of molecule, including, for example, a peptide, a peptidomimetic, a polynucleotide, or a small organic molecule, that one wishes to examine for the ability to act as a therapeutic agent, which is an agent that provides a therapeutic advantage to a subject receiving it.

In another embodiment, the present invention provides kits that are useful for carrying out the methods of the present invention. The components of the kits depend on the specific method that is intended to be performed by the kit. For example, the kit can be useful for carrying out a method to treat a metabotropic glutamate disorder. In this aspect, the kit can include at least one container that contains an antagonist that modulates metabotropic glutamate receptor 2 (mGluR2), mGluR3, and/or mGluR5. In one aspect, the kit includes a first container with an inhibitor of mGluR5 and a second container with an inhibitor of mGluR2 and/or mGluR3. In one aspect, the kit includes a container of MPEP and a container of LY341495. The antagonists included in the test kit are provided in an amount and form that is sufficient to allow an effective amount to be administered to the subject. The kit for example, can also include instructions regarding effective use of the antagonists in the treatment of substance abuse and depression. The kit in certain aspects includes information that is generally useful for a depressed individual or an individual suffering from an addiction.

In another aspect, the kits can be useful for screening for an agent that improves the ability of a known inhibitor to inhibit consumption of an addictive substance or at least partially normalize intracranial self-stimulation threshold. In this aspect, the kit for example, includes a container having a known inhibitor. Furthermore, the kit may include a container of an addictive substance to be administered to a non-human mammalian subject.

The present invention in another embodiment provides a method for treating an addictive disorder, that includes administering to a subject in need thereof, an effective amount or sub-effective amount of bupropion during a first time period, and administering of bupropion during a second time period. The first time period, for example, is a time period wherein the subject expects to be in an environment wherein, or exposed to stimuli in the presence of which, the subject habitually uses an addictive substance, or wherein the subject is actively using the addictive substance. The second time period, for example, is a time period wherein the subject is suffering from withdrawal and/or depression. In one aspect of this embodiment, in the first time period bupropion is administered at a lower dose than during the second period.

This embodiment is based on the finding presented in Example 5 that lower doses, in fact sub-effective doses (5 mg/kg) of bupropion were effective at blocking the threshold lowering effects of acute nicotine administration, and higher concentration (10-40 mg/kg) of bupropion administration normalizes ICSS thresholds that were affected by nicotine administration and/or withdrawal. A sub-effective dose of bupropion is a dose that on its own does not lower brain reward thresholds, but that is capable of completely reversing the reward-enhancing effects of acute nicotine.

In another aspect of this embodiment of the invention, the present invention provides a method for treating addictive drug dependence and/or withdrawal and/or depression associated with drug use or drug withdrawal that includes administering to a subject in need thereof, an effective amount of a selective serotonin reuptake inhibitor, such as paroxetine, and a serotonin-1A receptor antagonist. The serotonin-1A receptor antagonist, in certain aspects of the invention, is p-MPPI. Another serotonin-1A receptor antagonist that can be used is pindolol. This embodiment is based on the results presented in Example 4.

In another embodiment the present invention provides a method for treating an addictive disorder that includes administering to a subject in need thereof, an effective amount of a selective serotonin reuptake inhibitor, such as paroxetine, a serotonin-1A receptor antagonist, and/or bupropion, and administrating to the subject an effective amount of an antagonist of mGluR2, mGluR3, and/or mGluR5. In certain aspects of this embodiment, where an mGluR5 antagonist is administered, the mGluR5 administration is stopped during periods wherein the subject suffers from withdrawal. In certain aspects, administration of the selective serotonin reuptake inhibitor, a 5-HT1A receptor antagonist, and/or bupropion is commenced during periods wherein the subject suffers from withdrawal.

The invention will now be described in greater detail by reference to the following non-limiting examples.

Example 1

Group II Metabotropic and AMPA/Kainate Glutamate Receptors Regulate the Deficit in Brain Reward Function Associated with Nicotine Withdrawal in Rats This example illustrates that an antagonist of mGluR2 and mGluR3 receptors and possibly an agonist of AMPA/Kainate glutamate receptors can lower the deficit in brain reward function associated with nicotine withdrawal in rats. Nicotine withdrawal precipitates an aversive abstinence syndrome in human smokers hypothesized to provide an important source of motivation contributing to the persistence of the smoking habit and relapse during abstinence (Kenny and Markou, 2001). The data provided in this example strongly suggest a role for Group II metabotropic glutamate receptors in generating the reward deficits associated with nicotine withdrawal by demonstrating that activation of mGluII receptors precipitated ICSS threshold elevations in nicotine-dependent rats similar to those observed during spontaneous nicotine withdrawal. Further, activation of mGluII receptors in the VTA also elevated thresholds in nicotine-dependent rats, providing further support for an important role of the VTA in mediating the actions of nicotine on reward pathways. Consistent with the above, blockade of mGluII receptors attenuated the reward deficits in rats undergoing spontaneous nicotine withdrawal. Finally, the data provided in this example also strongly suggest a role for AMPA/kainate metabotropic glutamate receptors in generating the reward deficits associated with nicotine withdrawal by demonstrating that antagonism of AMPA/kainite receptors precipitated ICSS threshold elevations in nicotine-dependent rats similar to those observed during spontaneous nicotine withdrawal.

Materials and Methods

Subjects

Subjects were 149 male Wistar rats weighing 300-320 g at the start of each experiment. Rats were obtained from Charles River Laboratories (Raleigh, N.C.) and were housed with food and water available ad libitum. Animals were maintained in a temperature-controlled vivarium under a 12 hr light/dark cycle (lights off at 10:00 am). In each case animals were tested during the dark portion of the light/dark cycle, except for the spontaneous nicotine withdrawal experiment when rats were tested at time-points according to the experimental design.

Drugs (−)-Nicotine hydrogen tartrate salt ((−)-1-methyl-2-(3-pyridyl) pyrrolidine) and (+)-MK-801 hydrogen maleate (5R,10S)-(+)-5-Methyl-10,11-dihydro-5H-dibenzo(a,d)cyclohepten-5,10-imine hydrogen maleate) were purchased from Sigma Chemical Co., St. Louis, Mo.; LY341495 (2S-2-amino-2-(1S,2S-2-carboxycyclopropan-1-yl)-3-(xanth-9-yl) propionic acid) and NBQX disodium (2,3-dioxo-6-nitro-1,2,3,4-tetrahydrobenzo(f)quinoxaline-7-sulphonamide disodium) were purchased from Tocris, Ballwin, Mo. LY314582 (the racemic mixture of LY354740 ((+)-2-aminobicyclo(3.1.0)hexane-2,6-dicarboxylic acid)) and MPEP (2-methyl-6-(phenylethynyl)-pyridine) were synthesized. CGP44532 (3-Amino-2-(S)-hydroxypropyl-methyl-phosphinic acid) was generously provided by Novartis Pharma AG. Drugs were prepared immediately before each administration. For systemic administration, all drugs were dissolved in sterile water and administered by intraperitoneal injection, in a volume of 1 mil/kg body weight, 30 min before the experimental session. For direct intra-VTA administration, LY314582 was dissolved in artificial cerebrospinal fluid (aCSF) of the following composition (in mM): 126.6 NaCl, 27.4 NaHCO$_3$, 2.4 KCI, 0.5 KH$_2$PO$_4$, 0.89 CaCl$_2$, 0.8 MgCl$_2$, 0.48 Na$_2$HPO$_4$ and 7.1 glucose, pH 7.4. Rats received intra-VTA injections immediately prior to the initiation of the experimental session. Unless otherwise stated, drug doses refer to the salt form.

Apparatus

Intracranial self-stimulation training and testing took place in sixteen Plexiglas operant chambers (25×31×24 cm) (Med Associates, St. Albans, Vt.). One wall contained a metal wheel manipulandum that required 0.2 N force to rotate it one-quarter of a turn. The wheel (5 cm in width) extended out of the wall ~3 cm. Intracranial stimulation was delivered by constant current stimulators. Subjects were connected to the stimulation circuit through flexible bipolar leads attached to gold-contact swivel commutators mounted above the chamber. The stimulation parameters, data collection, and all test session functions were controlled by a microcomputer.

Surgery

Placement of electrodes and cannulas. Rats were anaesthetized by inhalation of 1-3% halothane in oxygen and positioned in a stereotaxic frame (Kopf Instruments, Tujunga, Calif.). The incisor bar was adjusted to 5 mm above the interaural line, and the skull exposed. Stainless steel bipolar electrodes (11 mm in length) were implanted into the posterior lateral hypothalamus (AP: −0.5 mm from bregma; ML: ±1.7 mm; DV: 8.3 mm from dura). For the VTA infusion experiment, bilateral stainless steel guide cannulas were implanted 3 mm above the VTA (AP: −3.2 mm from bregma; ML: ±1.7 mm; DV: 5.3 mm from skull surface; angle of 10° from midline), at the same time that ICSS electrodes were implanted. Cannulas were kept patent using 14 mm long stainless steel stylets (30 gauge). Animals were allowed to recover from surgery for at least 7 days prior to training in the ICSS paradigm.

Osmotic Mini-Pump Surgery.

Rats were anaesthetized by inhalation of 1-3% halothane in oxygen and prepared with Alzet osmotic mini-pumps (model 2ML4 (28 day); Alza Corporation, Palo Alto, Calif.) placed subcutaneously (back of the animal parallel to the spine). Pumps were filled with either sterile water or nicotine salt solution. The concentration of the nicotine salt solution was adjusted according to animal body weight, resulting in delivery of 9 mg/kg/day (3.16 mg/kg, free base). This dose of nicotine maintains stable plasma levels (~44 ng/ml) comparable to those obtained in human smokers consuming approximately 30 cigarettes per day (Benowitz, 1988, N Engl J Med 319:1318-1330). Following mini-pump implantation (or removal), the surgical wound was closed with 9 mm stainless steel wound clips and treated with topical antibiotic (Bacitracin) ointment.

Intracranial Self-Stimulation Reward Threshold Procedure

Animals were trained to respond according to a modification of the discrete-trial current-threshold procedure of Kornetsky and Esposito (Fed Proc 38:2473-2476, 1979), which has been described in detail previously (Markou and Koob, 1992 Physiol Behav 51:111-119). Briefly, a trial was initiated by the delivery of a non-contingent electrical stimulus. This electrical reinforcer had a train duration of 500 ms and consisted of 0.1 ms rectangular cathodal pulses that were delivered at a frequency of 50-100 Hz. The current intensity delivered was adjusted for each animal and typically ranged from 50 to 200 µA. A one-quarter wheel turn within 7.5 sec of the delivery of the non-contingent electrical stimulation resulted in the delivery of an electrical stimulus identical in all parameters to the non-contingent stimulus that initiated the trial. After a variable inter-trial interval (7.5-12.5 sec, average of 10 sec), another trial was initiated with the delivery of a non-contingent electrical stimulus. Failure to respond to the non-contingent stimulus within 7.5 sec resulted in the onset of the inter-trial interval. Responding during the inter-trial interval delayed the onset of the next trial by 12.5 sec. Current levels were varied in alternating descending and ascending series. A set of three trials was presented for each current intensity. Current intensities were altered in 5 µA steps. In each testing session, four alternating descending-ascending series were presented. The threshold for each series was defined as the midpoint between two consecutive current intensities that yielded "positive scores" (animals responded for at least two of the three trials) and two consecutive current intensities that yielded "negative scores" (animals did not respond for two or more of the three trials). The overall threshold of the session was defined as the mean of the thresholds for the four individual series. Each testing session was ~30 min in duration. The latency between the onset of the non-contingent stimulus and a positive response was recorded as the response latency. The response latency for each test session was defined as the mean response latency of all trials during which a positive response occurred. After establishment of stable ICSS reward thresholds, rats were tested in the ICSS procedure once daily except for the spontaneous nicotine withdrawal experiment when rats were tested at time-points according to the experimental design.

Intracerebral Injection Procedure

All injections were administered bilaterally in a volume of 0.5 µl/side given over 66 sec through 17 mm injectors. The injectors were connected to calibrated polyethylene-10 tubing preloaded with drug solution and protruded 3 mm below the ends of the cannulas into the VTA. After infusion, the injectors were kept in place for an additional 60 sec to allow for drug diffusion. Injectors were then removed and replaced with 14 mm wire stylets, and the animals then placed directly into the ICSS testing apparatus. Injections were made using a Harvard microinfusion pump (Model 975).

Experimental Design

Systemic administration experiments. These experiments investigated whether nicotine withdrawal, as measured by elevations in ICSS thresholds, could be precipitated in nicotine-treated rats by systemic administration of an agonist at mGluII receptors (LY314582), an agonist at $GABA_B$ receptors (CGP44532), or antagonists at mGlu5 (MPEP), NMDA (MK-801) or AMPA/Kainate (NBQX) glutamate receptors. For each drug tested, rats were trained in the ICSS paradigm until stable baseline responding was achieved, defined as ≦10% variation in thresholds for 3 consecutive days and requiring approximately 14 days of daily testing. In each case, drug-naïve rats were then allocated to two separate groups such that there was no difference in mean baseline ICSS thresholds or body weight between groups. One group was then prepared with subcutaneous osmotic mini-pumps delivering vehicle and the second group with mini-pumps delivering 9 mg/kg/day nicotine hydrogen tartrate (3.16 mg/kg/day nicotine free base). There was a minimum seven-day interval after mini-pump implantation, during which ICSS reward thresholds continued to be measured daily, before the effect of any systemically administered drug on reward thresholds was evaluated. This time period was sufficient to produce robust elevations in thresholds in nicotine-treated but not vehicle-treated rats upon abrupt removal of mini-pumps (i.e. spontaneous withdrawal) or administration of nicotinic receptor antagonists (i.e. precipitated withdrawal) (Malin et al., 1992, Pharmacol Biochem Behav 43:779-784; Malin et. al., 1994, Psychopharmacology 115: 180-184; Hildebrand et al., 1997, Psychopharmacology 129: 348-356; Hildebrand et al., 1999, Neuropsychopharmacology 21:560-574; Epping-Jordan et al., 1998, Nature 393:76-79; Watkins et al., 2000, J Pharmacol Exp Ther 292:1053-1064). Separate groups of nicotine-treated rats and their corresponding nicotine-naïve control group were then injected intraperitoneally with the mGluII receptor agonist LY314582 (0, 2.5, 0.5, 7.5 mg/kg; n=9 nicotine, n=11 control), the $GABA_B$ receptor agonist CGP44532 (0, 0.065, 0.125, 0.25, 0.5 mg/kg; n=5 nicotine, n=5 control), the mGlu5 receptor antagonist MPEP (0, 0.01, 0.05, 0.1 mg/kg; n=8 nicotine, n=7 vehicle or 0, 0.5, 1, 2, 3 mg/kg; n=13 nicotine, n=13 vehicle), the NMDA receptor antagonist MK-801 (0, 0.01, 0.05, 0.1, 0.175, 0.2 mg/kg; n=10 nicotine, n=9 control) or the AMPA/Kainate receptor antagonist NBQX (0, 0.01, 0.025, 0.05, 0.075, 0.1, 0.5, 1 mg/kg; n=10 nicotine, n=12 control) according to a within-subjects Latin square design and ICSS thresholds evaluated 30 min later. A minimum of 48 h were allowed between each injection in the Latin square design, during which ICSS thresholds continued to be measured, to ensure that ICSS thresholds returned to baseline. The doses of LY314582 and MPEP were chosen based on a previous study demonstrating that ≧10 mg/kg LY314582 and ≧3 mg/kg MPEP elevated ICSS thresholds in drug-naïve rats (Harrison et al., 2002, Psychopharmacology 160:56-66). The doses of CGP44532 were chosen based on a previous study demonstrating that ≧0.25 mg/kg elevated ICSS thresholds in drug-naïve rats (Macey et al., 2001, Neuropharmacology 40:676-685). For the potential demonstration of interaction effects it was important to include doses of the test drugs that did not alter thresholds under baseline conditions.

Intra-Ventral Tegmental Area LY314582 Experiment.

After stable baseline ICSS responding was achieved (≦10% variation in threshold for 3 consecutive days), rats (n=15) with bilateral cannulas directed toward the VTA were allocated to two groups such that there were no differences in mean baseline reward thresholds or body weight between groups. One group was then prepared with subcutaneous osmotic mini-pumps delivering vehicle and the second group with mini-pumps delivering nicotine (3.16 mg/kg/day nicotine free base). Animals again were tested in the ICSS paradigm each day for seven days prior to drug treatment. Both groups of rats were then injected directly into the VTA, as described above, with LY314582 (0, 10, 50 and 100 ng/side; n=7 nicotine, n=8 control) according to a within-subjects Latin square design, and ICSS reward thresholds were evaluated immediately post-injection. There was a minimum 48 h interval between each injection, during which ICSS thresholds continued to be measured, to allow thresholds to return to baseline levels before further drug tests. At the conclusion of the experiment, all animals were anaesthetized and their brains removed and immediately placed on ice. The brains were cut in 50 µm sections, and placements of the injectors and the electrodes were examined (see FIG. 1 for histological verification of injection sites). Only those rats with injection tips located within the VTA were included in statistical analyses.

Spontaneous Nicotine Withdrawal Experiment.

Osmotic mini-pumps were surgically removed from nicotine-treated rats (n=15) (defined as rats having been prepared with mini-pumps delivering 3.16 mg/kg/day nicotine freebase for at least seven days) or corresponding control rats (n=17; rats prepared with vehicle-containing mini-pumps). All rats were then tested in the ICSS procedure at 12, 18, 24, 36, 48 and 72 hr after the removal of osmotic mini-pumps. These time points were chosen based on the time course of threshold elevations previously observed during spontaneous nicotine withdrawal after removal of nicotine-delivering osmotic mini-pumps (Harrison et al., 2001, Neuropsychopharmacology 25:55-71; K.L.). Based on the ICSS reward thresholds obtained at the 12 h time-point, nicotine-withdrawing rats were allocated to two groups such that there was no difference in the magnitude of reward threshold elevations between each group (117.67±3.1%, n=8; 119.93±3.5%, n=7). Similarly, control rats were allocated to two groups such that there was no difference in mean reward thresholds between these groups (106.45±5.2%, n=7; 103.63±3.6%, n=10). Thirty min before being tested at the 18 h time-point, one group of nicotine withdrawing and one group of control rats were injected with LY341495 (1 mg/kg); the remaining rats were injected with vehicle.

Statistical Analyses

For all experiments, except the spontaneous nicotine withdrawal experiment, percentage change from baseline reward threshold was calculated by expressing the drug-influenced threshold scores as a percentage of the previous days threshold (i.e. a drug-free baseline threshold). These percentages of baseline scores were subjected to two-factor repeated measures analyses of variance (ANOVA), with treatment drug dose as the within-subjects factor and pump content (nicotine or control) as the between-subjects factor. For the spontaneous nicotine withdrawal experiment, percentage change from baseline reward threshold was calculated by expressing the threshold scores obtained at each time-point during withdrawal as a percentage of thresholds for each rat on the day immediately prior to mini-pump removal. These percentages of baseline scores were subjected to three-factor repeated measures ANOVA. The within-subjects factor was the time after mini-pump removal, and the two between-subjects factors were pump content (nicotine or vehicle) and acute drug treatment (LY314582 or vehicle). For all experiments, response latency data were analyzed in the same manner as the threshold data. After statistically significant effects in the ANOVAs, post-hoc comparisons among means were conducted with the Fisher's LSD test.

Results

Figure 2:
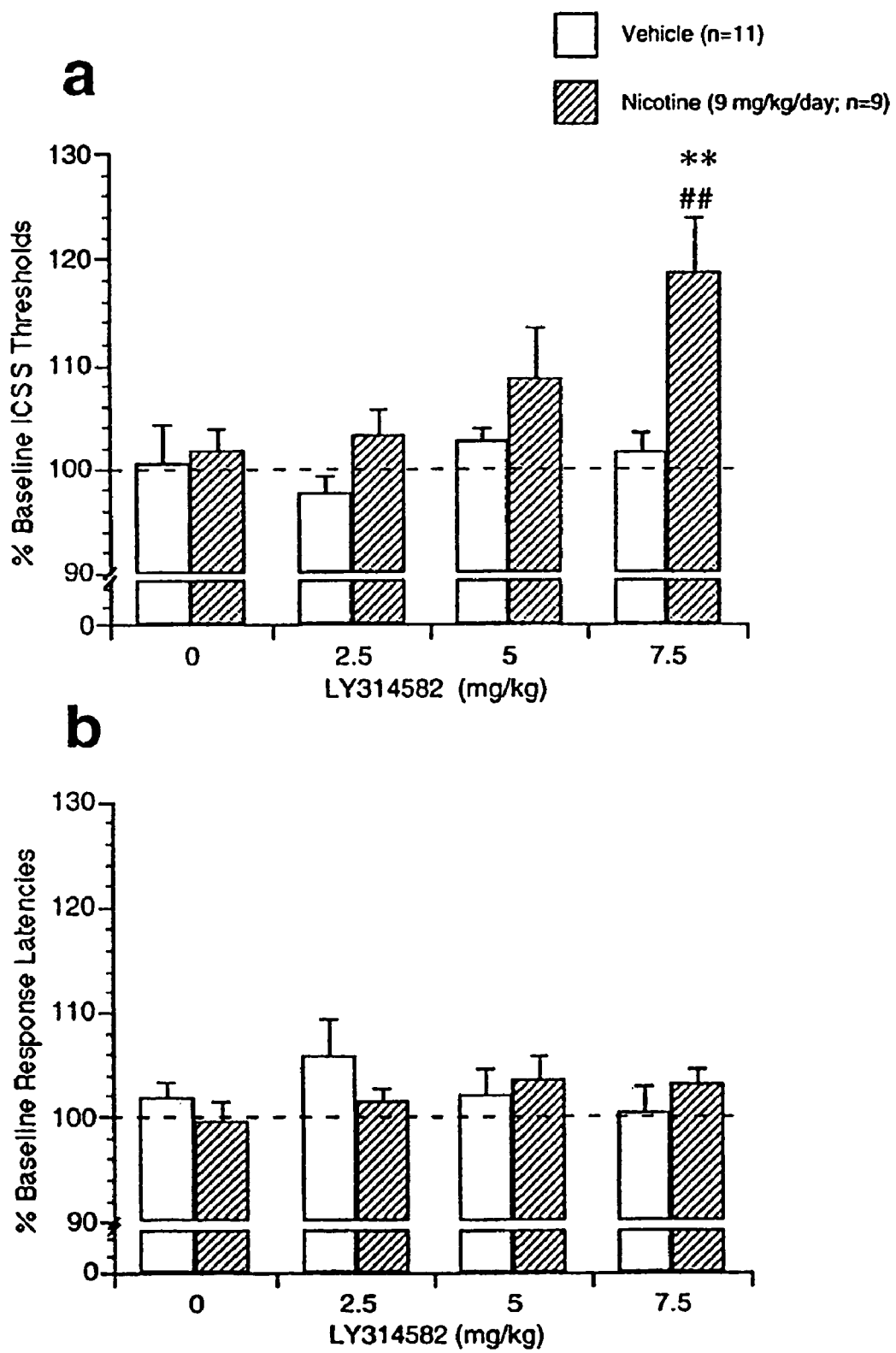
FIGS. 2A-2B illustrate the effects of LY314582 on ICSS thresholds and response latencies in nicotine-treated and control rats.

Intraperitoneal administration of the mGluII receptor agonist LY314582 (2.5-7.5 mg/kg) elevated ICSS reward thresholds in nicotine-treated but not control rats. This effect was reflected in a statistically significant effect of group ($F_{(1,18)}$=7.43, p<0.05), a significant effect of dose ($F_{(3,54)}$=5.02, p<0.005), and a significant group×dose interaction ($F_{(3,54)}$=2.79, p<0.05). Post-hoc analysis revealed that the highest dose of LY314582 (7.5 mg/kg) elevated reward thresholds in nicotine-treated rats compared to vehicle treatment (p<0.01), and compared to control rats tested with the same dose (p<0.01) (FIG. 2A). In contrast to its effects on reward thresholds, LY314582 had no effect on response latencies in nicotine-treated or control rats ($F_{(3,54)}$=0.59, NS) at any dose tested (FIG. 2B).

As shown in Table 1, the selective $GABA_B$ receptor agonist CGP44532 did not precipitate reward threshold elevations in nicotine treated rats at the lowest doses tested (0.065-0.25 mg/kg), whereas at the highest dose tested, CGP44532 (0.5 mg/kg) elevated reward thresholds in nicotine-treated and control rats ($F_{(4,32)}$=16.62, p<0.001). There was no difference in the effects of CGP44532 in nicotine-treated compared to control rats (group×dose interaction: $F_{(4,32)}$=0.05, NS). CGP44532 also had no effect on response latencies at any dose tested ($F_{(4,32)}$=0.30, NS).

TABLE 1

Effects of the $GABA_B$ receptor agonist CGP44532 on ICSS thresholds and response latencies in nicotine- and vehicle-treated rats

| CGP44532 (mg/kg) | Vehicle | | Nicotine | |
|---|---|---|---|---|
| | Thresholds n = 5 | Latencies | Thresholds n = 5 | Latencies |
| 0 | 96.79 ± 2.8 | 95.51 ± 2.2 | 99.93 ± 4.1 | 100.31 ± 4.6 |
| 0.065 | 96.28 ± 3.1 | 97.31 ± 3.8 | 96.37 ± 3.2 | 106.02 ± 8.1 |
| 0.125 | 106.76 ± 3.2 | 102.34 ± 2.8 | 103.88 ± 7.2 | 98.15 ± 5.3 |
| 0.25 | 109.14 ± 5.1 | 105.03 ± 3.1 | 109.98 ± 5.4 | 99.05 ± 3.1 |
| 0.5 | 148.43 ± 16.6*** | 106.13 ± 6.5 | 146.83 ± 14.3*** | 98.11 ± 5.4 |

Data (mean ± SEM) are expressed as percentage of baseline ICSS threshold and response latency.
Asterisks indicate statistically significant differences between CGP44532 and vehicle treatment.
***P < 0.001 after significant two-way ANOVA with repeated measures.

Figure 3:
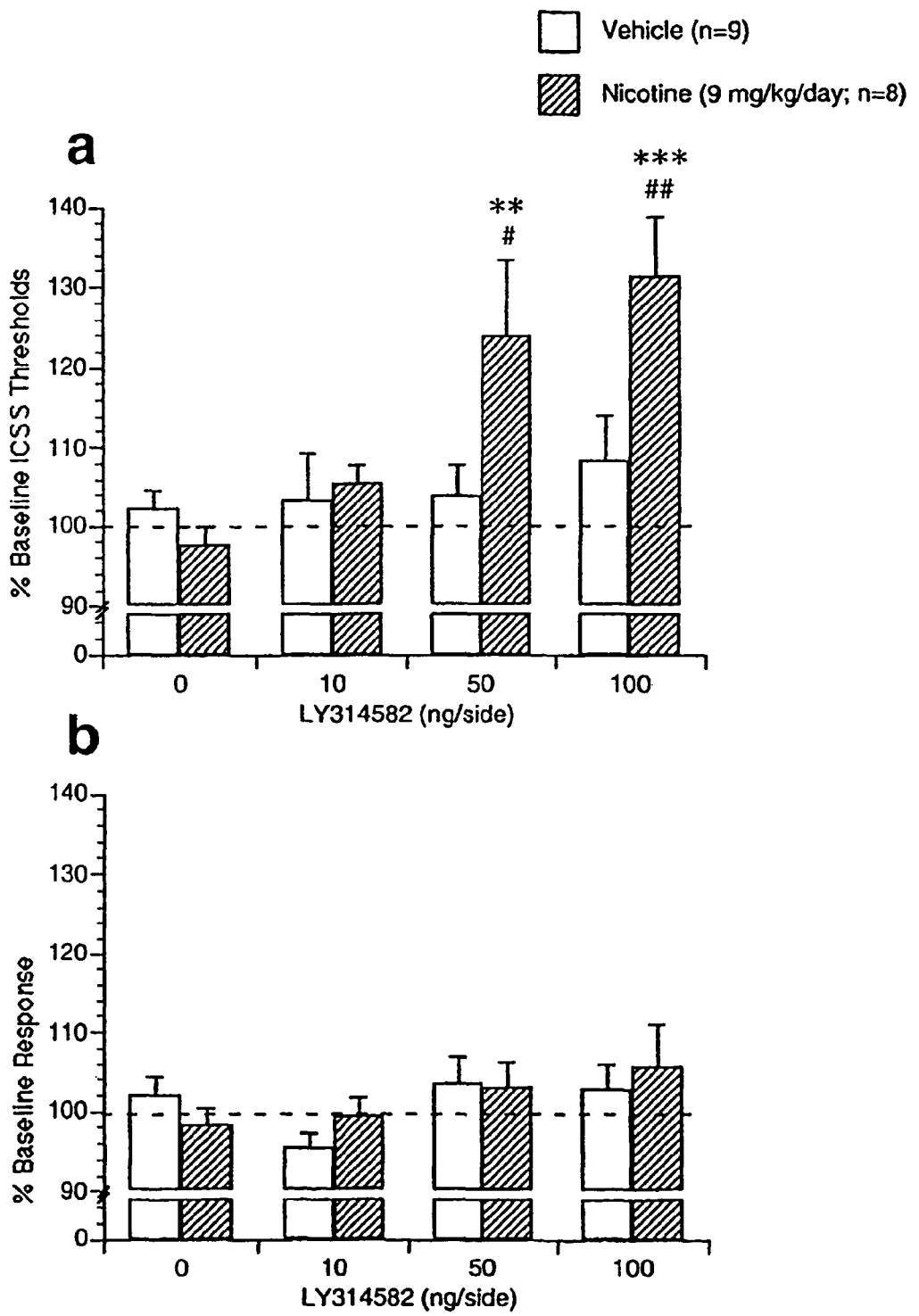
FIGS. 3A-3B illustrate the effects of intra-ventral tegmental area LY314582 on ICSS thresholds and response latencies in nicotine-treated and control rats.

As shown in FIG. 3, bilateral microinfusion of LY314582 (10-100 ng/side) directly into the VTA significantly elevated reward thresholds in nicotine-treated but not control rats. Again there were significant effects of group ($F_{(1,13)}$=4.81, p<0.05), dose ($F_{(3,39)}$=4.77, p<0.01), and a significant group×dose interaction ($F_{(3,39)}$=3.82, p<0.05). Post-hoc analyses revealed that doses of 50 and 100 ng/side LY314582 were sufficient to elevate reward thresholds in nicotine-treated rats without affecting thresholds in control rats. LY314582 had no effect on response latencies ($F_{(3,39)}$=1.94, NS) in nicotine-treated or control rats after VTA administration (FIG. 3B).

Figure 4:
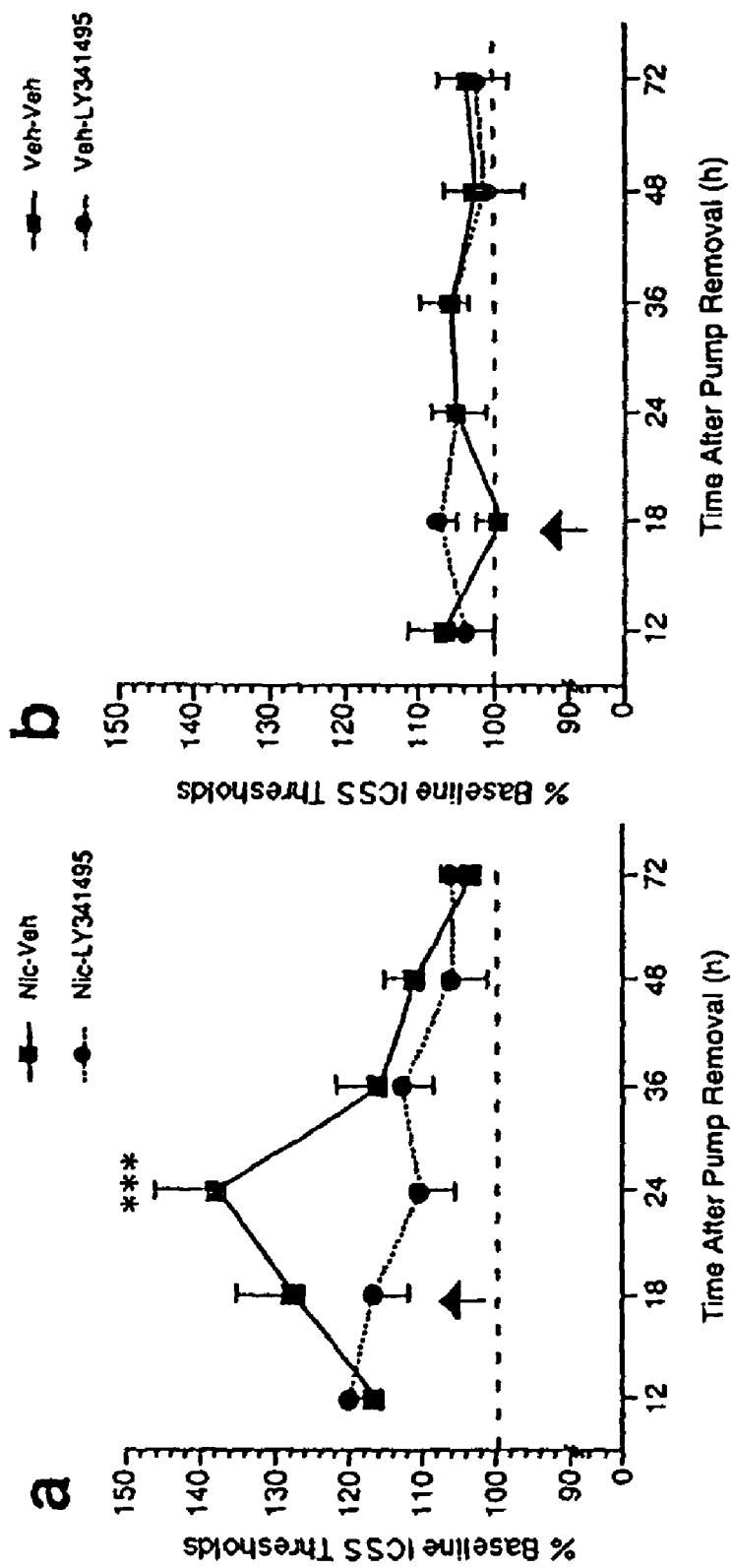
FIGS. 4A-4B illustrate the effects of LY341495 on the elevations in ICSS thresholds in rats undergoing spontaneous nicotine withdrawal.

As shown in FIG. 4, withdrawal from chronic nicotine treatment produced robust ICSS threshold elevations compared to control rats ($F_{(1,27)}$=15.3, p=0.0006). Analysis of the significant group×dose×time interaction ($F_{(5,135)}$=3.3, p=0.01) revealed the following: Nicotine-treated rats injected with vehicle demonstrated robust reward threshold elevations that reached a peak 24 h following mini-pump removal (FIG. 4A). However, administration of LY341495 30 min before the 18 h time-point significantly attenuated the elevations in reward thresholds in nicotine-withdrawing rats (p<0.001) (see FIG. 4A), without affecting thresholds in control rats (FIG. 4B). LY341495 had no effect on response latencies at any time-point after injection ($F_{(1,27)}$=0.43, NS).

As illustrated in Table 2, MK-801 (dizocilpine) (0.01-0.2 mg/kg) lowered reward thresholds in nicotine-treated and control rats ($F_{(6,66)}$=7.5, p<0.0001).

TABLE 2

Effects of the NMDA receptor antagonist MK-801 on ICSS thresholds and response latencies in nicotine- and vehicle-treated rats

| MK-801 (mg/kg) | Vehicle | | Nicotine | |
|---|---|---|---|---|
| | Thresholds | Latencies | Thresholds | Latencies |
| | n = 9 | | n = 10 | |
| 0 | 102.72 ± 3.9 | 99.04 ± 1.7 | 103.65 ± 1.7 | 93.73 ± 2.7 |
| 0.01 | 95.99 ± 3.3 | 100.00 ± 2.5 | 98.20 ± 6.1 | 95.41 ± 2.3 |
| 0.03 | 92.54 ± 2.6 | 103.14 ± 2.1 | 93.09 ± 3.9 | 94.64 ± 3.6 |
| 0.1 | 88.48 ± 5.6** | 98.97 ± 3.9 | 89.42 ± 3.6 | 106.14 ± 4.4 |
| 0.15 | 87.14 ± 4.6** | 101.60 ± 2.0 | 76.24 ± 4.7*** | 93.65 ± 3.6 |
| 0.175 | 93.64 ± 3.4* | 119.22 ± 11.9** | 82.26 ± 3.7** | 93.56 ± 4.2 |
| 0.2 | 82.47 ± 4.3*** | 119.21 ± 9.4** | 84.29 ± 3.0* | 105.14 ± 1.9 |

Data (mean ± SEM) are expressed as percentage of baseline ICSS threshold and response latency.
Asterisks indicate statistically significant differences between MK-801 and vehicle treatment.
*P < 0.05,
**p < 0.01,
***p < 0.001 after significant two-way ANOVA with repeated measures.

MK-801 lowered reward thresholds by a similar magnitude in nicotine-treated and control rats and there was no group× dose interaction ($F_{(6,66)}=1.2$, NS). Doses of MK-801 ≧0.2 mg/kg caused disruption in performance in the ICSS paradigm in both groups such that rats no longer responded for self-stimulation, and therefore doses higher than 0.2 mg/kg were not tested. Further, MK-801 did not precipitate withdrawal-like elevations in reward thresholds in nicotine-treated rats at any dose tested. MK-801 did significantly increase response latencies ($F_{(6,72)}=2.9$, p<0.05). Post-hoc analysis demonstrated that as the dose of MK-801 increased so too did response latency, particularly in control rats, suggesting that performance was increasingly impaired at higher doses of MK-801.

As shown in Table 3, low doses of MPEP (0.01-0.1 mg/kg) did not affect reward thresholds ($F_{(3,39)}=2.3$, NS) or response latencies ($F_{(3,39)}=0.4$, NS) in nicotine-treated or control rats. Higher doses of MPEP (0.5-3 mg/kg) elevated reward thresholds in nicotine-treated and control rats ($F_{(4,96)}=8.4$, P<0.0001). However, MPEP elevated ICSS thresholds in both groups of rats by a similar magnitude, and there was no group×dose interaction ($F_{(4,96)}=0.7$, NS). MPEP (0.5-3 mg/kg) had no effect on response latencies ($F_{(4,96)}=1.4$, NS) in either group.

TABLE 3

Effects of the mGlu5 receptor antagonist MPEP on ICSS thresholds and response latencies in nicotine- and vehicle-treated rats

| MPEP (mg/kg) | Vehicle | | Nicotine | |
|---|---|---|---|---|
| | Thresholds | Latencies | Thresholds | Latencies |
| | n = 7 | | n = 8 | |
| 0 | 97.67 ± 2.0 | 104.78 ± 1.1 | 95.68 ± 3.5 | 101.79 ± 5.2 |
| 0.01 | 98.75 ± 3.5 | 99.75 ± 3.4 | 93.86 ± 6.0 | 101.50 ± 2.2 |
| 0.05 | 101.27 ± 4.1 | 104.87 ± 3.3 | 94.11 ± 2.6 | 103.48 ± 4.2 |
| 0.1 | 105.13 ± 3.2 | 105.13 ± 4.8 | 103.84 ± 1.2 | 102.54 ± 1.5 |
| | n = 13 | | n = 13 | |
| 0 | 99.91 ± 1.8 | 99.41 ± 1.9 | 100.62 ± 3.3 | 100.76 ± 2.3 |
| 0.5 | 103.01 ± 2.7 | 103.20 ± 4.4 | 104.02 ± 2.2 | 99.47 ± 1.9 |
| 1 | 103.70 ± 3.0 | 100.72 ± 2.1 | 105.81 ± 3.3 | 99.12 ± 1.7 |
| 2 | 111.21 ± 2.3** | 107.60 ± 2.6 | 121.17 ± 6.2** | 101.31 ± 2.2 |
| 3 | 111.52 ± 4.8** | 103.58 ± 2.3 | 119.11 ± 5.5** | 102.22 ± 3.6 |

Data (mean ± SEM) are expressed as percentage of baseline ICSS threshold and response latency.
Asterisks indicate statistically significant differences between MPEP and vehicle treatment.
**P < 0.01 after significant two-way ANOVA with repeated measures.

Figure 5:
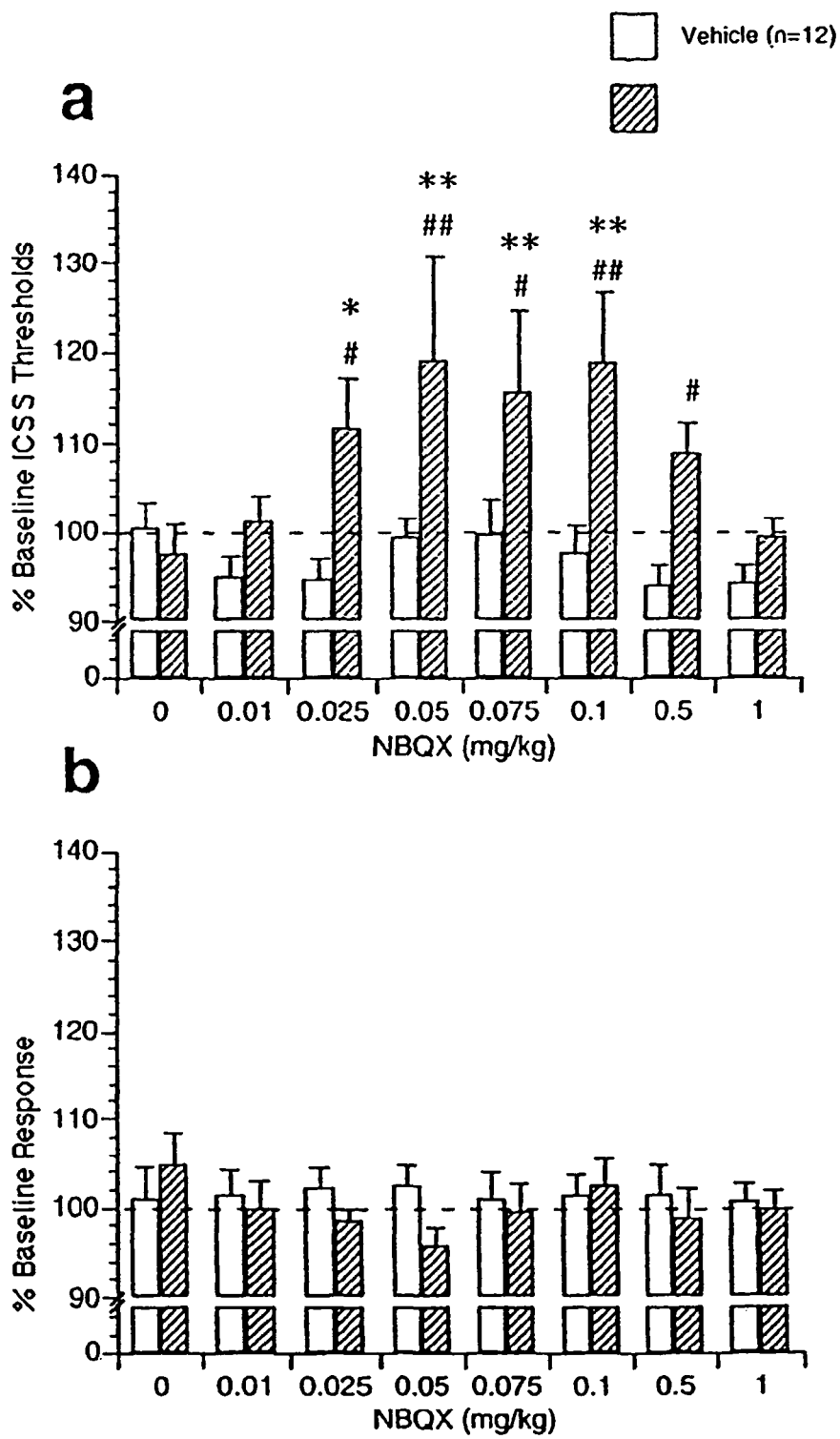
FIG. 5 illustrates the effects of NBQX on ICSS thresholds and response latencies in nicotine-treated and control rats. A, Data are expressed as mean (±SEM) percentage change from baseline threshold. B, Data are expressed as mean (±SEM) percentage change from baseline response latency. *P<0.05, **p<0.01, different from nicotine-treated rats after vehicle injection. #P<0.05, ##p<0.01, different from control rats after injection with same dose of NBQX.

As illustrated in FIG. 5, the AMPA/Kainate receptor antagonist NBQX (0.01-1 mg/kg) significantly altered ICSS reward thresholds in nicotine-treated but not control rats. This effect was reflected in a statistically significant effect of group ($F_{(1,20)}=10.82$, p<0.005), a significant effect of dose ($F_{(7,140)}=2.8$, p<0.01), and a significant group×dose interaction ($F_{(7,140)}=2.11$, p<0.05). Post-hoc analysis revealed a bimodal action of NBQX on reward thresholds in nicotine-treated rats. Low doses of NBQX (0.025-0.1 mg/kg) elevated reward thresholds in nicotine-treated rats, whereas higher doses of NBQX (0.5-1 mg/kg) were less effective and did not significantly increase thresholds compared to vehicle treatment (FIG. 5A). NBQX had no effect on response latencies in nicotine-treated or control rats at any dose tested ($F_{(7,140)}=0.31$, NS) (FIG. 5B).

The present data provide strong evidence for a role of Group II metabotropic glutamate receptors in regulating the deficit in brain reward function associated with nicotine withdrawal by demonstrating that activation of mGluII receptors precipitated reward deficits in nicotine-treated rats similar to those observed during nicotine withdrawal. Further, activation of mGluII receptors located within the VTA also precipitated withdrawal-like reward deficits in nicotine treated rats, providing further evidence for an important role of the VTA in mediating the actions of nicotine on the brain's reward pathway (Hildebrand et al., 1999; Mansvelder and McGehee, 2000; Mansvelder et al., 2002). Finally, blockade of mGluII receptors attenuated the deficit in brain reward function observed in rats undergoing spontaneous nicotine withdrawal. Previously, the mGluII receptor agonist LY354740 was shown to attenuate the increased auditory startle observed during spontaneous nicotine withdrawal (Helton et al., 1997). One possible explanation for these observations is that mGluII receptors located in different brain sites may differentially regulate various aspects of nicotine withdrawal.

Discussion

The present invention is based on the experimental results presented in the Examples, related to the role and possible mechanisms of action of mGluII and $GABA_B$ receptors in mediating the reward deficits associated with nicotine withdrawal. Systemic administration of the selective mGluII receptor agonist LY314582 (2.5-7.5 mg/kg), but not the $GABA_B$ receptor agonist CGP44532 (0.065-0.5 mg/kg), precipitated withdrawal-like elevations in intracranial self-stimulation (ICSS) reward thresholds, a sensitive measure of reward function, in nicotine-dependent but not control rats. LY314582 did not affect response latencies, a measure of performance in the ICSS paradigm. Bilateral microinfusion of LY314582 (10-100 ng/side) into the ventral tegmental area (VTA) likewise precipitated threshold elevations in nicotine-dependent but not control rats. Further, a single injection of the mGluII receptor antagonist LY341495 (1 mg/kg) attenuated the elevations in reward thresholds in rats undergoing spontaneous nicotine withdrawal. Finally, because activation of mGluII receptors decreases glutamate transmission, it was hypothesized that blockade of postsynaptic glutamate receptors would also precipitate withdrawal-like reward deficits in nicotine-dependent rats. Accordingly, NBQX (0.001-1 mg/kg), a selective AMPA/Kainate ($\alpha$-amino-3-hydroxy-5-methyl-4-isoxazole propionate/kainate) receptor antagonist, precipitated withdrawal-like elevations in ICSS thresholds in nicotine-dependent but not control rats, whereas MPEP (0.01-3 mg/kg) and MK-801 (0.01-0.125 mg/kg), antagonists at mGlu5 (metabotropic glutamate5) and NMDA (N-methyl-D-aspartate) receptors respectively, did not. Overall, these data demonstrate that inhibitory regulation of brain reward function by mGluII receptors located in the VTA was increased in nicotine-dependent rats, which contributed to the reward deficits associated with nicotine withdrawal. Further, it is likely that decreased glutamate transmission at AMPA/Kainate receptors also contributed to nicotine withdrawal-induced reward deficits.

Not to be limited by theory, the present invention is based in part on the following considerations. There is now compelling evidence that the aversive syndrome observed during periods of nicotine abstinence contributes to tobacco addiction (Kenny and Markou, 2001, Pharmacol Biochem Behav 70:531-549). Indeed, nicotine withdrawal recently was shown to precipitate a deficit in brain reward function, as measured by elevations in intracranial self-stimulation (ICSS) reward thresholds, similar in magnitude and duration to that observed in rats undergoing withdrawal from other major drugs of abuse (Epping-Jordan et al., 1998 Nature 393:76-79; Harrison et al., 2001 Neuropsychopharmacology 25:55-71). Moreover, this deficit in brain reward function has been proposed as a major motivational factor contributing to craving, relapse and continued tobacco consumption in human smokers (Epping-Jordan et al., 1998). However, in contrast to the intense investigation into the mechanisms by which nicotine produces its rewarding effects (see Picciotto and Corrigall, 2002 J Neurosci 22:3338-3341), little is known regarding the mechanisms mediating the reward deficits associated with nicotine withdrawal.

A common feature of drugs of abuse including nicotine is their ability to increase dopamine transmission in the mesoaccumbens reward pathway and thereby facilitate brain reward function (Pontieri et al., 1996; Picciotto, 1998; Di Chiara, 2000). Nicotine is thought to achieve this, in part, by activation of excitatory glutamate transmission in the VTA (Schilström et al., 1998; Mansvelder and McGehee, 2000; Mansvelder et al., 2002). Therefore, because mGluII receptors located in the VTA are presynaptic autoreceptors that decrease glutamate transmission (Bonci et al., 1997; Wigmore and Lacey, 1998; Manzoni and Williams, 1999), it is likely that the increased sensitivity of mGluII receptors located in the VTA in nicotine-treated rats occurred in response to a pattern of prolonged activation of excitatory glutamate transmission by nicotine in this brain site.

During nicotine withdrawal, when the stimulatory effects of nicotine on excitatory glutamate transmission were no longer present, increased mGluII receptor function in the VTA would be expected to decrease glutamate transmission and thereby decrease the activity of the brain's reward system. Electrophysiological and in vivo microdialysis studies are consistent with this hypothesis. For instance, Manzoni and Williams (1999) demonstrated that prolonged opiate treatment increased the inhibitory effects of mGluII receptor agonists on excitatory glutamate currents in VTA dopamine neurons. Similarly, repeated cocaine treatment increased the content and dimerization of mGluII receptors in the NAcc, and thereby increased the inhibitory effects of mGluII receptors on glutamate efflux in this brain site (Xi et al., 2001). It is interesting to note that similar studies also documented an increase in $GABA_B$ receptor function in the VTA after repeated treatment with opiates and amphetamine (Manzoni and Williams, 1999; Giorgetti et al., 2002). However, we found that regulation of brain reward function by $GABA_B$ receptors was unchanged in nicotine-treated rats compared to controls, suggesting that $GABA_B$ receptors are probably not involved in mediating the reward deficits associated with nicotine withdrawal.

Previous studies have found that the mGluII receptor agonist LY354740 ameliorated the increased auditory startle response in rats undergoing spontaneous nicotine withdrawal (Helton et al., 1997). Similarly, agonists at mGluII receptors decreased physical signs of abstinence in rats undergoing opiate withdrawal (Fundytus and Coderre, 1997; Vandergriff and Rasmussen, 1999). These observations may appear at variance with the data presented here in which systemic and intra-VTA administration of a selective mGluII receptor agonist precipitated withdrawal-like reward deficits in nicotine-treated rats and blockade of these receptors reversed spontaneous nicotine withdrawal.

However, there is accumulating evidence for a differential role of glutamate transmission in various aspects of drug withdrawal. For example, increased glutamate transmission, particularly in the locus coeruleus (LC) and amygdala (Zhang et al., 1994; Rasmussen, 1995; Taylor et al., 1997), is thought to play an important role in the expression of 'somatic' aspects of the opiate withdrawal syndrome, whereas decreased glutamate transmission in the mesoaccumbens reward system is thought to contribute to the reward and motivational deficits manifest during withdrawal from opiates and other drugs of abuse (Keys et al., 1998; Lu and Wolf, 1999; Manzoni and Williams, 1999; Giorgetti et al., 2002). Indeed, Shaw-Lutchman and colleagues (2002) recently demonstrated that cAMP response element (CRE)-mediated transcription, a marker of cellular activity, was increased in the LC and amygdala and decreased in the VTA in rats undergoing precipitated morphine withdrawal, suggesting that the activity of these site was altered in opposite directions during morphine withdrawal. Based on these observations, it is likely that a similar dissociation exists also for the role of glutamate in mediating different aspects of nicotine withdrawal. However, it is worth noting that affective aspects of drug withdrawal, and in particular the deficit in brain reward function, are considered more important in the maintenance of dependence to drugs compared to other symptoms of drug withdrawal (Markou et al., 1998; Kenny and Markou, 2001; Ahmed et al., 2002).

Glutamate transmission regulates the excitability of mesoaccumbens dopamine neurons, and plays an essential role in mediating baseline activity of reward pathways (Kalivas and Stewart, 1991; Suaud-Chagny et al., 1992; Kalivas, 1993). As described above, mGluII receptors act as presynaptic autoreceptors in the VTA where they depress glutamate transmission. Therefore, it was hypothesized that mGluII receptors elevated reward thresholds in nicotine-withdrawing rats, at least in part, by decreasing glutamate transmission and that blockade of glutamate transmission at postsynaptic glutamate receptors would precipitate reward threshold elevations in nicotine-treated rats similar to those in rats undergoing spontaneous nicotine withdrawal.

Accordingly, at low doses the AMPA/Kainate receptor antagonist NBQX precipitated elevations in reward thresholds in nicotine-treated but not control rats. This observation suggests that decreased glutamate transmission at AMPA/Kainate receptors contributes to the reward deficits associated with nicotine withdrawal. These data are also consistent with recent findings demonstrating that prolonged nicotine treatment decreased AMPA receptor immunoreactivity in the NAcc and VTA (Lee et al., 2001). Under normal conditions, AMPA/Kainate receptors are the primary regulators of excitatory glutamate transmission throughout the mesoaccumbens reward pathway (Pennartz et al., 1990; Hu and White, 1996). Therefore, similar to an increase in mGluII receptor function, decreased AMPA receptor expression in nicotine-treated rats would be expected to decrease mesoaccumbens dopamine transmission and thereby act to counter the prolonged stimulatory effects of nicotine on this system.

Curiously, blockade of NMDA receptors in nicotine-treated rats did not precipitate reward threshold elevations, but instead lowered thresholds, reflecting a rewarding action in both nicotine-treated and control rats. There is considerable evidence that NMDA receptors play a crucial role in mediating the stimulatory effects of nicotine on mesoaccumbens dopamine transmission (Schilström et al., 1998; Fu et al., 2000; Mansvelder and McGehee, 2000). Therefore, it might have been expected that by blocking nicotine's stimulatory effects on reward pathways by antagonizing NMDA receptors, the counter-adaptive processes that occurred during prolonged nicotine treatment, such as increased sensitivity of mGluII receptors, would have given rise to elevations in ICSS thresholds.

One explanation for these data is that many populations of NMDA receptors exist throughout the brain's reward circuitries, potentially with opposite actions on brain reward function. Indeed, antagonists at NMDA receptors are by themselves rewarding and have been shown to lower ICSS thresholds after direct intra-VTA administration (David et al., 1998). Blockade of mGlu5 receptors also did not precipitate nicotine withdrawal, but instead elevated ICSS thresholds in control and nicotine-treated rats. These data demonstrate that mGlu5 receptor blockade decreases brain reward function to a similar extent in both groups of rats.

REFERENCES CITED IN EXAMPLE 1

Ahmed S H, Kenny P J, Koob G F, Markou A (2002), Nat Neurosci 5:625-626.
Benowitz N L (1988), N Engl J Med 319:1318-1330.
Bonci A, Grillner P, Siniscalchi A, Mercuri N B, Bernardi G (1997), Eur J Neurosci 9:2359-2369.
Cartmell J, Schoepp D D (2000), J Neurochem 75:889-907.
Chiamulera C, Epping-Jordan M P, Zocchi A, Marcon C, Cottiny C, Tacconi S, Corsi M, Orzi F, Conquet F (2001), Nat Neurosci 4:873-874.
David V, Durkin T P, Cazala P (1998), Eur J Neurosci 10:1394-1402.
Di Chiara G (2000), Eur J Pharmacol 393:295-314.
Epping-Jordan M P, Watkins S S, Koob G F, Markou A (1998), Nature 393:76-79.
Erhardt S, Mathe J M, Chergui K, Engberg G, Svensson T H (2002), Naunyn Schmiedebergs Arch Pharmacol 365:173-180.
Fu Y, Matta S G, Gao W, Brower V G, Sharp B M (2000), J Pharmacol Exp Ther 294:458-465.
Fundytus M E, Coderre T J (1997), Br J Pharmacol 121:511-514.
Giorgetti M, Hotsenpiller G, Froestl W, Wolf M E (2002), Neuroscience 109:585-595.
Harrison A A, Liem Y T, Markou A (2001), Neuropsychopharmacology 25:55-71.
Harrison M, Gasparini F, Markou A (2002), Psychopharmacology 160:56-66.
Helton D R, Tizzano J P, Monn J A, Schoepp D D, Kallman M J (1997), Neuropharmacology 36:1511-1516.
Hildebrand B E, Nomikos G G, Bondjers C, Nisell M, Svensson T H (1997), Psychopharmacology 129:348-356.
Hildebrand B E, Panagis G, Svensson T H, Nomikos G G (1999), Neuropsychopharmacology 21:560-574.
Hu X T, White F J (1996), Synapse 23:208-218.
Kalivas P W (1993), Brain Res Brain Res Rev 18:75-113.
Kalivas P W, Stewart J (1991), Brain Res Brain Res Rev 16:223-244.
Kenny P J, Markou A (2001), Pharmacol Biochem Behav 70:531-549.
Keys A S, Mark G P, Emre N, Meshul C K (1998), Synapse 30:393-401.
Kornetsky C, Esposito R U (1979), Fed Proc 38:2473-2476.
Lee K J, Kim D H, Shim I S, Choi S H, Min B H, Chun B G, Shin K H (2001), Soc Neurosci Abstr 27: 599.
Lu W, Wolf M E (1999), Synapse 32:119-131.
Macey D J, Froestl W, Koob G F, Markou A (2001), Neuropharmacology 40:676-685.
Malin D H, Lake J R, Newlin-Maultsby P, Roberts L K, Lanier J G, Carter V A, Cunningham J S, Wilson O B (1992), Pharmacol Biochem Behav 43:779-784.
Malin D H, Lake J R, Carter V A, Cunningham J S, Hebert K M, Conrad D L, Wilson O B (1994), Psychopharmacology 115:180-184
Mansvelder H D, McGehee D S (2000), Neuron 27:349-357.
Mansvelder H D, Keath J R, McGehee D S (2002), Neuron 33:905-919.
Manzoni O J, Williams J T (1999), J Neurosci 19:6629-6636.
Markou A, Koob G F (1992), Physiol Behav 51:111-119.
Markou A, Kosten T R, Koob G F (1998), Neuropsychopharmacology 18:135-174.
Paxinos G, Watson C H (1986) The rat brain in stereotaxic coordinates. London Academic Press, London, UK.
Pennartz C M, Boeijinga P H, Lopes da Silva F H (1990), Brain Res 529:30-41.
Piccioto M R (1998), Drug Alcohol Depend 51:165-172.
Picciotto M R, Corrigall W A (2002), J Neurosci 22:3338-3341.
Pontieri F E, Tanda G, Orzi F, Di Chiara G (1996), Nature 382:255-257.

Rasmussen K (1995), Neuropsychopharmacology 13:295-300.
Schilström B, Nomikos G G, Nisell M, Hertel P, Svensson T H (1998), Neuroscience 82:781-789.
Schoepp D D (2001), J Pharmacol Exp Ther 299:12-20.
Shaw-Lutchman T Z, Barrot M, Wallace T, Gilden L, Zachariou V, Impey S, Duman R S, Storm D, Nestler E J (2002), J Neurosci. 22:3663-3672.
Suaud-Chagny M F, Chergui K, Chouvet G, Gonon F (1992), Neuroscience 49:63-72.
Taylor J R, Punch L J, Elsworth J D (1997), Psychopharmacology 138:133-142.
Vandergriff J, Rasmussen K (1999), Neuropharmacology 38:217-222.
Watkins S S, Stinus L, Koob G F, Markou A (2000), J Pharmacol Exp Ther 292:1053-1064.
Wigmore M A, Lacey M G (1998), Br J Pharmacol 123:667-674.
Xi Z, Baker D A, Shen H; Carson D S, Kalivas P W (2002), J Pharmacol Exp Ther 300:162-171.
Xi Z, Shen H, Carson D, Baker D A, Kalivas P W (2001), Soc Neurosci Abstr 27: 2596.
Zhang T, Feng Y, Rockhold R W, Ho I K (1994), Life Sci 55:PL25-PL31.

Example 2

The mGluR5 Antagonist MPEP Decreases Nicotine Self-Administration in Rats and Mice This example illustrates that blockade of mGluR5 decreases nicotine self-administration in both rats and mice, and are consistent with findings showing a role of mGluR5 in cocaine self-administration. Nicotine self-administration by rats is thought to reflect the rewarding effects of nicotine, and has been shown to be sensitive to modulation of dopaminergic (Corrigall & Coen 1991; Picciotto and Corrigall 2002), cholinergic (Watkins et al. 1999; Corrigall et al. 2002; Picciotto and Corrigall 2002) and K-amino-butyric acid (GABA)-ergic (Dewey et al. 1999; Paterson and Markou 2002; Picciotto and Corrigall 2002) neurotransmission. Additional work has suggested a possible role for glutamate in mediating the rewarding effects of nicotine (McGehee et al. 1995; Schilstrom et al. 2000; Reid et al. 2000). Specifically, neurochemical studies indicated that systemic nicotine administration resulted in significant increases in glutamate levels in the ventral tegmental area (VTA) and the nucleus accumbens (NAcc) (Reid et al. 2000; Schilstrom et al. 2000). Further, a recent electrophysiological study by Mansvelder and colleagues (2002) indicated a complex interaction between GABA-ergic and glutamatergic inputs to midbrain dopamine neurons at the level of the VTA in slices exposed to nicotine levels of similar concentration and duration as those experienced in smoker's brains. In summary, nicotine is thought to exert its rewarding effects by complex interactions of multiple neurotransmitters in the central nervous system. Chief amongst these is the mesolimbic dopaminergic system, although recently glutamate also has been shown to play an important role.

The eight subtypes of metabotropic glutamate receptors (mGluR) are divided into three groups, based on amino acid sequence homology, second messenger systems and pharmacology (Conn and Pin 1997). The Group I mGluRs comprise metabotropic glutamate receptor subtype 5 (mGluR5) and mGluR1, and act via stimulation of phospholipase C (Conn and Piri 1997). The distribution of mGluR5s has been characterized in detail, indicating heavy distribution in the NAcc, striatum and hippocampus in the rat brain (Shigemoto et al. 1993; Tallakssen-Greene et al. 1998). Metabotropic glutamate receptors have been shown to be involved in the modulation of neurotransmitter release (Cartmell and Schoepp 2000; Schoepp 2001), synaptic plasticity and learning (Holscher et al. 2001), neuroprotection (Battaglia et al. 2001, 2002), dopamine-dependent locomotor behaviors (for review, see Vezina and Kim 1999) and pain (for review, see Spooren et al. 2001).

Recently, and most relevant to the present study, it has been shown that mice lacking mGluR5 will not acquire intravenous cocaine self-administration (Chiamulera et al. 2001). In addition, administration of the specific mGluR5 antagonist 2-methyl-6-(phenylethynyl)-pyridine (MPEP; Gasparini et al. 1999) resulted in a dose-dependent reduction in cocaine self-administration without affecting responding for food (Chiamulera et al. 2001). Furthermore, it has been shown that repeated cocaine administration over one week resulted in significantly increased levels of mGluR5 mRNA expression in the nucleus accumbens shell and dorsal striatum that persisted for three weeks after the cessation of cocaine administration (Ghasemzadeh et al. 1999). In addition to cocaine self-administration, MPEP has been shown to have several effects in a variety of behavioral paradigms in laboratory animals. Previous work indicated that administration of MPEP in rodents has significant anxiolytic- and antidepressant-like effects (Spooren et al. 2000b; Tatarczynska et al. 2001). In addition, MPEP was shown to block fear conditioning (Schulz et al. 2001), exert anti-Parkinsonian-like effects (Ossowska et al. 2001; Breysse et al. 2002), and have anti-convulsant activity (Chapman et al. 2000) in rodents. In summary, MPEP has been shown to have a wide variety of effects in a number of different behavioral paradigms in rodents, and the mGluR5 has been shown to be involved in cocaine self-administration and possibly longer-term effects of cocaine.

Based on previous findings summarized above indicating a role of mGluR5 receptors in mediating the rewarding effects of cocaine (Chiamulera et al., 2001), and also the role of glutamate in mediating the rewarding effects of nicotine, the present study set out to determine the effects of MPEP on the reinforcing effects of intravenous nicotine in rats that regularly self-administer nicotine at one of two doses (0.03 and 0.01 mg/kg/infusion), and in drug-naive mice. In addition, the effect of MPEP administration on food-maintained responding in rats was investigated to determine the specificity of the effects of MPEP. Further, the mouse self-administration procedure used here includes yoked control mice that allow the assessment of non-specific effects of pharmacological manipulations.

Materials and Methods

Subjects

Male Wistar rats (Charles River, Raleigh, N.C.) weighing 300-350 g upon arrival in the laboratory were group housed (two per cage) in a temperature- and humidity-controlled vivarium on a 12 hr reverse light-dark cycle (lights on at 10 am) with unrestricted access to water except during testing, and food-restricted to 20 g/day after acquiring nicotine self-administration behavior. Male DBA/2J mice (Harlan Laboratories, Indianapolis, Ind.) at the age of 10-12 weeks upon arrival in the laboratory were group housed (4 per cage) in a temperature- and humidity-controlled vivarium on a 12 hr reverse light-dark cycle (lights on at 6 am) with unrestricted access to food and water except during testing. All behavioral testing occurred during the dark phase of the light-dark cycle. All subjects were treated, housed and used in accordance with the National Institutes of Health guidelines and the Association for the Assessment and Accreditation of Laboratory Animal Care (AAALAC).

Drugs (−)Nicotine hydrogen tartrate was purchased from Sigma (St. Louis, Mo.), dissolved in saline and the pH adjusted to 7.0 (±0.5) with sodium hydroxide. The solution was then filtered through a 0.22 μm syringe filter (Fisher Scientific, Pittsburgh, Pa. 15219) for sterilization purposes. Nicotine doses are reported as free base concentrations. MPEP was kindly donated by Novartis Pharma AG, dissolved in 0.9% sodium chloride, and administered intraperitoneally in a volume of 1 or 10 ml/kg with a pretreatment time of 30 or 15 minutes in rats and mice, respectively.

Apparati

Rat Self-Administration and Food Responding Operant Boxes

Intravenous nicotine self-administration and food-maintained responding took place in twelve Plexiglas operant chambers each housed in a sound-attenuated box as described previously (Markou and Paterson 2001).

Mouse Self-Administration Operant Boxes

All nicotine self-administration in mice took place in an apparatus (San Diego Instruments, San Diego, Calif.) that consisted of four identical test cages (8×8×8 cm), allowing simultaneous testing of two pairs of mice (see Semenova et al. 1995, 1999; Kuzmin et al. 1996a, 1997). The boxes were constructed form opaque plastic and contained two apertures: one for nose-pokes, and one for tail-fixing. All test session functions and data were controlled and recorded by computer.

Rat Self-Administration and Food-Maintained Responding

Food Training and Acquisition of Nicotine Self-Administration

Approximately one week after preparation with catheters into the jugular vein (see Markou and Paterson 2001), rats were trained to self-administer nicotine (see Markou and Paterson 2001) at two doses (0.01 [n=9] and 0.03 [n=9] mg/kg/inf; free base) under a FR5 TO20 sec schedule. Two additional groups of rats were allowed to respond for food (45 mg Noyes food pellet) under a FR5 TO20 sec (n=10), and a FR5 TO210 sec (n=10) schedule. The two different schedules were employed to allow assessment of the effects of MPEP on responding for food under a reinforcement schedule (FR5 TO20 sec) identical to that used for nicotine, and under a reinforcement schedule (FR5 TO210) that equated response rates for food to those seen for nicotine. Responding on the active lever resulted in delivery of nicotine solution in a volume of 0.1 ml/infusion over a 1 second period (Razel Scientific Instruments Inc, Stamford, Conn.), while responding on the inactive lever had no consequences. Rats were considered to have acquired stable operant responding when they pressed the active lever more than twice the number of times they pressed the inactive lever, received a minimum of 6 infusions or 90 pellets per 1 hour session, with less than 20% variation in the number of reinforcers earned per session. Rats took approximately two weeks to establish stable rates of operant responding. All test sessions were conducted for one hour per day, five days per week.

Intravenous Self-Administration in Mice

Acute self-administration of nicotine was carried out using a previously described method (Semenova et al. 1995, 1999; Kuzmin et al. 1996a, 1997). The tails of the mice were fixed to the surface of the apparatus during the testing sessions to allow drug delivery; the fixing of the tail allowed the mice to move all of their four paws, head and entire body. Infusions of drug or vehicle (1.6 μl/inf delivered over 1 second) were administered to both mice in a pair, via the lateral tail-veins, contingent upon each nose-poke of one animal per pair (the active mouse). The only cue associated with the delivery of the drug or vehicle infusion was the noise of the pump. Mice were tested either once or twice, with approximately one month between each test. The second test only occurred in a subset of the original set of mice (2-7 pairs of mice from each of the original groups). This was done to increase the number of subjects/condition, and involved randomly assigning and testing these mice under a different set of conditions than in the original test (i.e., different nicotine and/or MPEP dose). Given the one month interval between the two tests for a limited subset of the mice, it is very unlikely that repeated testing affected the results.

Experimental Procedures

Experiment 1: Effect of MPEP Administration on Rates of Nicotine Self-Administration and Food-Maintained Responding on a Fixed Ratio Schedule of Reinforcement in Rats After acquiring stable nicotine self-administration at either 0.01 mg/kg/infusion (n=9) or 0.03 mg/kg/infusion (n=9), or stable food-maintained responding on the FR5 TO 20 sec schedule (n=10) or the FR5 TO210 sec schedule (n=10), drug testing was initiated. MPEP (0, 1, 3 and 9 mg/kg) was administered intraperitoneally 30 minutes before the session, according to a Latin Square design, with at least six days elapsing between each test dose. Drug was administered only when the animals had demonstrated stable self-administration behavior during the preceding 3 days, defined as less than 20% variation in daily performance.

Experiment 2: Effect of MPEP Administration on Nicotine Self-Administration in Drug-Naive Mice Saline or one of four nicotine doses (0.016, 0.048, 0.16, 0.48 μg/inf) were made available to different groups of animals. Each group consisted of 9-17 pairs of animals, including 2-7 mice per group that had previously undergone one testing session at least one month previously (see above). Pre-treatment with MPEP (0, 5, 10, 20 mg/kg intraperitoneally) occurred 15 minutes prior to the initiation of the test session.

Data Analyses

Experiment 1

Data were analyzed using a two-way ANOVA, with MPEP dose as the within-subjects factor (4 levels) and reinforcer as the between-subjects factor (4 levels: 0.01 and 0.03 mg/kg/inf nicotine, and food pellets, available on the FR5 TO20 sec and FR5 TO210 sec schedules). Data were expressed as a percentage of baseline (defined as the mean of the preceding three days; active lever data) and also as the number of lever presses (inactive lever data only). The level of significance was set at $p<0.05$.

Experiment 2

Data analyses were based on the comparison of both active and passive mouse nose-pokes in each pair, using the formula: $R=\log(A_T/P_T)-\log(A_{BL}/P_{BL})$, where $(A_T/P_T)$ is the ratio of the total number of active versus passive mouse nose-pokes during the 30-min test, and $(A_{BL}/P_{BL})$ is the ratio of the total number of active versus passive mouse nose-pokes during the 10-min pre-test. The effect of the drug was considered as reinforcing, neutral or aversive when R was higher, equal or lower than zero, respectively. Some data-points (9/237 pairs of mice) were excluded from the final analyses based on whether or not they lay within 2 standard deviations of the group mean for that specific condition. Nicotine self-administration data, obtained after saline pre-treatment, were analyzed using a one-way ANOVA with nicotine (4 levels) defined as the between-subjects factor. R-criterion data were analyzed using two-way ANOVAs with MPEP dose (4 levels)

and nicotine dose (4 levels) defined as the between-subjects factors. Pre-planned R-criterion data analyses were performed using one-way ANOVAs for each available dose of self-administered nicotine and saline, with MPEP dose (4 levels) defined as the between-subject factor. Appropriate individual comparisons were performed using the Student-Newman-Keuls post hoc test. The total self-injected doses of 0.048 μg/inf nicotine were analyzed using a one-way ANOVA with MPEP dose as the between-subjects factor, since analyses indicated that 0.048 μg/inf nicotine was the only dose reliably self-administered by the mice (see Results). Further, the raw nose-poke response rates for the nicotine dose that was reliably self-administered (0.048 μg/inf) were also subjected to a two-way ANOVA analysis with active/passive mouse as one factor, and MPEP dose as the second factor. Body weights and pre-test nose-poke activity levels were analyzed with three-way ANOVAs (nicotine dose, MPEP dose and mouse, i.e. active/passive, defined as between-subjects factors).

Results

Figure 6:
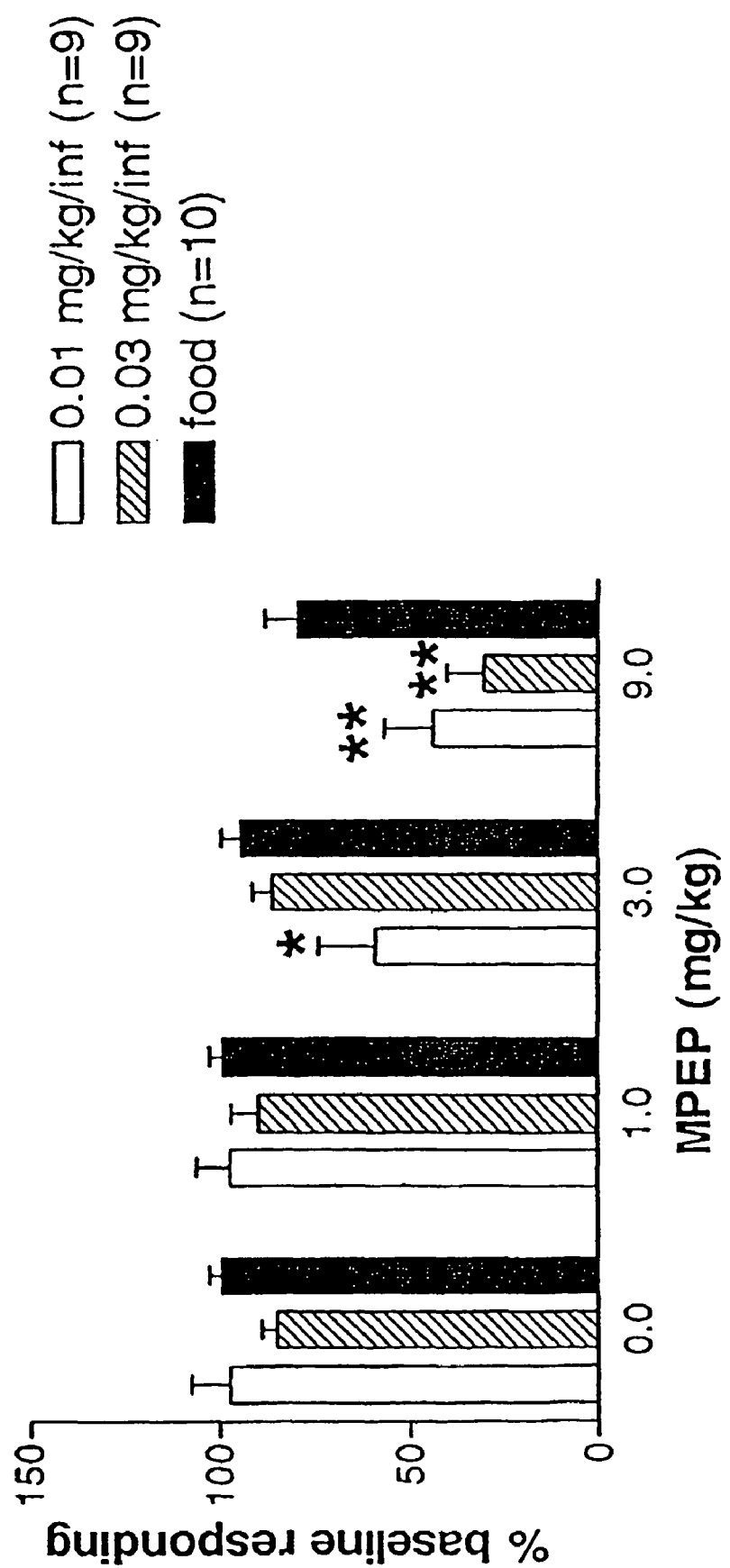
FIG. 6 illustrates the effects of MPEP administration on nicotine- and food-maintained responding in the rat. The data are expressed as percent of baseline responding (mean±SEM). Asterisks indicate significant differences from control conditions for each reinforcer (*p<0.05, **p<0.01).
Figure 7:
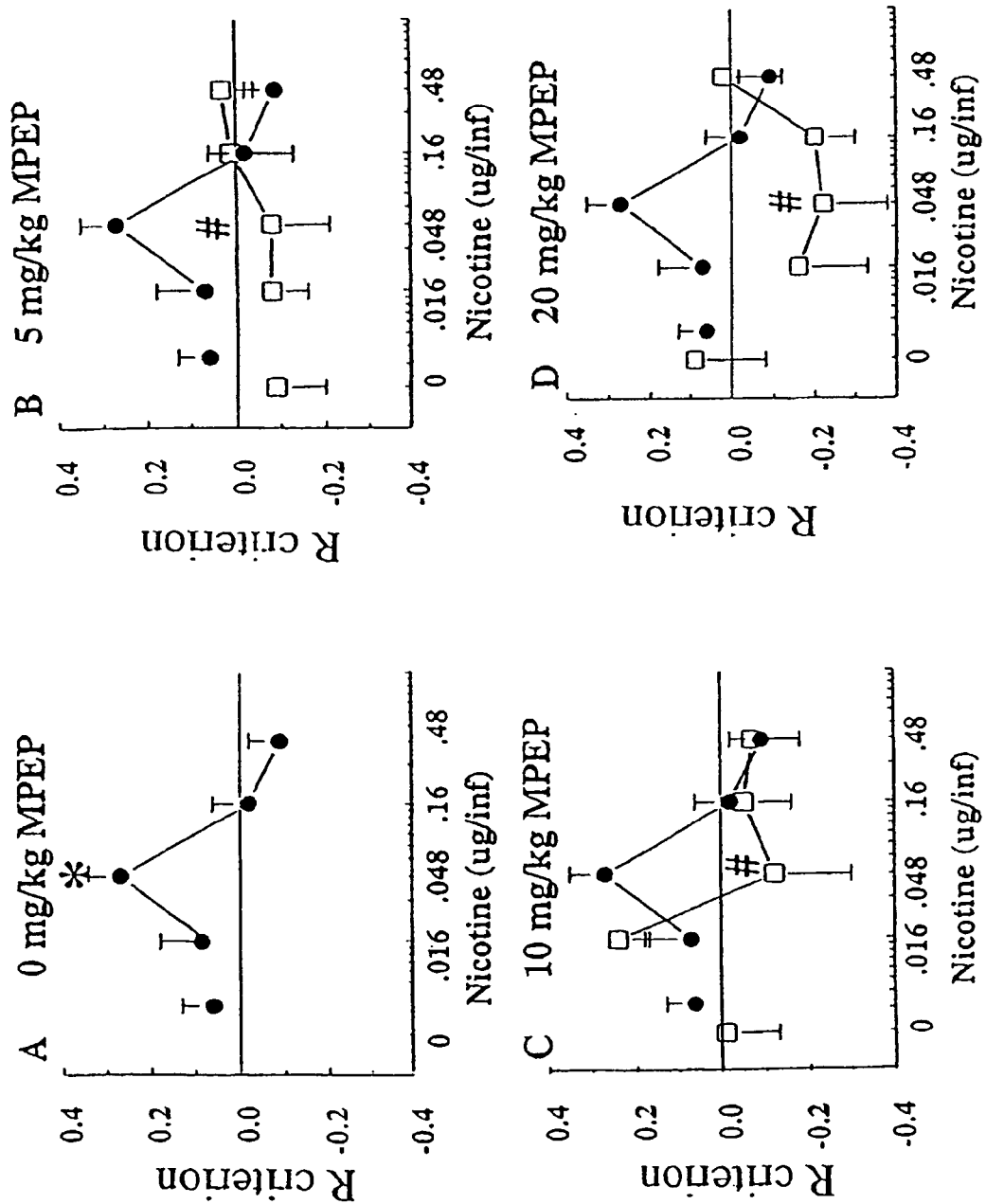
FIGS. 7A-7D illustrate nicotine dose-response curves obtained after pretreatment with different doses of MPEP (mean±SEM). The graphs in this figure depicts the nicotine dose-response curves obtained after pretreatment with 0 (FIG. 7A, 5 (FIG. 7B), 10 (FIG. 7C) and 20 (FIG. 7D) mg/kg MPEP. The filled circles are results from saline controls (the same data repeated in all four panels) and open squares are results from MPEP treated subjects. The asterisk (*) indicates significant (p<0.05) differences in R-criterion value for different available nicotine doses compared to saline. The pound signs (#) indicate significant differences from self-administration of the 0.048 μg/inf nicotine dose for each MPEP dose (5, 10 and 20 mg/kg) compared to saline pretreatment (p<0.05).

Experiment 1: Effect of MPEP Administration on Rates of Nicotine Self-Administration and Food-Maintained Responding on a Fixed Ratio Schedule of Reinforcement in Rats A significant MPEP×Reinforcer interaction effect $[F(9, 102)=4.22, p<0.001]$ indicated that MPEP affected nicotine self-administration and food-maintained responding differently (FIG. 6; Table 4). Further, there were significant main effects of MPEP dose $(F[3,102]=23.33, p<0.001)$ and reinforcer $(F[3,34]=14.07, p<0.001)$ (FIG. 7). Newman-Keuls post-hoc tests indicated that 3 and 9 mg/kg MPEP significantly reduced self-administration of the 0.01 mg/kg/infusion nicotine dose relative to the vehicle condition, while decreasing self-administration of the 0.03 mg/kg/inf dose only at 9 mg/kg. In contrast to the nicotine-maintained responding, food-maintained responding under either the FR5 TO20 sec or the FR5 TO210 sec schedules was not significantly reduced at any MPEP dose administered. Analysis of inactive lever data indicated that there was no effect of MPEP on inactive lever presses for any of the reinforcers, as indicated by the lack of a main effect of MPEP dose. There was an effect of reinforcer on inactive lever presses $[F(3,34)=4.47, p<0.01]$, but there was no significant MPEP×Reinforcer interaction.

Figure 8:
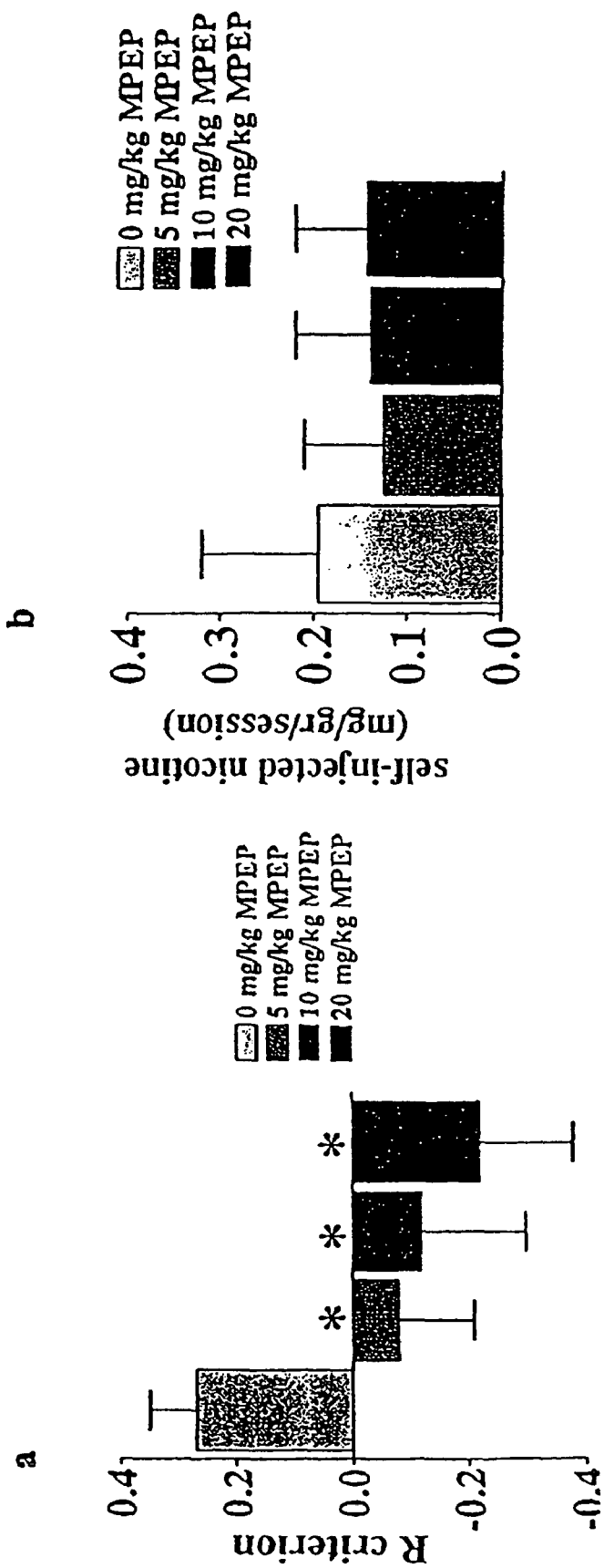
FIGS. 8A-8B illustrate the effect of MPEP administration on intravenous self-administration of 0.048 μg/inf nicotine in DBA/2J mice (mean±SEM). Panel A (left panel) depicts the effects of MPEP pretreatment on self-administration of this reliably self-administered nicotine dose (0.048 Tg/inf nicotine). Panel B (right panel) shows total self-injected nicotine dose when 0.048 μg/inf nicotine was available after pretreatment with MPEP (0, 5, 10 and 20 mg/kg). Asterisks (*) indicate significant differences after pretreatment with each MPEP dose (5, 10 and 20 mg/kg) compared to saline pretreatment (p<0.05).

Experiment 2: Effect of MPEP Administration on Nicotine Self-Administration in Drug-Naive Mice Statistical analysis of R-criterion data indicated that drug-naive mice acquired nicotine self-administration as indicated by a significant main effect of nicotine $[F(4,71)=3.4, p<0.05]$. Post-hoc comparisons indicated that self-administration of the 0.048 μg/inf nicotine dose was significantly different from saline administration (FIG. 8). Statistical analyses of R-criterion data indicated there was a trend towards a significant interaction of MPEP×Nicotine dose $[F(3,90)=1.89, p=0.056]$. Based on pre-planned comparisons for the effect of MPEP on self-administration of each nicotine dose, one-way ANOVAs indicated that MPEP had a significant effect only on self-administration of the 0.048 μg/inf nicotine dose $[F(3,46)=3.53, p<0.05]$, that was actually the only nicotine dose to be reliably self-administered. Post-hoc comparisons indicated that MPEP significantly reduced nicotine self-administration at all doses tested (FIG. 8). Interestingly, FIG. 8A appears to show a trend for 20 mg/kg MPEP to decrease the R-criterion below zero, perhaps indicating that this dose of MPEP makes nicotine aversive, under the test conditions. Analyses indicated no significant effect of MPEP on total self-injected nicotine dose (FIG. 8B). Nevertheless, MPEP significantly decreased nose-poke responding in the active mice, as indicated by a Mouse (Active vs Passive)×MPEP interaction effect $[F(3,96)=3.46, p<0.05)]$. There was no difference between any of the experimental groups for pre-test nose-poke activity. In addition, there were no significant differences in body weights between the different conditions, as indicated by a lack of a significant three-way interaction. Table 5 shows the raw data for each group of mice, expressed as the number of nose-pokes per minute, recorded during the pre-test and during the self-administration session, for both active and passive mice.

TABLE 4

Number of reinforcers earned during rat nicotine self-administration and food-maintained responding during the entire 1 hour session. The data are expressed as the range of raw values seen in all experimental subjects under baseline conditions, and also as the mean ± SEM of reinforcers earned after MPEP (0, 1, 3 and 9 mg/kg) pretreatment.

| Reinforcer | Schedule | 0 mg/kg MPEP | 1 mg/kg MPEP | 3 mg/kg MPEP | 9 mg/kg MPEP |
|---|---|---|---|---|---|
| 0.01 mg/kg/inf nic | FR5 TO20 sec | 18.9 ± 2.8 | 21 ± 3.1 | 11 ± 2.7 | 9.1 ± 3.0 |
| 0.03 mg/kg/inf nic | FR5 TO20 sec | 12.9 ± 1.2 | 13 ± 1.9 | 11.4 ± 1.2 | 4.8 ± 1.5 |
| 45 mg food pellet | FR5 TO20 sec | 122.7 ± 6.0 | 131.3 ± 8.2 | 122.2 ± 7.4 | 109 ± 12.98 |
| 45 mg food pellet | FR5 TO210 sec | 16.1 ± 0.4 | 16.3 ± 0.3 | 15.2 ± 0.5 | 15.2 ± 0.6 |

TABLE 5

Raw data from the mouse self-administration experiment. The data in the
table include the sample size for each condition, expressed as the number of pairs of mice,
and also rates of nose-pokes responses recorded during both pre-test and test sessions,
under all conditions, for both active and passive subjects, expressed as mean responses per
minute ± SEM. For the 0.048 µg/kg/inf nicotine dose, there was a significant interaction
between the factors mouse (active vs passive) and the factor MPEP indicating that MPEP
differentially affected nose-poke rates in the active versus the passive mice.

| Nicotine (µg/inf) | MPEP (mg/kg) | n | active pre-test | active test | passive pre-test | passive test |
|---|---|---|---|---|---|---|
| 0 | 0 | 15 | 8.79 ± 0.98 | 4.62 ± 1.05 | 9.37 ± 1.11 | 4.05 ± 0.82 |
| 0 | 5 | 10 | 8.19 ± 1.03 | 4.99 ± 1.17 | 8.38 ± 0.96 | 6.41 ± 1.38 |
| 0 | 10 | 10 | 7.95 ± 0.99 | 4.92 ± 1.1 | 8.00 ± 1.06 | 5.86 ± 1.56 |
| 0 | 20 | 10 | 6.98 ± 1.18 | 5.96 ± 1.69 | 8.50 ± 1.43 | 6.33 ± 1.66 |
| 0.016 | 0 | 13 | 8.0 ± 1.22 | 3.88 ± 0.46 | 8.85 ± 1.25 | 4.56 ± 0.86 |
| 0.016 | 5 | 11 | 7.86 ± 0.87 | 2.62 ± 0.49 | 8.01 ± 0.91 | 3.46 ± 0.74 |
| 0.016 | 10 | 13 | 7.79 ± 0.83 | 6.48 ± 1.05 | 8.22 ± 0.87 | 4.26 ± 0.94 |
| 0.016 | 20 | 10 | 7.10 ± 0.87 | 5.48 ± 1.09 | 7.35 ± 0.85 | 8.77 ± 1.85 |
| 0.048 | 0 | 17 | 8.04 ± 0.89 | 5.42 ± 1.19 | 8.50 ± 1.07 | 3.06 ± 0.68 |
| 0.048 | 5 | 12 | 9.13 ± 1.37 | 3.43 ± 0.67 | 8.93 ± 1.36 | 4.45 ± 1.06 |
| 0.048 | 10 | 11 | 7.43 ± 0.98 | 3.92 ± 1.18 | 8.06 ± 1.39 | 5.83 ± 1.72 |
| 0.048 | 20 | 10 | 8.36 ± 1.07 | 3.56 ± 1.04 | 8.31 ± 1.28 | 5.29 ± 1.11 |
| 0.16 | 0 | 16 | 7.58 ± 0.77 | 3.63 ± 0.58 | 7.69 ± 0.88 | 3.9 ± 0.69 |
| 0.16 | 5 | 14 | 8.32 ± 0.94 | 4.67 ± 0.95 | 8.48 ± 3.31 | 4.32 ± 2.37 |
| 0.16 | 10 | 11 | 7.12 ± 0.66 | 4.19 ± 0.81 | 7.20 ± 0.69 | 4.62 ± 0.82 |
| 0.16 | 20 | 10 | 7.50 ± 1.25 | 5.06 ± 1.52 | 7.56 ± 1.32 | 7.97 ± 1.76 |
| 0.48 | 0 | 15 | 6.50 ± 0.90 | 2.29 ± 0.25 | 6.77 ± 0.87 | 3.28 ± 0.5 |
| 0.48 | 5 | 9 | 8.12 ± 1.17 | 3.04 ± 0.73 | 8.58 ± 1.38 | 3.25 ± 0.88 |
| 0.48 | 10 | 10 | 7.49 ± 0.86 | 3.58 ± 0.73 | 7.48 ± 0.88 | 3.81 ± 0.47 |
| 0.48 | 20 | 10 | 7.31 ± 0.98 | 4.67 ± 1.22 | 7.08 ± 0.94 | 4.35 ± 0.98 |

Discussion

The results of the present study indicated that MPEP administration selectively decreased nicotine self-administration in the rat with increased efficacy at the lower available nicotine dose, without affecting food-maintained responding on either of the two food-maintained schedules of reinforcement employed. In addition, MPEP administration in drug-naive mice was shown to suppress self-administration of the nicotine dose that was shown to be reliably self-administered (0.048 µg/inf nicotine). These data indicate that MPEP pretreatment reduced the reinforcing efficacy of self-administered intravenous nicotine in two different rodent species.

In the rats there were no obvious motor suppressant effects that could account for the reduction in nicotine self-administration, as indicated by the maintenance of high levels of responding for food on either of the two schedules of reinforcement, one of which equated response rates to those seen for nicotine. In the mice experiment there was no effect of MPEP administration on nose-poke activity. Previous studies generally have indicated no effects of MPEP on locomotor activity in rodents. In rats, MPEP at doses of 2.5-10 mg/kg, delivered intraperitoneally (i.p.), had no effect on exploratory locomotor activity in rats (Tatarczynska et al. 2001; Henry et al. 2002), although another study indicated that much higher doses of MPEP inhibited spontaneous locomotor activity; but even very high doses were without effect on rotarod performance (Spooren et al. 2000a). Similarly in mice, Tatarczynska and co-workers (2001) demonstrated that 30 mg/kg MPEP (i.p.) had no effect on rotarod performance, but a different study (Spooren et al. 2000a) showed that a much higher dose of MPEP reduced vertical activity. In summary, previous work and the present data on food-maintained responding in rats indicate that at the doses of MPEP used in the present study, non-specific motor effects are very unlikely to account for the reduced nicotine self-administration. Furthermore, the observed differences in the effects of MPEP on nicotine-versus food-maintained responding cannot be attributed to a rate-dependent effect, since the use of the FR5 TO210 sec schedule provided equivalent rates of responding for nicotine and food and even under these conditions MPEP did not affect responding for food.

With the mouse self-administration technique used in the present study, mice demonstrated self-administration at one of the five doses tested across a wide range of nicotine doses. This procedure for self-administration in drug-naive mice has been used to study the self-administration of morphine (Semenova et al. 1995, 1999; Kuzmin et al. 1996a, 1997), cocaine (Kuzmin et al. 1996b; 1997), ethanol (Kuzmin et al., 1999), nicotine (Stolerman et al. 1999; Fattore et al. 2002), amphetamine (Cossu et al., 2001) and gamma-hydroxybutyric acid (Martellota et al. 1998). A wide range of nicotine doses was used in the present study because of uncertainty over the likely self-administered nicotine dose range in the DBA/2J mice used, and to allow for large shifts in the nicotine dose-response curve after MPEP pretreatment. Although only limited conclusions can be drawn from studies utilizing only one unit dose of the self-administered drug, the present mouse data are presented in the context of, and in addition to, the extensive self-administration studies in the rat. The partial restraint used in the mouse procedure could increase drug self-administration behavior (Piazza et al. 1990; Shaham et al. 1993; Ramsey and Van Rees 1993), although physical stress (i.e. foot shock) was shown previously not to affect self-administration of morphine using the present procedure (Kuzmin et al., 1996). In contrast to the mouse technique, the methodologies employed in the rat experiments in the present study examined self-administration behavior at two different unit doses of nicotine, and examined the maintenance rather than acquisition of nicotine self-administration. Furthermore, the rat studies included two food-maintained schedules of reinforcement, with one schedule (FR5 TO20 sec) identical to the schedule used for the nicotine self-administration work, and another schedule (FR5 TO 210 sec) used to equilibrate levels of responding for nicotine and food. Regarding the results obtained from the mouse experiment, MPEP was shown to significantly reduce self-administration of the 0.048

µg/inf nicotine dose, as measured by the R criterion. In contrast, although there was a trend towards an effect of MPEP on total nicotine intake, it was not significant. Nevertheless, the two-way ANOVA on the raw nose-poke data at the 0.048 µg/inf nicotine dose clearly indicated a differential effect of MPEP pretreatment on active versus passive mice, with the active mice exhibiting decreased nose-poke rates after MPEP administration. In summary, although the data obtained from the mouse experiment in the present study, considered in isolation, provide only limited evidence for the effect of MPEP on nicotine self-administration, they do provide converging evidence for the more complete and persuasive data provided in the rat experiments.

The effects of MPEP on nicotine self-administration in rodents are consistent with those seen previously for cocaine self-administration in mice (Chiamulera et al. 2001). It was shown that mutant mice with an mGluR5 deletion would not acquire cocaine self-administration at any of the doses effective in the wild type controls, but food-maintained responding was unaffected. The effect of the mGluR5 deletion was confirmed via administration of MPEP in wild type mice, which was shown to dose-dependently reduce cocaine self-administration without affecting food-maintained responding. Interestingly, the authors demonstrated that cocaine administration resulted in similar increases in dopamine levels in the NAcc in both the mutant and wild type mice, perhaps indicating that increased midbrain dopamine levels alone are not sufficient to maintain cocaine self-administration. This hypothesis is supported by recent findings indicating that dopamine (D2) receptor knockout mice self-administer cocaine (Caine et al. 2002), and dopamine (D1) receptor knockouts acquire cocaine-induced conditioned place preference (Miner et al. 1995). Nevertheless, although there was no difference in the absolute level of NAcc dopamine levels between the mGluR5 knockout compared to the wild type mice, there was an apparent difference in the time taken for NAcc dopamine levels to increase to those levels. Perhaps it is this difference that resulted in the observed differences in cocaine self-administration and cocaine-induced hyperlocomotion between the wild type and the homozygous mGluR5-deficicent mutant mice.

Regarding the rewarding effects of acute nicotine, a recent study (Harrison et al. 2002) investigated the effect of MPEP administration on nicotine reward as measured in a brain reward stimulation procedure. MPEP administration had no effect on the reward-lowering effect of 0.25 mg/kg nicotine (Harrison et al. 2002), although MPEP alone elevated brain reward thresholds. This discrepancy in results may be due to the much higher doses (0.125 and 0.25 mg/kg i.p.) of nicotine administered in the previous study (by the experimenter), compared to the effect of self-administered 0.03 or 0.01 mg/kg/inf nicotine, delivered repeatedly and intravenously. Importantly, the neurobiological substrates underlying lateral hypothalamic self-stimulation and intravenous nicotine self-administration may be quite different (Harrison et al. 2002), and it may be these differences that underlie the different effects of MPEP in the two studies.

A number of studies have indicated a role for mGluRs in modulating dopamine neurotransmission in the striatum and NAcc, and generally, group I mGluRs (mGluR5 and mGluR1) are thought to be involved in modulation of postsynaptic responses (Schoepp 2001). Interestingly, it was found recently that intra-accumbens administration of a group I mGluR antagonist blocked the locomotor-activating effect of a D-1 receptor agonist (David and Abraini 2001). As stated above, it has been shown previously that mGluR5s are concentrated heavily in the NAcc, where significant increases in extracellular dopamine levels are seen after administration of nicotine. In addition, the absence of mGluR5s in mice resulted in the absence of cocaine self-administration and cocaine-induced hyperactivity, and yet cocaine-induced increases in NAcc dopamine were relatively unchanged (Chiamulera et al. 2001). Taken together with the present findings indicating the effect of MPEP on nicotine self-administration, one explanation is that mGluR5s play a modulatory role in the postsynaptic response to drug-induced dopamine release in the NAcc, thereby decreasing nicotine self-administration. Alternatively, given the role of glutamate in mediating the rewarding effects of both nicotine (Watkins et al. 2000) and cocaine (Zhang et al. 2001), it may be that dopamine plays a less critical role in mediating the rewarding effects of psychostimulants than is often hypothesized.

The anxiolytic-like effect of MPEP may be related to its effects on self-administration of nicotine and cocaine. Nicotine can be anxiogenic at higher doses (File et al. 1998; Irvine et al. 2001), although it also has been shown to be anxiolytic at lower doses (File et al. 1998; Szyndler et al. 2001). Administration of amphetamine, cocaine and nicotine all increase plasma levels of stress hormones in laboratory animals (for review, see Sarnyai et al. 2001). It has been hypothesized that the anxiogenic effects of chronic self-administered nicotine observed in rats may play a role in maintaining nicotine self-administration (Irvine et al. 2001). Pretreatment with anxiolytic benzodiazepine compounds selectively reduced cocaine-maintained responding without affecting food-maintained behavior in rats (Goeders et al. 1989; 1993; Goeders 1997). Previous studies have indicated the anxiolytic-like effects of MPEP in rodents (Spooren et al. 2000b; Tatarczynska et al. 2001). It is possible therefore that the anxiolytic effects of MPEP may block the mildly heightened anxiety levels induced by nicotine, and thus may block part of its rewarding effects.

In summary, the present study indicated that MPEP pretreatment significantly reduced nicotine self-administration with no effect on food-maintained responding in rats and in drug-naive mice in the absence of any motor-suppressant activity. It is hypothesized here that MPEP administration modulated the postsynaptic response to nicotine-induced increased dopamine levels in the terminal field of the mesolimbic circuit. Nevertheless, given the limits of the present experiments and current knowledge on the precise location and function of mGluR5s, modes of action of MPEP at sites other than the NAcc and/or via an anxiolytic-like effect, cannot be ruled out. The present results may indicate a novel therapeutic target for anti-smoking, and more generally, anti-abuse medications.

REFERENCES FOR EXAMPLE 2

Battaglia G, Bruno V, Pisani A, Centonze D, Catania M V, Calabresi P, Nicoletti F (2001), Mol Cell Neurosci 17:1071-1083
Battaglia G, Fornai F, Busceti C L, Aloisi G, Cerrito F, De Blasi A, Melchiorri D, Nicoletti F (2002), J Neurosci 22(6): 2135-2141
Breysse N, Baunez C, Spooren W, Gasparini F, Amalric M (2002), J Neurosci 22(13):5669-5678
Caine S B, Negus S S, Mello N K, Patel S, Bristow L, Kulagowski J, Vallone D, Saiardi A, Borrelli E (2002), J Neurosci 22(7):2977-2988
Cartmell J, Schoepp D D (2000), J Neurochem 75:889-907
Chapman A G, Nanan K, Williams M, Meldrum B S (2000), Neuropharmacology 39:1567-1574

Chiamulera C, Epping-Jordan M P, Zocchi A, Marcon C, Cottiny C, Tacconi S, Corsi M, Orzi F, Conquet F (2001), Nature Neurosci 4(9):873-874

Conn P J, Pin J-P (1997), Annu Rev Pharmacol Toxicol 37:205-37

Corrigall W A, Coen K M (1991), Psychopharmacology 104:171-176

Corrigall W A, Coen K M, Zhang J, Adamson L (2002), Psychopharmacology 160:198-205

Cossu G, Ledent C, Fattore L, Imperato A, Bohme G A, Parmentier M, Fratta W (2001), Behav Brain Res 118(1):61-5

David H N, Abraini J H (2001), Eur J Neurosci 13:2157-2164

Dewey S L, Brodie J D, Gerasimov M, Horan B, Gardner E L, Ashby C R Jr. (1999), Synapse 31:76-86

Fattore L, Cossu G, Martellotta M C, Fratta W (2002), Alcohol 37(5):495-498

File S E, Kenny P J, Ouagazzal A-M (1998), Behav Neurosci 112:1423-1429

Gasparini F, Lingenhohl K, Stoehr N, Flor P J, Heinrich M, Vranesic I, Biollaz M, Aligeier H, Heckendorn R, Urwyler S, Varney M A, Johnson E C, Hess S D, Rao S P, Sacaan A I, Santori E M, Velicelebi G, Kuhn R (1999), Neuropharmacology 38:1493-1503

Ghasemzadeh M B, Nelson L C, Lu X-Y, Kalivas P W (1999), J Neurochem 72: 157-165

Goeders N E, McNulty M A, Mirkis S, McAllister K H (1989), Pharmacol Biochem Behav 33:859-866

Goeders N E, McNulty M A, Guerin G F (1993), Pharmacol Biochem Behav 44:471-474

Goeders N E (1997), Psychoneuroendocrinology 22(4):237-259

Harrison A A, Gasparini F, Markou A (2002), Psychopharmacology 160:56-66

Henry S A, Lehmann-Masten V, Gasparini F, Geyer M A, Markou A (2002), Neuropharmacology. In Press.

Hoischer C, Gigg J, O'Mara S M (2001), Neurosci Biobehav Rev 23:399-410

Irvine E E, Bagnalasta M, Marcon C, Motta C, Tessari M, File S E, Chiamulera C (2001), Psychopharmacology 153:315-320

Kuzmin A, Semenova S, Zvartau E E, van Ree J M (1996a), Eur Neuropsychopharmacol 6:63-68

Kuzmin A, Semenova S, Ramsey N F, Zvartau E E, van Ree J M (1996b), Eur J Pharmacol 295:19-25

Kuzmin A V, Semenova S, Gerrits M A, Zvartau E E, van Ree J M (1997), Eur J Pharmacol 321(3):265-271

Kuzmin A, Semenova S, Zvartau E, De Vry J (1999), Eur Neuropsychopharmacol 9:197-203

Mansvelder H D, Keath J R, McGehee D S (2002), Neuron 33(6):905-919

Markou A, Paterson N E (2001), Nic Tob Res 3:361-373

Martellotta M C, Cossu G, Fattore L, Gessa G L, Fratta W (1998), Eur Neuropsychopharmacol 8(4):293-296

McGehee D S, Heath M J S, Gelber S, Devay P, Role L W (1995), Science 269:1692-1696

Miner L L, Drago J, Chamberlain P M, Donovan D, Uhl G R (1995), Neuroreport 6(17):2314-2316

Ossowska K, Konieczny J, Wolfarth S, Wieronska J, Pilc A (2001), Neuropharmacology 41:413-420

Paterson N E, Markou A (2002), Synapse 44:252-253

Piazza P V, Deminiere J M, Le Moal M, Simon H (1990), Brain Res 514:22-26

Picciotto M R, Corrigall W A (2002), J Neurosci 22(9):3338-3341

Ramsay N F and Van Ree J M (1993), Brain Res. 608:216-22

Reid M S, Fox L, Ho L B, Berger S P (2000), Synapse 35(2):129-136

Sarnyai Z, Shaham Y, Heinrichs S C (2001), Pharmacol Rev 53(2):209-243

Schilstrom B, Fagerquist M V, Zhang X, Hertel P, Panagis G, Nomikos G G, Svensson T H (2000), Synapse 38(4):375-383

Schoepp D D (2001), J Pharmacol Exp Ther 299:12-20

Schulz B, Fendt M, Gaparini F, Lingenhohl K, Kuhn R, Koch M (2001), Neuropharmacology 41:1-7

Semenova S, Kuzmin A, Zvartau E (1995), Pharmacol Biochem Behav 50(1):17-21

Semenova S, Danysz W, Bespalov A (1999), Eur J Pharmacol 378(1):1-8

Shaham Y, Alvares K, Nespor S M and Grunberg N E (1992), Pharmacol Biochem Behav 41:615-619

Shigemoto R, Nomura S, Ohishi H, Sugihara H, Nakanishi S, Mizuno N (1993), Neurosci Lett 163(1):53-57

Spooren W P J M, Gasparini F, Bergmann R, Kuhn R (2000a), Eur J Pharmacol 406:403-410

Spooren W P J M, Vassout A, Neijt H C, Kuhn R, Gasparini F, Roux S, Porsolt R D, Gentsch C (2000b), J Pharmacol Exp Ther 295:1267-1275

Spooren W P J M, Gaparini F, Salt T E, Kuhn R (2001), Trends Pharmacol Sci 22(7):331-337

Stolerman I P, Naylor C, Elmer G I, Goldberg S R (1999), Psychopharmacology 141(3):297-306.

Szyndler J, Sienkiewicz-Jarosz H, Maciejak P, Siemiatkowski M, Rokicki D, Czlonkowska A I, Plaznik A (2001), Pharmacol Biochem Behav 69:511-518

Tatarczynska E, Klodzinska A, Chojnacka-Wojcik E, Palucha A, Gasparini F, Kuhn R, Pilc A (2001), Br J Pharmacol 132:1423-1430

Tallaksen-Greene S J, Kaatz K W, Romano C, Albin R L (1998), Brain Res 780:210-217

Vezina P, Kim J-H (1999), Neurosci Biobehav Rev 23:577-589

Watkins S S, Koob G F, Markou A (2000), Nicotine Tob Res. 2(1):19-37

Zhang Y, Loonam T M, Noailles P A, Angulo J A (2001), Ann N Y Acad Sci 937:93-120

Example 3

Supplemental Evidence for the Utility of Simultaneous Blockade of Metabotropic Glutamate 5 and Metabotropic Glutamate 2/3 Receptors in the Treatment of Drug Addiction and Depression This Example illustrates that blockade of glutamatergic transmission at mGlu5 and/or mGlu2/3 receptors decreases the reinforcing properties of cocaine and nicotine (present data; Paterson et al. 2003), and indicates that simultaneous blockade of these receptors has additive effects on inhibiting drug-taking behavior. Most drugs of abuse have been shown to increase excitatory glutamatergic transmission throughout brain reward circuitries (Kalivas and Duffy, 1998; Mansvelder and McGehee, 2000; Ungless et al., 2001; Wolf, 2003). Although the precise role of excitatory glutamatergic transmission in regulating brain reward circuitries is unclear, increases in excitatory glutamatergic transmission contribute to the reinforcing properties of addictive drugs. Indeed, blockade of glutamatergic transmission has been shown to decrease the rewarding actions of cocaine and other drugs of abuse (Harris and Aston-Jones, 2003; Laviolette and van der Kooy, 2003).

There has been a recent interest in the role of the metabotropic glutamate 5 (mGlu5) receptor in regulating the reinforcing effects of addictive drugs based on the observations of Chiamulera and colleagues (2001) demonstrating that mice in which the gene for the mGlu5 receptor was deleted did not acquire cocaine self-administration behavior. However, the acquisition of food self-administration was unaffected in these mice, demonstrating that the decrease in cocaine consumption in these mice was not secondary to a deficit in learning processes (Chiamulera et al., 2001). Consistent with the above, the selective mGlu5 receptor antagonist MPEP decreased cocaine self-administration in wild-type control mice (Chiamulera et al., 2001). Similarly, as shown in Example 2 above, MPEP decreased nicotine self-administration in both rats and mice, and attenuated cocaine- and morphine-induced conditioned place preference (McGeehan and Olive, 2003; Popik and Wrobel, 2002). More recently, blockade of metabotropic glutamate 2/3 (mGlu2/3) receptors has been shown to attenuate the behavioral actions of many drugs of abuse (David and Abrain, 2003). In addition, as illustrated in Example 1, the mGlu2/3 receptor antagonist LY341495 attenuated the deficits in brain reward function, measured by elevations in ICSS reward thresholds, observed in rats undergoing spontaneous nicotine withdrawal (depression-like signs). Taken together, these data suggest that mGlu5 and mGlu2/3 receptors play a crucial role in regulating the behavioral actions of various drugs of abuse including cocaine and nicotine, and depressive symptoms seen in both drug addiction and non-drug-induced depressions.

Acute cocaine administration has been shown to lower intracranial self-stimulation (ICSS) thresholds (Esposito et al., 1978; Frank et al., 1988; Kenny et al., 2003a; Kenny et al., 2003b; Kokkinidis and McCarter, 1990; Markou and Koob, 1992). Because ICSS directly activates brain reward circuitries (Olds and Millner, 1954), ICSS thresholds are thought to provide an operational measure of brain reward function. Thus, the lowering in ICSS thresholds observed after cocaine administration reflects an increase in brain reward function that most likely underlies cocaine's euphorigenic effects. This increase in brain reward function associated with cocaine consumption is considered relevant to the establishment and maintenance of cocaine self-administration behavior (Kenny et al., 2003b; Stewart et al., 1984).

The first aim of the present studies was to investigate the effects of MPEP on nicotine self-administration in rats, and on cocaine self-administration in rats with two different schedules of daily access (1 and 6 h) to cocaine self-administration. Next, we investigated whether MPEP decreased the 'motivation' of rats to obtain cocaine or nicotine by examining whether MPEP decreased responding for cocaine or nicotine under a progressive ratio schedule of reinforcement. We then investigated whether MPEP decreased the positive affective state associated with cocaine consumption, by examining if MPEP attenuated the lowering actions of acutely administered cocaine on ICSS thresholds. Next, we examined the effects of the mGlu2/3 receptor antagonist LY341495, previously shown to attenuate nicotine withdrawal (Kenny et al., 2003c), on nicotine self-administration in rats. Finally, we examined whether simultaneous blockade of mGlu5 and mGlu2/3 receptors, by combining MPEP and LY341495, had an additive inhibitory effect on nicotine self-administration behavior.

Materials and Methods
(i) Subjects

Subjects were Wistar rats weighing 300-320 g upon arrival at the laboratory. Rats were obtained from Charles River Laboratories (Raleigh, N.C.) and were housed in groups of two or three per cage, with food and water available ad libitum. Animals were maintained in a temperature-controlled vivarium under a 12 hr light/dark cycle (lights off at 10:00 am). In each case animals were tested during the dark portion of the light/dark cycle. All animals were treated in accordance with the guidelines of the National Institutes of Health regarding the principles of animal care. Animal facilities and experimental protocols were in accordance with the Association for the Assessment and Accreditation of Laboratory Animal Care.

Drugs

Cocaine hydrochloride and (−) nicotine hydrogen tartrate were purchased from Sigma Chemical Co., St. Louis, Mo. 2-Methyl-6-[phenylethynyl]-pyridine) was synthesized according to procedures known in the art. LY341495 was obtained from Tocris. Drugs were prepared immediately before each administration. For systemic cocaine administration, cocaine was dissolved in sterile 0.9% (w/v) saline, and administered by intraperitoneal (i.p.) injection in a volume of 1 ml/kg body weight, 10 min before the ICSS experimental session. For systemic MPEP administration, MPEP was dissolved in sterile water and administered by i.p. injection, in a volume of 1 ml/kg body weight, 30 min before the ICSS or self-administration session. For systemic LY341495 administration, LY341495 was dissolved in sterile saline and administered by i.p. injection, in a volume of 3 ml/kg body weight, 30 min before the self-administration session.

Apparatus

Intracranial self-stimulation training and testing took place in sixteen Plexiglas operant chambers (25×31×24 cm) (Med Associates, St. Albans, Vt.). The floors of the operant chambers were constructed of parallel aluminum rods spaced 1.25 cm apart. One wall contained a metal wheel manipulandum that required 0.2 N force to rotate it one-quarter of a turn. The wheel (5 cm in width) extended out of the wall ~3 cm. Each testing chamber was enclosed within a light- and sound-attenuated chamber (62×63×43 cm). Intracranial stimulation was delivered by constant current stimulators (Stimtech model 1200; San Diego Instruments, San Diego, Calif.). Subjects were connected to the stimulation circuit through flexible bipolar leads (Plastics One, Roanoke, Va.) attached to gold-contact swivel commutators mounted above the chamber. The stimulation parameters, data collection, and all test session functions were controlled by a microcomputer.

Cocaine and nicotine self-administration took place in 16 Plexiglas, sound-attenuated operant chambers (29×24×19.5 cm). In each chamber, one wall contained a metal retractable lever that was mounted 2.5 cm above the floor and required a 0.1 N force to be pressed. Plastic swivels, connected the animals to syringes operated by Razel pumps that delivered the drug. Data collection and all programming functions were controlled by an IBM-compatible microcomputer.

Surgery

Rats prepared with intravenous catheters were anaesthetized by inhalation of 1-3% isoflurane in oxygen and prepared with silastic catheters, surgically implanted in the jugular vein as described previously (Caine et al., 1993). The catheter was passed subcutaneously to a polyethylene assembly mounted on the animal's back. This assembly consisted of a guide cannula (Plastic One Co., Roanoke Va.) attached to a 4 cm² piece of marlex mesh with epoxy. The marlex mesh was placed under the skin on the animal's back. After surgery, catheters were flushed daily with 0.15 ml of a sterile antibiotic solution containing heparinized saline (30 USP units/ml) and Timentin (100 mg/ml; SmithKline Beecham Pharmaceuticals, Philadelphia, Pa.). Rats prepared with ICSS electrodes were anaesthetized by inhalation of 1-3% isoflurane in oxygen and positioned in a stereotaxic frame (Kopf Instruments, Tujunga, Calif.). The incisor bar was adjusted to 5 mm above the interaural line, and the skull exposed. Stainless steel bipolar stimulating electrodes (11 mm in length) were implanted into the posterior lateral hypothalamus (AP: −0.5 mm from bregma; ML: ±1.7 mm; DV: 8.3 mm from dura, with the incisor bar positioned 5 mm above the interaural line), according to the atlas of Pellegrino et al. (1979). Four indentations were made in the skull to accommodate screws that, together with the application of dental acrylic, held the electrode in place. Animals were allowed to recover from surgery for at least 7 days prior to training in the ICSS or self-administration procedures.

Intravenous Cocaine Self-Administration Procedure

Rats (n=14) were food restricted to maintain them at 85% of their normal body weight obtained under free-feeding conditions, then trained to press a lever for 45 mg food pellets on a fixed-ratio 5 (FR5) schedule of reinforcement. Once stable responding for food reinforcement was achieved, rats were tested for cocaine self-administration during daily 1 h sessions for nine days on a FR5 schedule of reinforcement, when five responses on the lever resulted in the delivery of one cocaine injection (250 µg/injection dissolved in 0.1 ml of sterile 0.9% sterile saline; delivered over 4 sec) and initiated a 20 sec time-out (TO) period, signaled by a light cue located above the lever, during which time responding on the lever was without consequence. Thus, a FR5 TO20 sec schedule of reinforcement was used.

Intravenous Nicotine Self-Administration Procedure

Approximately 1 week after preparation with catheters into the jugular vein, rats (n=8) were trained to self-administer nicotine (0.03 mg/kg per infusion, free base) under an FR5 TO20 sec schedule, similar to that described above for cocaine. Responding on the active lever resulted in delivery of nicotine solution in a volume of 0.1 ml per infusion over a 1 sec period (Razel Scientific Instruments Inc., Stamford, Conn., USA), while responding on the inactive lever had no consequences. Rats were considered to have acquired stable operant responding when they pressed the active lever more than twice the number of times they pressed the inactive lever, received a minimum of six infusions or 90 pellets per 1-h session, with less than 20% variation in the number of reinforcers earned per session. Rats took approximately 2 weeks to establish stable rates of operant responding. All test sessions were conducted for 1 h per day, 5 days per week.

Intracranial Self-Stimulation (ICSS) Reward Threshold Procedure (Markou and Koob, 1991; 1993)

Rats (n=9) were trained to respond according to a modification of the discrete-trial current-threshold procedure of Kornetsky and Esposito (1979). Briefly, a trial was initiated by the delivery of a non-contingent electrical stimulus. This electrical reinforcer had a train duration of 500 ms and consisted of 0.1 msec rectangular cathodal pulses that were delivered at a frequency of 50-100 Hz. The frequency of the stimulation was selected for individual animals so that baseline current-intensity thresholds of each subject were within 50-200 µA, and thus allowed both threshold elevations and lowerings to be detected. The frequency was held constant throughout the experiment. A one-quarter turn of the wheel manipulandum within 7.5 sec of the delivery of the non-contingent electrical stimulation resulted in the delivery of an electrical stimulus identical in all parameters to the non-contingent stimulus that initiated the trial. After a variable inter-trial interval (7.5-12.5 sec, average of 10 sec), another trial was initiated with the delivery of a non-contingent electrical stimulus. Failure to respond to the non-contingent stimulus within 7.5 sec resulted in the onset of the inter-trial interval. Responding during the inter-trial interval delayed the onset of the next trial by 12.5 sec. Current levels were varied in alternating descending and ascending series. A set of three trials was presented for each current intensity. Current intensities were altered in 5 µA steps. In each testing session, four alternating descending-ascending series were presented. The threshold for each series was defined as the midpoint between two consecutive current intensities that yielded "positive scores" (animals responded for at least two of the three trials) and two consecutive current intensities that yielded "negative scores" (animals did not respond for two or more of the three trials). The overall threshold of the session was defined as the mean of the thresholds for the four individual series. Each testing session was .about.30 min in duration. The time between the onset of the non-contingent stimulus and a positive response was recorded as the response latency. The response latency for each test session was defined as the mean response latency of all trials during which a positive response occurred. After establishment of stable ICSS reward thresholds, rats were tested in the ICSS procedure once daily except for the time-course of cocaine's lowering actions on ICSS thresholds when rats were tested at time-points according to the experimental design.

Experiment 3.1: The Effects of MPEP Administration on Cocaine Self-Administration under a Fixed Ratio Schedule of Reinforcement After training in the cocaine self-administration paradigm under a fixed ratio (FR) schedule of reinforcement, as described above, two balanced groups of rats were formed such that their rate of cocaine self-injections did not differ under baseline conditions. From day 10 onwards (the 'escalation' period), access to cocaine self-administration was increased from 1 h to 6 h per daily session in one group of rats (Long Access or LgA rats; n=7). Previous studies have shown that this schedule of access to cocaine self-administration results in a progressive increase or 'escalation' in daily cocaine consumption (Ahmed and Koob, 1997; Ahmed et al. 2001). In the other group (Short Access or ShA rats; n=7), access to cocaine self-administration was maintained at 1 h per daily session. Previous studies have shown that this schedule of access to cocaine self-administration maintains a stable level of daily cocaine consumption. After 22 days of 1 h (ShA) or 6 h (LgA) daily access to cocaine self-administration, both groups of rats received their first MPEP injection. LgA and ShA rats were injected with MPEP (0, 1, 3 or 9 mg/kg) according to a within-subjects Latin-square design, and the daily cocaine self-administration session initiated 30 min later. A minimum of 48 h were allowed between each injection in the Latin-square design, during which LgA and ShA rats had their daily cocaine self-administration session, to ensure that rates of responding for cocaine returned to pre-injection baseline before the next MPEP administration. After completion of the Latin-square, all rats received an injection of MPEP (6 mg/kg), and the daily cocaine self-administration session was initiated 30 min later.

Experiment 3.2: The Effects of MPEP on Cocaine and Nicotine Self-Administration under a Progressive Ratio Schedule of Reinforcement Under a fixed ratio schedule of reinforcement, as described above, an animal responds a 'fixed' number of times on an active lever to obtain a drug infusion. Fixed ratio (FR) schedules of reinforcement provide important information on whether a drug is reinforcing. In contrast, under a progressive ratio (PR) schedule of reinforcement, each time an animal responds on the active lever to receive a drug infusion, the number of times that the animal must subsequently respond to receive the next infusion is progressively increased. By determining how hard an animal is willing to work for a drug, while limiting total intake, the PR schedule allows better separation of motivation for drug consumption from possible satiating effects of cumulative drug doses (Stafford et al. 1998). Such characteristics result in theoretically different interpretations of the factors controlling drug-seeking behavior on a PR compared with a FR. For example, some researchers have recently suggested that FR schedules measure the pleasurable or hedonic effects of a drug (McGregor and Roberts 1995; Mendrek et al. 1998), whereas PR schedules provide a better measure of the incentive or the 'motivation' to obtain a drug (Markou et al., 1993). After acquisition of cocaine or nicotine self-administration under an FR, as described above, rats were switched to a PR schedule of reinforcement in which the following sequence of level presses was required to receive each subsequent infusion of nicotine or cocaine: 5, 10, 17, 24, 32, 42, 56, 73, 95, 124, 161, 208, etc. Rats were injected with MPEP (0, 1, 3 or 9 mg/kg) 30 min prior to each PR session. All PR sessions lasted for 3 h. All subjects reached breaking-points during the 3 hour session. Break-point is defined as the highest ratio achieved before the session was terminated; the session was terminated if the subject failed to earn a drug infusion during one hour.

Experiment 3.3: The Effects of MPEP on Cocaine-Induced Lowering of ICSS Thresholds MPEP was shown in Example 3.2 to decrease nicotine self-administration, under an FR, in rats and mice. The studies in this Example (results described below) demonstrate that MPEP decreased cocaine and nicotine self-administration in rats (in the case of nicotine in mice also) under a FR, and decreased cocaine and nicotine self-administration in rats under a PR schedule of reinforcement. One possible mechanism by which MPEP may have decreased cocaine self-administration behavior was by decreasing the hedonic actions of cocaine. Cocaine-induced lowering of ICSS thresholds represents an accurate measure of cocaine's hedonic and euphorigenic actions. Thus, to test the hypothesis that MPEP attenuated the hedonic actions of cocaine, we examined whether MPEP blocked cocaine-induced lowering of ICSS thresholds. The dose of cocaine (10 mg/kg) used in these studies was chosen based on previous observations that this dose of cocaine induced maximal threshold lowering without affecting performance in the ICSS procedure used in the present study (Kenny et al., 2002b; Markou & Koob 1992), and was equivalent to the amount of cocaine consumed by ShA rats during their daily 1 h access to cocaine self-administration. Rats (n=9) were prepared with ICSS electrodes as described above, and trained in the ICSS procedure until stable thresholds were achieved ($\leq$10% variation in thresholds over 5 consecutive days). To determine if MPEP attenuated the magnitude of cocaine's threshold-lowering effects, rats were injected with MPEP (0, 3, 6 or 9 mg/kg) according to a within-subjects Latin-square design 30 min prior to initiation of the ICSS session. All rats then received a saline injection 20 min later, 10 min prior to initiation of the ICSS session. A period of 72 h were allowed to elapse between each injection day in the Latin-square design, during which daily ICSS thresholds continued to be assessed to ensure that ICSS thresholds returned to pre-injection baseline before the next drug administration. After completion of the Latin-square, all rats received an injection of MPEP (1 mg/kg), 30 min prior to initiation of the ICSS session, and a saline injection 10 min prior to the initiation of the ICSS session. After this treatment regimen, rats were once again injected with MPEP (0, 3, 6 or 9 mg/kg) according to a within-subjects Latin-square design 30 min prior to initiation of the ICSS session. All rats then received a cocaine (10 mg/kg) injection instead of saline 20 min later, 10 min prior to initiation of the ICSS session. A period of 72 h were allowed between each injection day in the Latin-square design, during which daily ICSS thresholds continued to be assessed to ensure that ICSS thresholds returned to pre-injection baseline before the next drug administration. After completion of the Latin-square, all rats received an injection of MPEP (1 mg/kg), 30 min prior to initiation of the ICSS session, and a cocaine (10 mg/kg) injection 10 min prior to the initiation of the ICSS session.

To determine if MPEP attenuated the duration of cocaine's threshold-lowering effects, rats were first injected with either sterile water or MPEP (3 mg/kg), then 20 min later with either saline or cocaine (10 mg/kg) 10 min prior to initiation of the first ICSS session. Rats received all injections according to a within-subjects Latin-square design, such that each rat received the four possible drug combinations (water-saline; water-cocaine; MPEP-saline; MPEP-cocaine). ICSS thresholds were then assessed 10, 40, 70 and 100 min after the second (saline or cocaine) injection. A period of 72 h were allowed to elapse between each injection day in the Latin-square design, during which daily ICSS thresholds continued to be assessed to ensure that ICSS thresholds returned to pre-injection baseline levels before the next drug administration.

Experiment 3.4: Effects of the mGluR2/3 Antagonist on Nicotine Self-Administration under a Fixed Ratio Schedule.

Previously, the Group II metabotropic glutamate receptor antagonist LY341495 was shown to attenuate nicotine withdrawal, as measured by decreased elevations in ICSS thresholds during spontaneous nicotine withdrawal in rats (Kenny et al., 2003c). To examine whether mGlu2/3 receptors also play a role in regulating the reinforcing actions of nicotine, we examined whether LY341495 decreased nicotine self-administration under a FR schedule of reinforcement. After training in the nicotine self-administration paradigm, as described above, rats were injected with LY341495 (0, 0.1, 0.5, 1, 3 or 5 mg/kg) according to a within-subjects Latin-square design, and the daily nicotine self-administration session was initiated 30 min later. A minimum of 48 h were allowed between each injection in the Latin-square design, during which rats had their daily nicotine self-administration session, to ensure that rates of responding for nicotine returned to pre-injection baseline before the next LY341495 administration.

Experiment 3.5: The Effects of the Drug Combination LY341495 and MPEP on Nicotine Self-Administration under a FR Schedule (Assessing Consumption) and a PR Schedule (Assessing Motivation for Drug Administration)

Previously, MPEP was shown to decrease nicotine self-administration under a FR schedule in rats and mice (Paterson et al., 2003). The present studies demonstrate (results described below) that LY341495 similarly decreased nicotine self-administration in rats under a FR schedule. Thus, we hypothesized that simultaneous inhibition of mGlu5 and mGlu2/3 receptors, by MPEP and LY341495 respectively, may have additive inhibitory effects on nicotine self-administration in rats. Here we have shown (results described below) that LY341495 (0.5 mg/kg) decreased nicotine self-administration by approximately 35 percent. Thus: 1) we injected rats with this dose of LY341495 (0.5 mg/kg), in combination with a dose of MPEP (1 mg/kg) previously shown to have no effects on nicotine (Paterson et al., 2003) or cocaine (present results from Experiment 1 reported here) self-administration, and assessed nicotine self-administration behavior under a FR schedule of reinforcement (30 minutes pretreatment); 2) we injected rats (30 min pretreatment) also with a dose of LY341495 (1 mg/kg) that was shown to have no effects on nicotine self-administration when administered alone in combination with 1 mg/kg MPEP (this dose of MPEP was also shown to have no effect on nicotine self-administration when administered alone) and assessed the effects of this drug combination treatment on nicotine self-administration; and 3) finally, we injected rats with the drug combination treatment of 1 mg/kg LY341494 and 9 mg/kg MPEP (dose of MPEP that decreases nicotine self-administration when administered on its own; Paterson et al. 2003) and examined the effects on nicotine self-administration under a progressive ratio schedule of reinforcement (30 min pretreatment).

Statistical Analyses

During the escalation phase of the cocaine self-administration experiment, the number of cocaine responses in ShA and LgA rats during the 23 days prior to the first MPEP injection was analyzed by two-factor repeated measures analyses of variance (ANOVA). During the MPEP treatment phase, percent change from baseline number of cocaine responses was calculated by expressing the number of cocaine responses after MPEP treatment as a percentage of the baseline number of cocaine responses. For the ICSS experiments, mean raw thresholds and response latencies (±SEM) are presented for each experiment in the results section. For all ICSS experiments, percentage change from baseline reward threshold was calculated by expressing the drug-influenced raw threshold scores as a percentage of the baseline thresholds. The baseline thresholds were the mean of the thresholds obtained on the three days before the first MPEP injection. For the first ICSS experiment (the effects of MPEP on cocaine-induced threshold lowering), percentage of baseline scores were subjected to two-factor repeated-measures ANOVA, with MPEP dose (1-9 mg/kg) and cocaine dose (0 or 10 mg/kg) as the two within-subjects factors. For the second ICSS experiment (the effects of MPEP on the duration of cocaine-induced threshold lowering), percentage of baseline scores were subjected to three-factor repeated-measures ANOVA, with MPEP (0 or 3 mg/kg), cocaine (0 or 10 mg/kg) and time after second injection (10, 40, 70 and 100 min), as the three within-subjects factors. For all ICSS experiments, response latency data were analyzed in the same manner as the threshold data. The baseline number of nicotine responses was the mean number of nicotine responses on the five days prior to the first LY341495 injection. During the LY341495 treatment phase, percent change from baseline number of nicotine responses was calculated by expressing the number of nicotine responses after LY341495 treatment as a percentage of the baseline number of nicotine responses. Progressive ratio data were expressed as highest ratio attained (i.e., break-point) or number of infusions earned (data expressed as raw values). After statistically significant effects in the ANOVAs, post-hoc comparisons among means were conducted with Fisher's LSD test. The level of significance was set at 0.05.

Results

Figure 9:
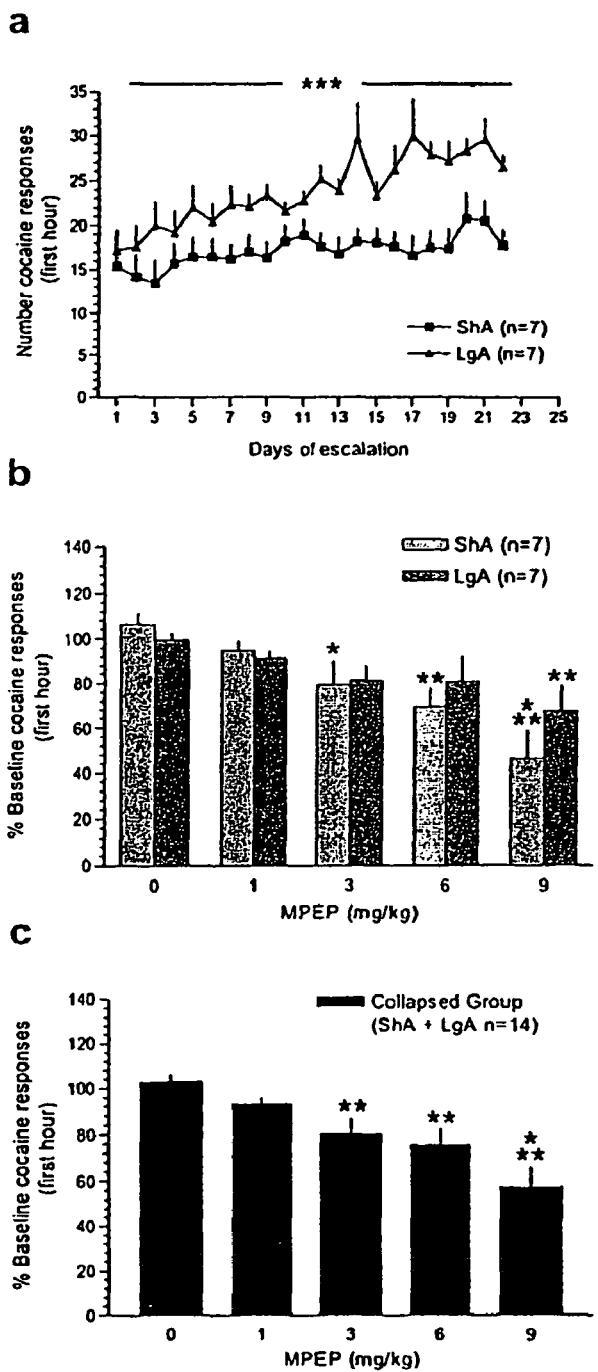
FIGS. 9A-9B illustrate the effects of MPEP administration on cocaine responding in Short Access (ShA) and Long Access (LgA) rats.

Experiment 3.1: The Effects of MPEP Administration on Cocaine Self-Administration under a Fixed Ratio Schedule of Reinforcement As can be seen in FIG. 9A, the number of cocaine responses progressively increased in LgA rats compared to ShA rats during the escalation phase. This effect was reflected in a statistically significant main effect of Daily access (1 or 6 h) ($F_{(1,21)}=10.96$, $p<0.01$), a significant main effect of Days of treatment ($F_{(12,252)}=10.96$, $p<0.001$), and a significant Access×Days interaction ($F_{(12,252)}=1.69$, $p<0.05$). MPEP (1-9 mg/kg) decreased cocaine self-administration in ShA and LgA rats ($F_{(4,48)}=9.34$, $p<0.001$) (FIG. 9B). Post-hoc analysis demonstrated that 3 ($p<0.05$), 6 ($p<0.01$) and 9 ($p<0.001$) mg/kg MPEP significantly decreased cocaine responding in ShA rats (FIG. 9B). Post-hoc analysis demonstrated that only the highest dose of MPEP (9 mg/kg) significantly decreased cocaine responding in LgA rats ($p<0.01$) (FIG. 9B). However, there was no Dose×Access interaction ($F_{(12,252)}=0.97$, N.S.). When cocaine responding for the ShA and LgA rats was collapsed, MPEP significantly decreased cocaine responding ($F_{(4,52)}=9.36$, $p<0.001$) (FIG. 9C), and post-hoc analysis demonstrated that 3 ($p<0.01$), 6 ($p<0.01$) and 9 ($p<0.001$) mg/kg MPEP significantly decreased cocaine responding in the collapsed group (FIG. 9C).

Experiment 3.2: The Effects of MPEP on Cocaine and Nicotine Self-Administration under a Progressive Ratio Schedule of Reinforcement.

Figure 10:
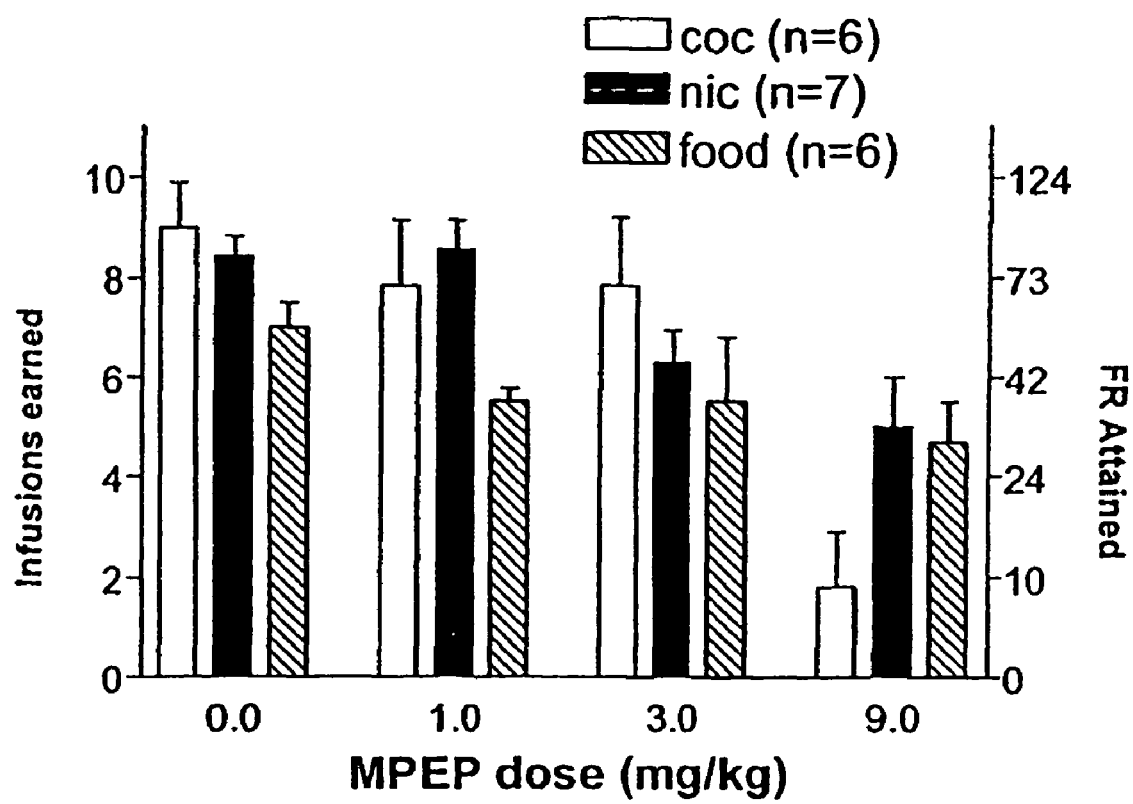
FIG. 10 illustrates the effects of MPEP on cocaine-, nicotine- and food-maintained responding under a progressive-ratio schedule of reinforcement. Data are presented as the mean (±SEM) number of infusions/food pellets earned after MPEP pretreatment (left ordinal axis). The right ordinal axis shows the corresponding final ratios (i.e., break-points) reached.

A two-way ANOVA with MPEP dose and reinforcer as the two factors revealed a significant interaction effect of the two factors [$F(6,48)=3.95$, $p<.01$], a main effect of MPEP [$F(3,48)=3.95$; $p<0.01$] and no significant main effect of reinforcer [$F(2,16)=1.41$, $p=0.27$]. As can be seen in FIG. 10, MPEP (1-9 mg/kg) decreased responding for cocaine (significant effect of MPEP in a one-way follow-up ANOVA after a significant interaction effect in the overall ANOVA: $F(3,15)=12.76$; $p<0.001$) and nicotine (significant effect of MPEP in a one-way follow-up ANOVA after a significant interaction effect in the overall ANOVA: $F(3,18)=11.28$; $p<0.001$) under a progressive ratio schedule of reinforcement, while having no statistically significant effect on responding for food (no effect of MPEP on food responding in a one-way follow-up ANOVA after a significant interaction effect in the overall ANOVA: $F(3,15)=2.84$; $p=0.07$. Because progressive ratio schedules of reinforcement provide a measure of an animals 'motivation' to obtain the drug, these data demonstrate that MPEP decreased the motivation of rats to obtain cocaine or nicotine without affecting their motivation for food, thus demonstrating the specificity of the effects.

Figure 11:
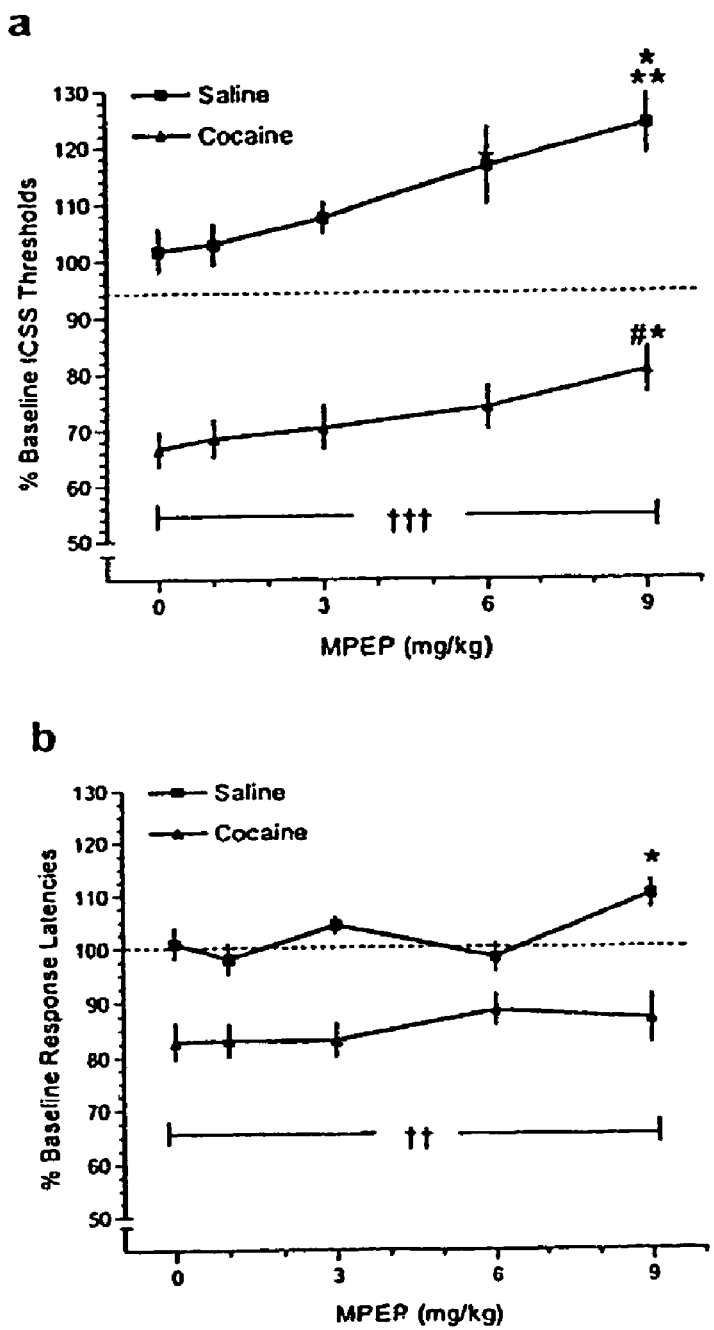
FIG. 11 illustrates the effects of MPEP administration on the magnitude of cocaine-induced lowering of ICSS reward thresholds (a) and effects on response latencies in the same procedure (b). The data are expressed as percent of baseline (mean±SEM). *P<0.05, ***p<0.001 from control; #p<0.05 compared with rats similarly treated with the same dose of MPEP, but did not receive cocaine.

Experiment 3.3: The Effects of MPEP on Cocaine-Induced Lowering of ICSS Thresholds As can be seen in FIG. 11A, cocaine (10 mg/kg) significantly lowered ICSS thresholds ($F_{(1,8)}=98.21$, $p<0.001$). In contrast, MPEP significantly elevated ICSS thresholds ($F_{(4,32)}=8.22$, $p<0.001$), and post-hoc analysis demonstrated that 6 ($p<0.05$) and 9 ($p<0.01$) mg/kg MPEP significantly elevated ICSS thresholds. There was no cocaine×MPEP interaction ($F_{(4,32)}=0.75$, N.S.). Further analyses based on our a-priori hypotheses revealed that ICSS thresholds were significantly elevated in cocaine-treated rats that previously received MPEP (9 mg/kg) compared to cocaine-treated rats that received vehicle injection ($p<0.05$) (FIG. 11A). However, ICSS thresholds in cocaine-treated rats that previously received MPEP (9 mg/kg) were still significantly lowered compared to saline-treated rats pretreated with vehicle ($p<0.001$). Cocaine (10 mg/kg) significantly decreased ICSS response latencies ($F_{(1,8)}=42.13$, $p<0.001$) (FIG. 11B). In contrast, MPEP significantly increased response latencies ($F_{(4,32)}=2.8$, $p<0.05$). Further analysis demonstrated that only the highest dose of MPEP (9 mg/kg) significantly increased response latencies ($p<0.05$) (FIG. 11B). There was no cocaine×MPEP interaction ($F_{(4,32)}=2.16$, N.S.).

Figure 12:
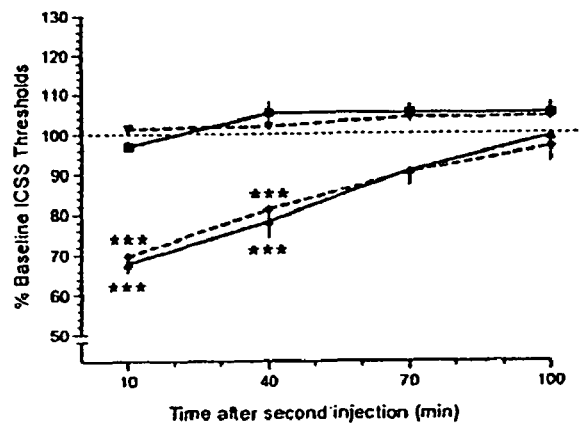
FIG. 12 illustrates the effects of MPEP administration on the duration of cocaine-induced lowering of ICSS reward thresholds (a) and the effects on response latencies (b). The data are expressed as percent of baseline (mean±SEM). ***p<0.001 from control.
Figure 12:
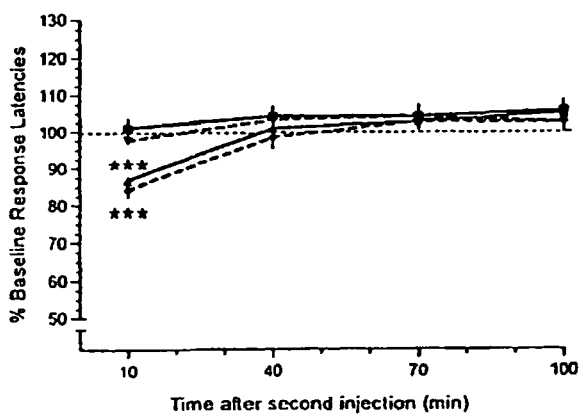

As can be seen in FIG. 12A, cocaine (10 mg/kg) significantly lowered ICSS thresholds ($F_{(1,8)}=62.73$, $p<0.001$). This cocaine-induced lowering in ICSS thresholds was time-dependent; cocaine×time interaction ($F_{(3,24)}=30.75$, $p<0.001$). Post-hoc analysis revealed that ICSS thresholds were significantly lowered in cocaine-treated rats, pretreated with vehicle, at 10 ($p<0.001$) and 40 ($p<0.001$) min after cocaine injection compared to saline-treated rats pretreated with vehicle. MPEP (3 mg/kg) had no effect on ICSS thresholds at any time-point ($F_{(1,8)}=0.002$, N.S.), and there was no cocaine×MPEP×time interaction ($F_{(3,24)}=1.02$, N.S.). Post-hoc analysis revealed that ICSS thresholds were significantly lowered in cocaine-treated rats, pretreated with MPEP, at 10 ($p<0.001$) and 40 ($p<0.001$) min after cocaine injection compared to vehicle-saline-treated rats. Cocaine significantly decreased ICSS response latencies ($F_{(1,8)}=12.65$, $p<0.01$) (FIG. 12B). This cocaine-induced lowering in response latencies was also time-dependent; cocaine×time interaction ($F_{(3,24)}=6.62$, $p<0.01$). Post-hoc analysis revealed that response latencies were significantly decreased in cocaine-treated rats, pretreated with vehicle, at 10 ($p<0.001$) min after cocaine injection compared to saline-treated rats pretreated with vehicle. MPEP (3 mg/kg) had no effect on response latencies at any time-point ($F_{(1,8)}=2.67$, N.S.), and there was no cocaine×MPEP×time interaction ($F_{(3,24)}=0.14$, N.S.). Post-hoc analysis revealed that ICSS thresholds were significantly lowered in cocaine-treated rats, pretreated with MPEP, at 10 ($p<0.001$) min after cocaine injection compared to vehicle-saline-treated rats.

Experiment 3.4: Effects of the mGluR2/3 Antagonist on Nicotine Self-Administration under a Fixed Ratio Schedule.

Figure 13:
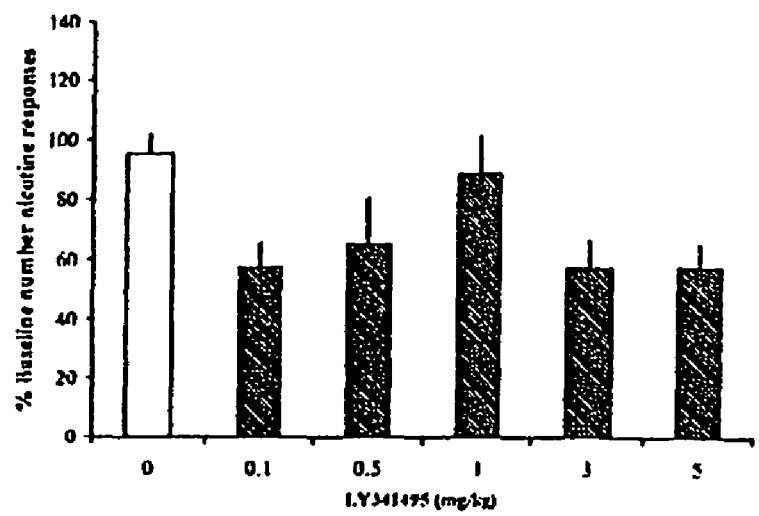
FIG. 13 illustrates the effects of LY341495 (0.1-5 mg/kg) administration on nicotine responding in rats. The data are expressed as percent of baseline responding (mean±SEM).

As seen in FIG. 13, LY341495 (0.1-5 mg/kg) decreased nicotine self-administration under a FR schedule ($F_{(5,35)}=3.75$, $p<0.01$). Post-hoc analysis demonstrated that 0.1 ($p<0.01$), 0.5 ($p<0.05$), 3 ($p<0.01$) and 5 ($p<0.01$) mg/kg LY341495 significantly decreased nicotine responding (FIG. 13).

Experiment 3.5: The Effects of the Drug Combination LY341495 and MPEP on Nicotine Self-Administration under a FR Schedule and a PR Schedule.

Figure 14:
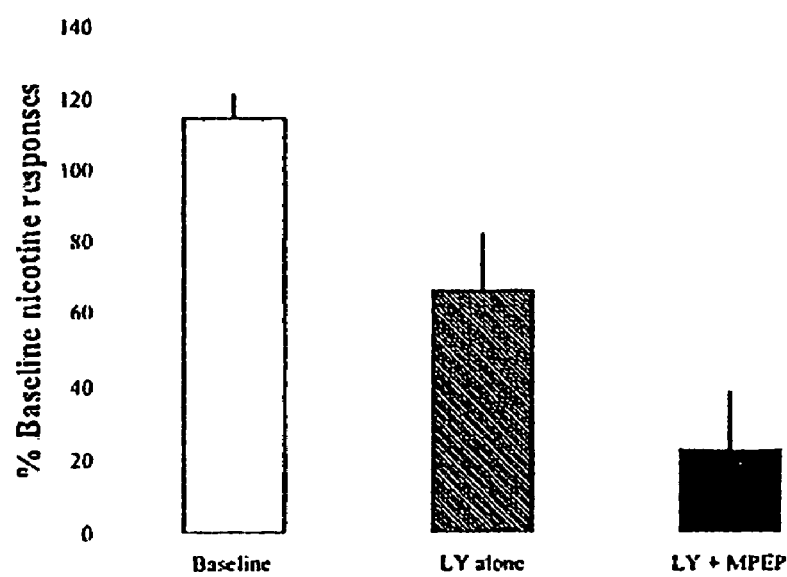
FIG. 14 illustrates the effects of LY341495 (0.5 mg/kg) alone, or in combination with a dose of MPEP (1 mg/kg) previously shown (see FIG. 13 above) to have no effect by itself on cocaine consumption, on nicotine responding in rats. The data are expressed as percent of baseline responding (mean±SEM).

As seen in FIG. 14, a combination of LY341495 (0.5 mg/kg) and a dose of MPEP (1 mg/kg), shown in Example 2 above to have no effects on nicotine (See also, Paterson et al., 2003) or cocaine self-administration, significantly decreased responding for nicotine ($F_{(2,17)}=8.6$, $p<0.01$).

Figure 15:
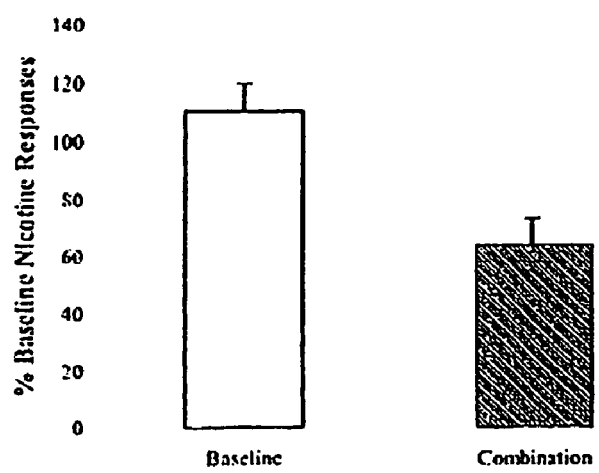
FIG. 15 illustrates the effects of LY341495 (1 mg/kg) combined with MPEP (1 mg/kg) on nicotine responding in rats. The data are expressed as percent of baseline responding (mean±SEM).
Figure 16:
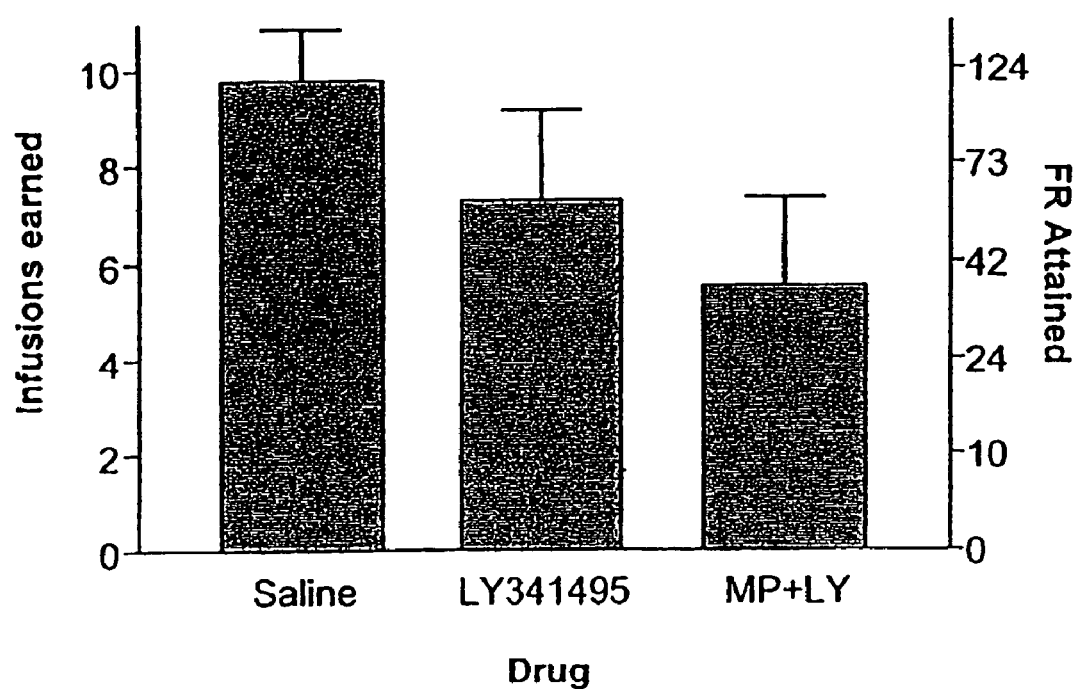
FIG. 16 illustrates the effects of LY341495 (1 mg/kg) and of the drug combination LY341495 and MPEP (1 mg/kg and 9 mg/kg, respectively) on break-points (i.e., highest fixed ratio attained depicted on the right y-axis) and number of nicotine injections earned (depicted on the left y-axis) under a progressive ratio of reinforcement that reflects the motivation for drug-taking behavior. MPEP potentiated the break-point decreases induced by LY341495). Data are presented as the mean (±SEM) number of infusions earned after the drug treatments (left ordinal axis). The right ordinal axis shows the corresponding final ratios (i.e., break-points) reached.

Post-hoc analysis demonstrated that LY341495 (0.5 mg/kg) alone ($p<0.05$), and the combination of LY341495 (0.5 mg/kg) and MPEP (1 mg/kg) ($p<0.01$) significantly decreased nicotine self-administration. The combination of LY341495 (0.5 mg/kg) and MPEP (1 mg/kg) decreased nicotine self-administration by a greater magnitude that LY341495 (0.5 mg/kg) alone, although this effect just failed to reach statistical significance ($p=0.053$). Similarly, a dose of LY341495 (1 mg/kg), combined with a behaviorally inactive dose of MPEP (1 mg/kg) also decreased nicotine self-administration (FIG. 15). Finally, additional data (FIG. 16) indicated that the combination of 9 mg/kg MPEP together with 1 mg/kg LY341494 significantly decreased nicotine self-administration under a progressive ratio schedule of reinforcement.

Discussion

Recent observations from our laboratory have shown that repeated extended (6 h) access cocaine self-administration resulted in a progressive increase or 'escalation' in daily cocaine consumption in LgA rats (Ahmed and Koob, 1998; Ahmed et al., 2002). In contrast, ShA rats with restricted (1 h) access to cocaine self-administration maintained a stable pattern of daily cocaine consumption. The present data demonstrate that the mGlu5 receptor antagonist MPEP decreased cocaine consumption similarly in rats with ShA and LgA rats suggesting that blockade of mGluR5 receptors may decrease drug use in both drug-dependent and non-drug-dependent individuals. Previously, MPEP was shown to decrease cocaine self-administration in wild-type control mice (Chiamulera et al., 2001), and genetically modified mice in which the mGlu5 deleted failed to acquire cocaine self-administration behavior, even though responding for food reinforcement was unaltered in these mice (Chiamulera et al., 2001). Similarly, Example 2 above illustrates that MPEP decreases nicotine self-administration in rats and mice. Thus, the data in this Example are consistent with an important role for mGlu5 receptors in regulating cocaine and nicotine self-administration behavior in both drug-dependent and non-drug dependent individuals. However, MPEP decreased cocaine consumption by a similar magnitude in ShA and LgA rats. Thus, it is unlikely that the escalation in cocaine intake observed in LgA rats was associated with alterations in mGlu5 receptor regulation of cocaine self-administration behavior.

The hedonic actions of cocaine are thought to play an important role in establishing and maintaining cocaine self-administration behavior (Stewart et al., 1984; Kenny et al., 2003a). Cocaine-induced lowering of ICSS thresholds is considered an accurate measure of cocaine's hedonic actions. Interestingly, doses of MPEP (1-9 mg/kg) that decreased cocaine self-administration did not attenuate the magnitude of the lowering in ICSS thresholds observed after systemic cocaine administration. Similarly, MPEP (3 mg/kg) did not attenuate the duration of time that cocaine lowered ICSS thresholds. Because cocaine-induced lowering of ICSS thresholds is an accurate measure of cocaine-induced facilitation of brain reward function, these observations suggest that MPEP decreased cocaine consumption even though the hedonic impact of cocaine remained intact. It is important to note that higher doses of MPEP (6-9 mg/kg) alone elevated ICSS thresholds, suggesting that mGlu5 receptors positively regulate baseline brain reward function. However, a low dose of MPEP (3 mg/kg), that had no effect on ICSS thresholds alone, significantly decreased cocaine self-administration behavior. Thus, it is unlikely that MPEP decreased cocaine self-administration behavior by decreasing baseline brain reward function and thereby inducing an aversive behavioral state. Overall, the data in this Example suggest that MPEP decreased cocaine self-administration (i.e., consumption) by a mechanism independent of cocaine's hedonic actions.

One possible explanation for the above observations is that MPEP decreased the 'motivation' of rats to self-administer cocaine, but did not alter cocaine-induced increases in brain reward function (i.e., cocaine-induced euphoria). To test this possibility, we examined whether MPEP would decrease responding for cocaine and nicotine under a progressive ratio (PR) schedule of reinforcement. PR schedules provide a measure of an animals 'motivation' to obtain a drug of abuse. Interestingly, MPEP significantly lowered the break point for cocaine and nicotine under a PR schedule of reinforcement. This observation suggests that MPEP decreased the motivation of rats to obtain cocaine and nicotine, and thus leads to decreases in drug consumption.

Next, we examined whether blockade of mGlu2/3 receptors would decrease nicotine self-administration in rats similar to blockade of mGlu5 receptors. Example 1 above, illustrates that blockade of mGlu2/3 receptors by administration of the mGlu2/3 receptor antagonist LY341495, attenuated the depression-like aspects of nicotine withdrawal in rats. The present data demonstrated that LY341495, an antagonist at mGlu2/3 receptors, decreased nicotine consumption in rats, suggesting that blockade of mGluR2/3 receptors decreased the reinforcing effects of nicotine. Most interestingly, co-administration of a dose of MPEP (1 mg/kg) that has no effects on cocaine or nicotine self-administration potentiated the inhibitory effects of LY341495 (0.5 mg/kg or 1 mg/kg) on nicotine self-administration. Further, the combination of 9 mg/kg MPEP that decreases either cocaine or nicotine self-administration when administered alone, when combined with 1 mg/kg LY341495, also decreased nicotine self-administration under a progressive ratio schedule of reinforcement, and the effect was larger than with any one drug alone clearly demonstrating a potentiation of these effects. These observations suggest that simultaneous blockade of mGlu2/3 and mGlu5 receptors may have better efficacy in the treatment of drug addiction than blockade of either receptor subtype alone, and that such simultaneous blockade of mGlu2/3 and mGlu5 receptors decreases both drug consumption and the motivation to engage in drug-taking behaviors.

Further, as illustrated in Example 1 above, blockade of mGluR2/3 receptors reverses the affective depression-like aspects of nicotine withdrawal. Thus, pharmacological treatments with dual antagonist actions at mGlu2 and/or mGluR3, and mGlu5 receptors: 1) decrease consumption of drugs of abuse, such as nicotine and cocaine to a larger extent than blockade of either one receptor alone and 2) reverse the affective aspects of drug withdrawal, and possibly of drug dependence. These effects on both drug consumption and drug withdrawal may contribute to increased abstinence rates among tobacco smokers, and drug users and abusers. Finally, 3) pharmacological treatments with dual antagonist actions at mGlu2/3 and mGlu5 receptors may be effective treatments for non-drug-induced depressions also.

REFERENCES CITED IN EXAMPLE 3

Chiamulera, C., Epping-Jordan, M. P., Zocchi, A., Marcon, C., Cottiny, C., Tacconi, S., Corsi, M., Orzi, F., Conquet, F., 2001, Nat Neurosci, 4, 873-874.
Esposito, R. U., Motola, A. H., Kornetsky, C., 1978, Pharmacol Biochem Behav, 8, 437-439.
Frank, R. A., Martz, S., Pommering, T., 1988, *Pharmacol Biochem Behav*, 29, 755-758.
Harris, G. C., Aston-Jones, G., 2003, *Neuropsychopharmacology*, 28, 73-76.
Harrison, A. A., Liem, Y. T. and Markou, A. (2001), Neuropsychopharmacology, 25, 55-71.
Kalivas, P. W., Duffy, P., 1998, J Neurochem, 70, 1497-1502.
Kenny, P. J., Polis, I., Koob, G. F., Markou, A., 2003b, *Eur J Neurosci,* 17, 191-195.
Kenny P J, Gasparini F, Markou A. (2003c), J Pharmacol Exp Ther. 2003 Jun. 12 [Epub ahead of print].
Kokkinidis, L., McCarter, B. D., 1990, Pharmacol Biochem Behav, 36, 463-471.
Laviolette, S. R., van der Kooy, D., 2003, Psychopharmacology (Berl), 166, 306-313.
Mansvelder, H. D., McGehee, D. S., 2000, Neuron, 27, 349-357.
Markou, A. and Kenny, P. J. (2002), *Neurotoxicity Research*, 4(4), 297-313.
Markou, A., Koob, G. F., 1992, Physiol Behav, 51, 111-119.
Markou, A. and Koob, G. F. (1993) Intracranial self-stimulation thresholds as a measure of reward. In: A. Sahgal (Ed.), *Behavioural Neuroscience: A Practical Approach, vol. 2*, IRL Press, Oxford, pp. 93-115.
Markou, A., Kosten, T. R. and Koob, G. F. (1998), Neuropsychopharmacology, 18(3),135-174.
McGeehan, A. J., Olive, M. F., 2003, Synapse, 47, 240-242.
Popik, P., Wrobel, M., 2002, Neuropharmacology, 43, 1210-1217.
Stewart, J., de Wit, H., Eikelboom, R., 1984, Psychol Rev, 91, 251-268.
Ungless, M. A., Whistler, J. L., Malenka, R. C., Bonci, A., 2001, Nature, 411, 583-587.
Wolf, M. E., 2003, Methods Mol Med, 79, 13-31.

Example 4

The Selective Serotonin Reuptake Inhibitor Paroxetine Combined with a Serotonin (5-HT)1a Receptor Antagonist Reversed Reward Deficits Observed During Amphetamine Withdrawal in Rats This example illustrates that the co-administration of the 5-HT1A receptor antagonist p-MPPI and the selective serotonin reuptake inhibitor paroxetine decreases the magnitude and reduces the duration of amphetamine withdrawal-induced reward deficits.

Rationale: "Diminished interest or pleasure" in rewarding stimuli is an affective symptom of amphetamine withdrawal, and a core symptom of depression. An operational measure of this symptom is elevation of brain stimulation reward thresholds during drug withdrawal. Data indicated that increasing serotonin neurotransmission by co-administration of the selective serotonin reuptake inhibitor (SSRI) fluoxetine and the serotonin-1A receptor antagonist p-MPPI reversed reward deficits observed during drug withdrawal (Harrison et al. 2001, incorporated in its entirety herein by reference). Objectives: We further tested the hypothesis that increased serotonergic neurotransmission would alleviate this affective symptom of amphetamine withdrawal using paroxetine, a more selective SSRI than fluoxetine.

Methods: A discrete-trial current-threshold self-stimulation procedure was used to assess brain reward function. The effects of paroxetine and p-MPPI alone and in combination were assessed in non-drug withdrawing animals. We assessed also the effects of paroxetine and p-MPPI alone and in combination on reward deficits associated with amphetamine withdrawal. Results: Paroxetine or p-MPPI alone had no effect on thresholds, while the co-administration of p-MPPI and paroxetine elevated thresholds in non-withdrawing rats. Amphetamine withdrawal resulted in threshold elevations. The co-administration of p-MPPI and paroxetine reduced the duration of amphetamine withdrawal-induced reward deficits.

Conclusions: Increased serotonergic neurotransmission decreased brain reward function in non-withdrawing rats, while the same treatment reversed reward deficits associated with amphetamine withdrawal. Considering the greater selectivity of paroxetine compared to fluoxetine for the serotonin transporter, these results strongly indicate that the affective symptoms of amphetamine withdrawal, similarly to non-drug-induced depressions, may be, in part, mediated through reduced serotonergic neurotransmission.

The withdrawal syndrome experienced after the cessation of amphetamine administration is characterized by affective symptoms including "diminished interest or pleasure" in rewarding stimuli (American Psychiatric Association 1994; Markou and Kenny 2002). The symptom of "diminished interest or pleasure" is also a core symptom of depression and a negative symptom of schizophrenia (American Psychiatric Association 1994). Brain reward threshold elevation is an operational measure of this symptom because it reflects reduced sensitivity to rewarding electrical stimuli. In rats, withdrawal from a variety of drugs of abuse, belonging to diverse pharmacological classes such as nicotine (Epping-Jordan et al. 1998; Harrison et al. 2001), amphetamine (Leith and Barrett 1976; Lin et al. 1999; Paterson et al. 2000; Harrison et al. 2001), cocaine (Markou and Koob 1991), morphine (Schulteis et al. 1994), ethanol (Schulteis et al. 1995) and phencyclidine (Spielewoy and Markou 2003) elevated brain stimulation reward thresholds in rats.

Reduced serotonergic neurotransmission has been implicated in the etiology of non-drug induced depression. Evidence in favor of this hypothesis includes demonstrations of the efficacy of serotonergic antidepressant treatments, reduced cerebrospinal fluid levels of serotonin metabolites, endocrine measures reflecting reduced serotonergic neurotransmission and the exacerbation of depressive symptomatology seen after serotonin depletion in depressed patients (for reviews, Caldecott-Hazard et al. 1991; Markou et al. 1998). Recent advances in the treatment of depression indicate that the co-administration of pindolol accelerates the delayed onset of the antidepressant action of selective serotonin reuptake inhibitors (SSRIs) (Rickets et al. 1989; Blier and de Montigny, 1999; Bordet et al. 1998; Zanardi et al. 1998; McAskill et al. 1998). It has been hypothesized that the acceleration of the antidepressant action of SSRIs may be through the 5-$HT_{1A}$ receptor antagonist action of pindolol, although this drug has widespread effects through antagonist actions at 5-$HT_{1A}$, 5-$HT_{1E}$, and β-adrenergic receptors (Assie and Koek 1996; Bourin et al. 1998; Gobert and Millan 1999) and partial agonist actions at β-adrenergic receptors (Clifford et al. 1998; Gobert and Millan 1999; Pauwels and Palmier 1994). In vivo microdialysis work demonstrated that the acute co-administration of a 5-$HT_{1A}$ receptor antagonist together with an SSRI rapidly elevated forebrain serotonin dialysate levels beyond levels seen after acute SSRI treatment alone (Auerbach and Hjorth 1995; Hjorth 1993; Kreiss and Lucki 1995; Artigas et al 1996; Blier and de Montigny 1994; however, see Cremers et al. 2000).

We recently reported that the co-administration of 4-(2'-methoxy-phenyl)-1-[2'-(n-(2"-pyridinyl)-p-iodobenzamido]-ethyl-piperazine (p-MPPI), a 5-$HT_{1A}$ receptor antagonist (Kung et al. 1994), and fluoxetine, an SSRI (Wong et al. 1995), reversed reward deficits observed during either nicotine or amphetamine withdrawal (i.e. increased reward) without affecting the somatic signs of nicotine withdrawal (Harrison et al. 2001). These data indicate that enhancement of serotonergic neurotransmission may selectively alleviate affective symptoms of drug withdrawal. Further, the above results together with a related set of studies demonstrated that the effects of serotonergic manipulations on brain reward mechanisms depend upon the hedonic state of the subjects (Harrison et al. 2001; Harrison and Markou 2001).

Paroxetine, a phenylpiperidine compound, acts as a selective serotonin reuptake inhibitor that is chemically and pharmacokinetically distinct, and more selective and potent in the inhibition of serotonin reuptake than other SSRIs, such as fluoxetine, sertraline, clomipramine and fluvoxamine (Tulloch and Johnson 1992). SSRIs are hypothesized to alleviate the symptoms of depression through enhancement of serotonergic transmission (Tignol 1993; Bourin et al. 2001). However, SSRIs, such as fluoxetine, exert effects on the noradrenaline transporter also; noradrenaline is another transmitter system implicated in depression (Caldecott-Hazard et al. 1991; Markou et al. 1998). Thus, the purpose of the present study was to extend our previous findings with fluoxetine by demonstrating that a more selective and chemically distinct SSRI, paroxetine, alleviates also the affective aspects of drug withdrawal and thus further demonstrates a serotonergic contribution to these effects.

In summary, based on evidence that: 1) pretreatment with a 5-$HT_{1A}$ receptor antagonist potentiated the increase of forebrain serotonin levels induced by paroxetine administration (Romero et al. 1996); 2) co-administration of pindolol with paroxetine accelerates the onset of the antidepressant effects of paroxetine in humans (Bordet et al. 1998; Zanardi et al. 1998), and 3) our previous findings that fluoxetine combined with a 5-$HT_{1A}$ receptor antagonist reversed amphetamine withdrawal, it was hypothesized here that the co-administration of the 5-$HT_{1A}$ receptor antagonist p-MPPI with paroxetine would alleviate amphetamine withdrawal-induced reward deficits in rats. Thus, the present series of experiments assessed: 1) the effects of paroxetine on brain reward thresholds under baseline conditions; 2) the effects of p-MPPI and the co-administration of p-MPPI+paroxetine on thresholds under baseline conditions; and 3) the effects of these drug treatments on reward deficits induced by amphetamine withdrawal.

Materials and Methods

Subjects

Male Wistar rats (Charles River, Hollister, Calif.) (300-320 g at the start of the experiments) were housed in pairs in a temperature and humidity controlled environment with a 12 hr light/dark cycle. Food and water were available ad libitum. A different set of subjects was used for each experiment. All subjects were treated in accordance with the National Institutes of Health "Guide for the Care and Use of Laboratory Animals," and the animal facilities and the experimental protocols were in accordance with the Association for the Assessment and Accreditation of Laboratory Animal Care. Most of the behavioral testing was conducted during the light phase of the subjects' light/dark cycle, unless otherwise dictated by the experimental design due to time-course assessment of behavioral parameters.

Apparatus

The experimental apparatus consisted of 16 Plexiglas chambers (30.5×30×17 cm) (Med Associates Inc., St. Albans, Vt.) encased in sound-attenuating boxes (San Diego Instruments, San Diego, Calif.). Each operant chamber consisted of a stainless steel grid floor and a metal wheel manipulandum located on one wall, which required a 0.2 N force to rotate it a quarter turn. Gold-contact swivel commutators and bipolar leads connected the animals in the stimulation circuit (Plastics One, Roanoke, Va.). Brain stimulation was administered by constant current stimulators (Stimtek 1200, San Diego Instruments, San Diego, Calif.).

Surgical Procedure

The rats were prepared with 11 mm stainless steel bipolar electrodes (Plastics One; diameter=0.25 mm) in the posterior lateral hypothalamus (AP −0.5 mm from bregma; L±1.7 mm; DV −8.3 mm from dura, with the incisor bar set at 5 mm above the interaural line; Pellegrino et al. 1979 under halothane anaesthesia (1-1.5% halothane/oxygen mixture). Subjects were allowed to recover for at least seven days before any behavioral testing. Half of the electrodes were positioned on the right hemisphere and the other half on the left hemisphere to counterbalance possible brain asymmetries.

Drugs

Paroxetine hydrochloride (generously provided by SmithKline Beecham, Worthing, West Sussex, U.K.) was dissolved in saline with a few drops of polyoxyethylenesorbitan monooleate (tween 80) (Sigma, St. Louis, Mo.) and then brought to a pH of approximately 6.5 using 0.05 M NaOH. Paroxetine was administered intraperitoneally in a volume of 4 ml/kg. 4-(2'-Methoxy-phenyl)-1-[2'-(n-(2"-pyridinyl)-p-iodobenzamido]-ethyl-piperazine hydrochloride (p-MPPI) (Research Biochemicals Inc., Natick, Mass.) was dissolved in sterile water and sonicated for 10-20 min in a heated water bath, and then brought to a pH of approximately 5.2 with 0.1 M NaOH. p-MPPI was administered subcutaneously in a volume of 1 ml/kg. d-Amphetamine sulfate (obtained from the National Institute on Drug Abuse, Bethesda, Md.) was dissolved in saline and administered intraperitoneally in a volume of 1 ml/kg.

Intracranial Self-Stimulation Behavioral Procedure

The ICSS discrete-trial current-threshold procedure is a modified version (for details, see Markou and Koob 1992; Harrison and Markou 2001) of a procedure initially developed by Kornetsky and coworkers (Kornetsky and Esposito, 1979). The subjects were initially trained to turn the wheel manipulandum on a fixed ratio 1 schedule of reinforcement. The electrical reinforcer had a train duration of 500 msec and consisted of 0.1 ms rectangular cathodal pulses delivered at a frequency of 100 Hz. The current intensity delivered was adjusted for each animal and typically ranged from 100 to 200 $\mu A$. After successful familiarization with this procedure (2 sessions of 100 reinforcers in less than 20 minutes), the rats were gradually trained on a discrete-trial, current-threshold procedure.

At the start of each trial rats received a non-contingent electrical stimulus. During the following 7.5 sec, the limited hold, if the subjects responded by turning the wheel manipulandum a quarter turn (positive response) they received a second, contingent stimulus identical to the previous non-contingent stimulus. During a 2 sec period immediately following a positive response, further responses were recorded as extra responses but had no consequence. If no response occurred during the 7.5 sec limited hold period a negative response was recorded. The inter-trial interval (ITI), which followed the limited hold period, had an average duration of 10 sec (ranging from 7.5-12.5 sec). Responses that occurred during the ITI were recorded as time-out responses and resulted in a further 12.5 sec delay of the onset of the next trial. Stimulation intensities were varied according to the classical psychophysical method of limits. The subjects received four alternating series of ascending and descending current intensities starting with a descending series. Within each series the stimulus intensity was altered by 5 $\mu A$ steps between each set of trials (three trials per set). After training in the above procedure, rats were tested until stable baseline thresholds had been achieved L+10% over a 5-day period). Drug testing commenced only after performance had stabilized, which typically occurred after two to three weeks of daily baseline testing. Each test session typically lasted 30 minutes and provided two dependent variables for behavioral assessment:

Thresholds: The current-threshold for each descending series was defined as the stimulus intensity between a successful completion of a set of trials (positive responses during two or more of the three trials) and the stimulus intensity for the first set of trials, of two consecutive sets, during which the animal failed to respond positively on two or more of the three trials. During the ascending series, the reverse situation defined the threshold. Thus, during each session, four current-thresholds were recorded and the mean of these values was taken as the current-threshold for each subject for each test session.

Response Latency: The latency between the onset of the non-contingent stimulus and a positive response was recorded as the response latency. The response latency for each test session was defined as the mean response latency of all trials during which a positive response occurred.

Example 4.1

Effects of Paroxetine on Brain Stimulation Reward

The SSRI paroxetine (0, 1.25, 2.5, 5, 10 mg/kg; n=13) was administered 120 min before the test sessions according to a within-subjects Latin square design with a minimum of seven days between drug injections to ensure return to baseline levels prior to further drug testing.

Example 4.2

Effects of p-MPPI and Combinations of p-MPPI+Paroxetine on Brain Stimulation Reward The effects of p-MPPI alone, and in combination with two doses of paroxetine on brain stimulation reward were assessed using a factorial experimental design. Dose of p-MPPI (0, 1, 3, 10 mg/kg) was the within-subject factor, and dose of paroxetine (0, 1.25 or 5 mg/kg; n=9: 11 and 14 respectively) was the between-subject factor. p-MPPI was administered 135 min prior to test and paroxetine was administered 120 min before test. There was a minimum of seven days between drug injections when paroxetine was administered, and a minimum of three days between drug injections when p-MPPI was administered alone, to ensure a return to baseline threshold levels prior to further drug testing.

Example 4.3

Effects of Paroxetine, p-MPPI and a Combination of p-MPPI+Paroxetine on Reward Deficits During Amphetamine Withdrawal The amphetamine administration regimen used was a modification of that used by Leith and Barrett (1976) and identical to that used by Lin et al. (1999) and Harrison et al. (2001). d-Amphetamine sulfate was administered intraperitoneally three times a day (6:00 A.M., 12:00 P.M., 6:00 P.M.) for four days in a rising dose regimen starting at 1 mg/kg and stabilizing at 5 mg/kg (i.e., 1, 2, 3, 4, 5, 5, 5, 5, 5, 5, 5, 5 mg/kg; total dose=50 mg/kg; n=46; 4 experimental groups, n=11-12/group). Another set of rats (n=43; 4 experimental groups, n=10-12/group) was injected at the same time points with saline. Body weight, intracranial self-stimulation reward thresholds and response latencies were measured each day during this chronic drug administration phase just prior to the first daily injection of either amphetamine or saline (i.e., 5:30 A.M.). Intracranial self-stimulation reward thresholds and response latencies were then determined at 12, 36, 42, 60, 84, 108, 132 and 156 hr after the final amphetamine or saline injection. Based on the animals' performance during the 12 hr test after the final amphetamine or saline injection, subjects were assigned to treatment groups so that original withdrawal effects on threshold elevations were equal across groups. Body weight was measured at 12, 36, 60, 84, 108, 132 and 156 hr after the final amphetamine or saline injection. Acute administration of vehicle, p-MPPI (3 mg/kg), paroxetine (1.25 mg/kg), or p-MPPI (3 mg/kg)+paroxetine (1.25 mg/kg) occurred prior to the 36 hr test session. This time point was selected based on the time course of threshold elevations observed during amphetamine withdrawal previously (Lin et al. 1999; Paterson et al. 2000; Harrison et al. 2001). Doses of paroxetine and p-MPPI were selected based on the results of experiments 1 and 2. p-MPPI was administered 135 min prior to test, and paroxetine was administered 120 min prior to test.

Data Analyses

In Example 4.1 and 4.2 reward thresholds and response latencies were expressed as a percentage of the mean baseline values assessed during the three days prior to each drug treatment. Data from Example 4.1 were analyzed using a one-way repeated measures Analysis of Variance (ANOVA) and a linear trend analysis. Data from Example 4.2 were analyzed using a two-way mixed factors ANOVA, with doses of p-MPPI as the within-subject factor and doses of paroxetine as the between-subject factor. Due to the strong a priori hypothesis that p-MPPI+paroxetine drug combinations would elevate reward thresholds (Harrison and Markou 2001), further analysis of each dose-response curve was conducted using linear trend analysis (Hinkle et al. 1998). In Example 4.3 all reward threshold and response latency data were expressed as a percentage of the mean baseline values during the five days immediately prior to the first amphetamine or saline injection. Body weight data were expressed as a percentage of the weight immediately before the first amphetamine or saline injection. Data collected during chronic drug treatment were analyzed using two-way mixed factors ANOVA. The within-subject factor was days of treatment and the between-subject factor was chronic drug treatment (saline or amphetamine). Data collected during amphetamine (or saline) withdrawal were analyzed using three-way mixed factors ANOVA. The within-subject factor was time after amphetamine or saline treatment, and the two between-subject factors were chronic drug treatment (amphetamine or saline) and acute drug treatment administered during withdrawal. Statistically significant interactions were followed by post-hoc Newman-Keuls tests. The level of significance was set at $p<0.05$. All statistical analyses were conducted using the BMDP statistical software package (BMDP Statistical Software Inc., Calif.).

Results
Baseline Thresholds and Response Latencies
Baseline data from Example 4.1 and Example 4.2 were analyzed using one-way ANOVAs to assess potential drifts of baseline performance. No significant differences in thresholds or response latencies were found in any of the experiments. Example 4.1: range of mean thresholds: 110.62-123.52 µA; range of mean response latencies: 3.17-3.34 sec. Example 4.2: p-MPPI+ vehicle: range of mean thresholds: 110.29-113.73 µA; range of mean response latencies: 3.15-3.26 sec; p-MPPI+paroxetine (1.25 mg/kg): range of mean thresholds: 130.22-132.28 µA; range of mean response latencies: 3.25-3.27 sec; p-MPPI+paroxetine (5 mg/kg): range of mean thresholds: 129.19-134.39 µA; range of mean response latencies: 3.29-3.37 sec. Example 4.3: There were no statistically significant differences between the mean baseline thresholds, response latencies or body weights of subjects assigned to the saline "withdrawal" group (n=43) [mean threshold±SEM: 139.18±5.45 µA; mean response latency±SEM: 3.46±0.06 sec; mean body weight±SEM: 508.83±7.40 g], and subjects assigned to the amphetamine withdrawal group (n=46) [mean threshold±SEM: 133.17±4.97 µA; mean response latency±SEM: 3.41±0.06 sec; mean body weight±SEM: 513.99±7.13 g]. Based on the animals' performance during the 12 hr test after the final amphetamine or saline injection, subjects were assigned to treatment groups so that original withdrawal effects on threshold elevations were equal across groups.

Example 4.1

Effects of Paroxetine on Brain Stimulation Reward

Figure 17:
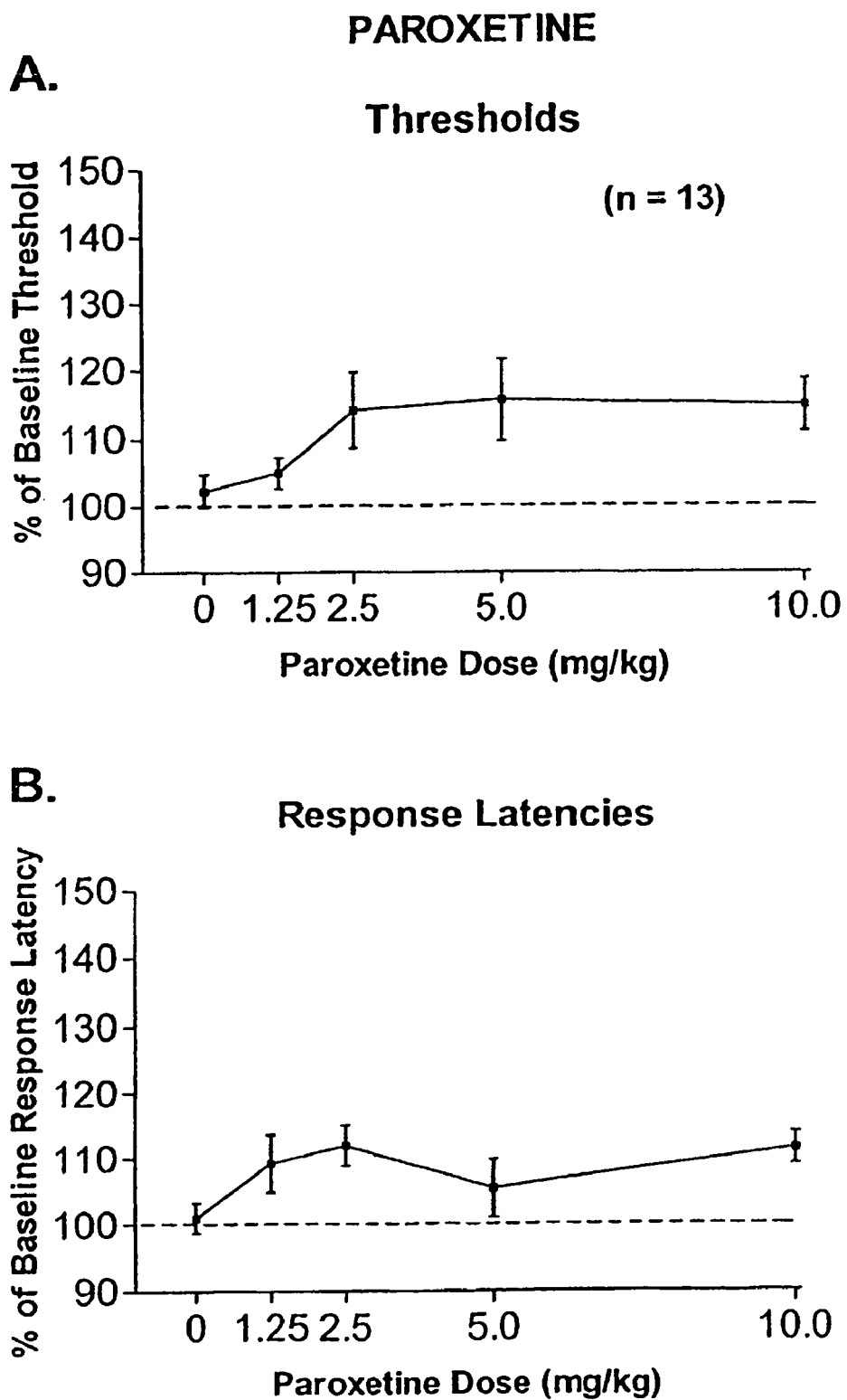
FIGS. 17A-17B illustrate the effects of the selective serotonin reuptake inhibitor paroxetine on brain reward thresholds (A) and response latencies (B) (mean±SEM).

Paroxetine had no statistically significant effect on thresholds [$F(4,48)=1.77$, n.s.] or response latencies [$F(4,48)=2.16$, n.s.] at the doses administered in the present study (FIGS. 17A and 17B). A linear trend analysis was not significant ($p>0.05$).

Example 4.2

Figure 18:
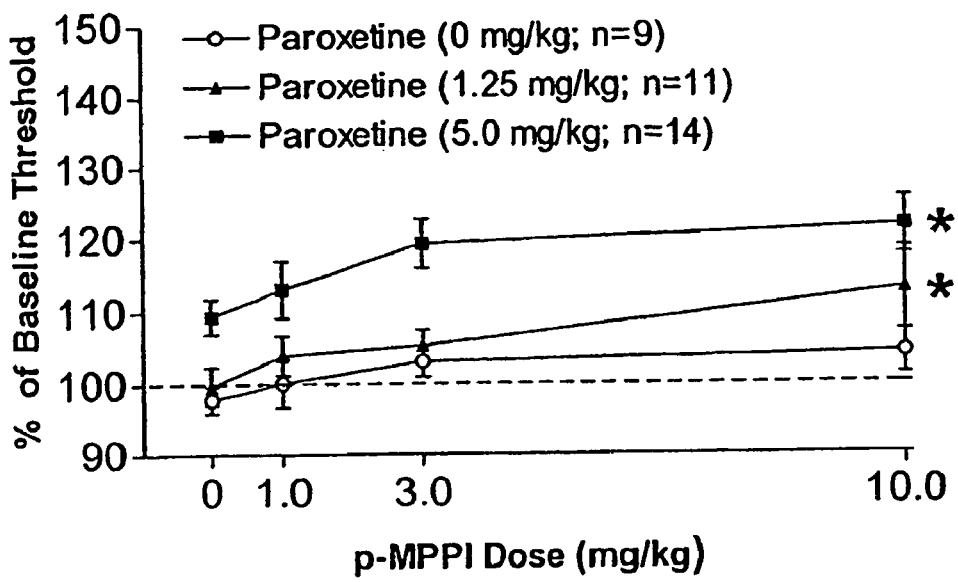
FIGS. 18A-18B illustrate the effects of the serotonin-1A receptor antagonist, p-MPPI, and combinations of p-MPPI+paroxetine on brain stimulation reward thresholds (A) and response latencies (B) (mean±SEM). Asterisks (*) denote a statistically significant linear trend (p<0.05).
Figure 18:
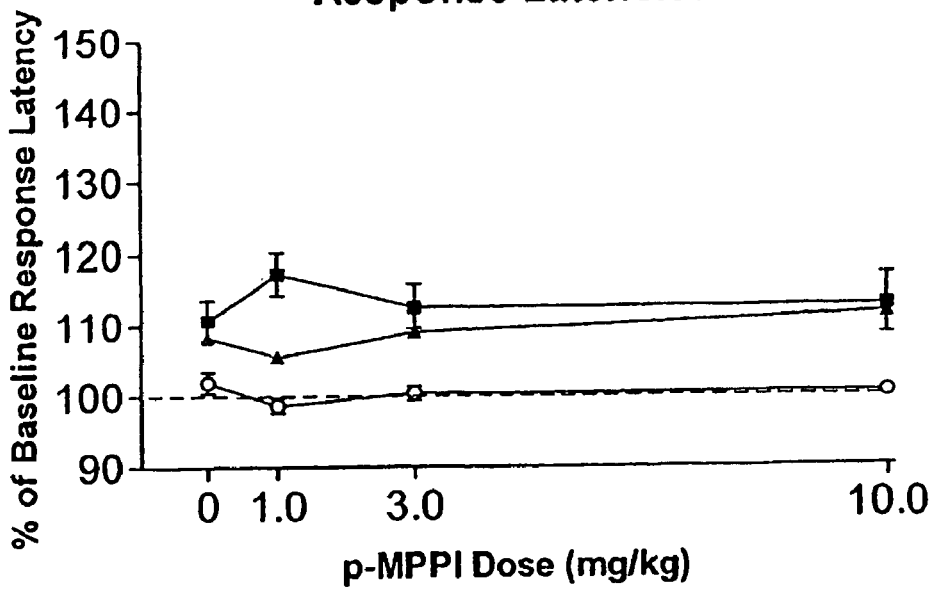

Effects of p-MPPI and Combinations of p-MPPI+Paroxetine on Brain Stimulation Reward Analysis of the threshold data revealed a main effect of paroxetine [$F(2,31)=22.22$, $p<0.01$] and a main effect of p-MPPI [$F(3,93)=5.65$, $p<0.05$] but no significant interaction between the two drugs [$F(6,93)=0.33$, n.s.]. The a priori hypothesis that administration of p-MPPI+paroxetine would elevate thresholds, based on previous findings with p-MPPI+fluoxetine administration (Harrison and Markou 2001), permitted further analysis of these data. Linear trend analysis of each dose-response curve revealed that p-MPPI administered alone had no effect on reward thresholds [$F(1,5)=3.748$, n.s.], whereas p-MPPI administered in combination with paroxetine (1.25 mg/kg or 5 mg/kg) elevated thresholds in a p-MPPI dose-related manner [$F(1,7)=7.75$, $p<0.05$ and $F(1,10)=7.95$, $p<0.05$, respectively for the two doses of paroxetine] (FIG. 18A). Analysis of the response latency data demonstrated that paroxetine increased response latencies [$F(2,31)=9.41$, $p<0.01$], whereas p-MPPI had no effect on response latencies [$F(3,93)=0.17$, n.s.] and did not interact with the effect of paroxetine on response latencies [$F(6,93)=1.28$, n.s] (FIG. 18B).

Example 4.3

Figure 19:
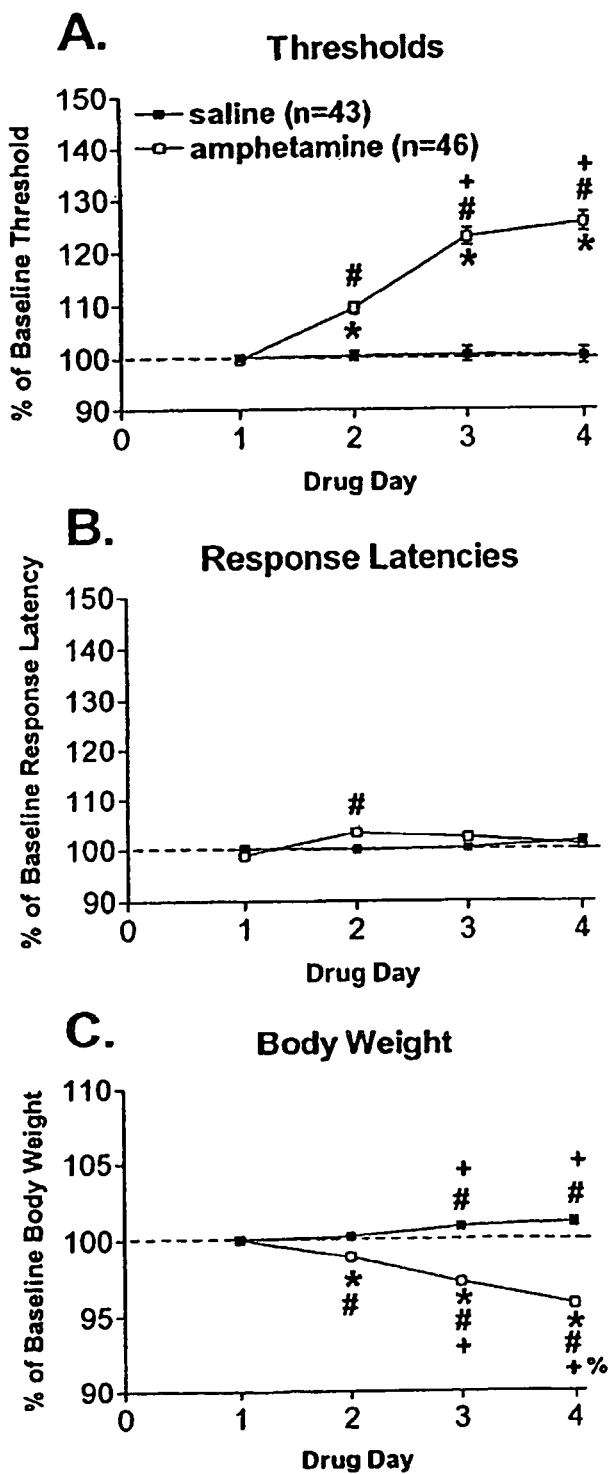
FIGS. 19A-C illustrate the effects of chronic amphetamine administration on reward thresholds (A), response latencies (B) and body weight (C) (mean±SEM). Asterisks (*) denote statistically significant differences from saline-exposed control animals (p<0.05). Hashes (#) denote statistically differences from drug day 1 (before any drug administration; baseline day) within each drug group (p<0.05). Crosses (+) denote statistically significant differences from drug day 2 within each drug group. (%) denotes statistically differences from drug day 3 within each drug group (p<0.05). Filled squares represent data from asaline treated rats. Open circles represent data from amphetamine treated rats.

Effects of Paroxetine, p-MPPI and a Combination of p-MPPI+Paroxetine on Reward Deficits During Amphetamine Withdrawal Chronic Amphetamine: Chronic amphetamine administration (four day treatment) significantly elevated thresholds in compared to thresholds of saline-exposed animals during the tests that were conducted immediately before the first daily injection (12 hr after the previous amphetamine or saline injection) [$F(1,87)=117.95$, $p<0.01$]. Analysis of a significant days of treatment×chronic drug treatment interaction [$F(3,261)=50.81$, $p<0.01$] demonstrated that the thresholds of amphetamine-exposed animals were elevated in a treatment duration-related manner with significant elevations observed between drug days 1 (prior to the first injection; baseline) and 2, and drug days 2 and 3, but not between drug days 3 and 4. The thresholds of the amphetamine-exposed animals were significantly higher than those of the saline-exposed animals on drug days 2, 3 and 4. The thresholds of saline-exposed rats remained stable during this phase of the experiment (FIG. 19A).

Analysis of the response latency data revealed a significant days of treatment×drug treatment interaction [$F(3,261)=2.82$, $p<0.05$]. The response latencies of amphetamine-exposed animals were significantly slower on drug day 2 when compared to drug day 1 (day prior to treatment; baseline), whereas the response latencies of saline-exposed animals remained stable during treatment. Nevertheless, the response latencies of the amphetamine-exposed rats did not significantly differ from those of the saline-exposed rats at any stage during chronic drug treatment (FIG. 19B).

Chronic amphetamine administration significantly reduced the body weight of animals in comparison to weights of saline-exposed controls [$F(1,87)=282.5$, $p<0.01$]. Analysis of a significant days of treatment×drug treatment interaction [$F(3,261)=209.77$, $p<0.01$] demonstrated that the body weight of amphetamine-exposed rats was reduced in a treatment duration-dependent manner with significant reductions of body weight observed on each day of chronic amphetamine treatment compared to the previous day. By contrast the body weight of saline-exposed animals significantly increased between drug days 2 and 3. The body weights of amphetamine-exposed animals were significantly lower than those of the saline-exposed animals on drug days 2, 3 and 4 (FIG. 19C).

Figure 20:
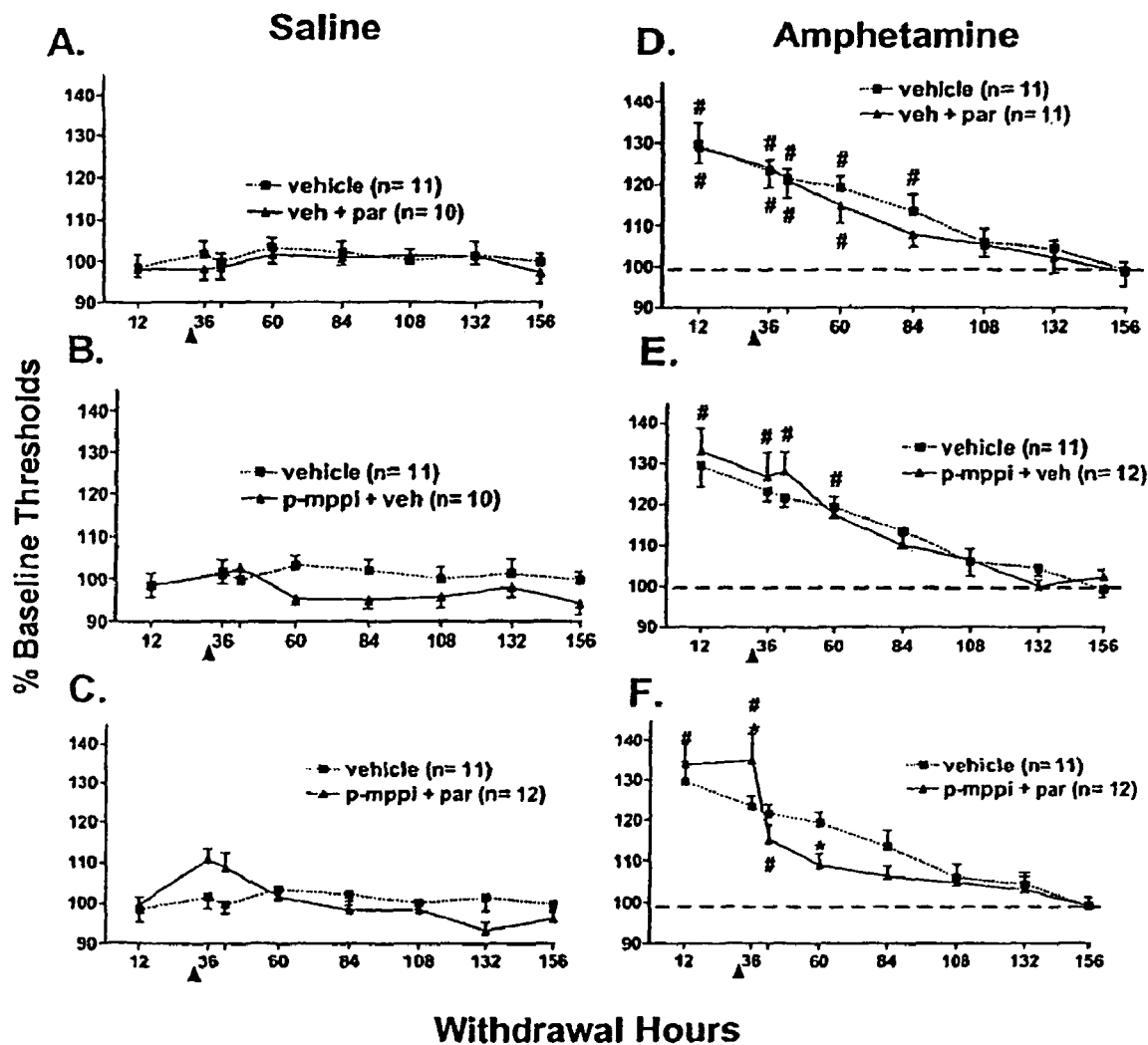
FIGS. 20A-F illustrate the effects of serotonergic treatments on amphetamine withdrawal-induced reward deficits.

Amphetamine withdrawal: Amphetamine-exposed animals exhibited elevated thresholds relative to saline-exposed rats after the final amphetamine injection [$F(1,81)=84.88$, $p<0.01$]. Analysis of the significant time×chronic treatment×acute treatment interaction [$F(21,567)=1.63$, $p<0.05$] revealed the following. Amphetamine-exposed rats treated with vehicle prior to the 36 hr time point exhibited elevated thresholds at withdrawal hours 12, 36, 42, 60 and 84, that returned to baseline levels 108 hr after the final amphetamine injection compared to saline-exposed rats treated with vehicle (FIG. 20A and 20D). Neither paroxetine (FIG. 4A & 4D) nor p-MPPI (FIG. 20B and 20E) had an effect on thresholds of saline-exposed animals. However, both paroxetine (FIG. 20D) and p-MPPI (FIG. 20E) shortened the duration of the reward deficits as indicated by return to baseline reward threshold levels (defined as no statistically significant differences from the saline-exposed vehicle-treated rats) 24 hour before the amphetamine-withdrawing non-drug-treated rats. The co-administration of p-MPPI+paroxetine resulted in significantly elevated thresholds at the 36 hour time-point immediately after the drug administration and significantly lower thresholds at the 60 hour time-point compared to amphetamine-exposed vehicle-treated rats (FIG. 20F). This combination treatment shortened the duration of the reward deficits as indicated by return to baseline reward threshold levels (defined as no statistically significant differences from the saline-exposed vehicle-treated rats) 48 hour before the amphetamine-withdrawing non-drug-treated rats (FIG. 20F). The same combination treatment had no significant effect in saline-exposed rats when compared to saline-exposed vehicle-treated rats (FIG. 20C). However, there was a trend for threshold elevations induced by this treatment at the 36 hour time-point immediately after the drug administration compared to later performance of the same group (i.e., time points 84, 108, 132, and 156 hr; FIG. 20C).

Figure 21:
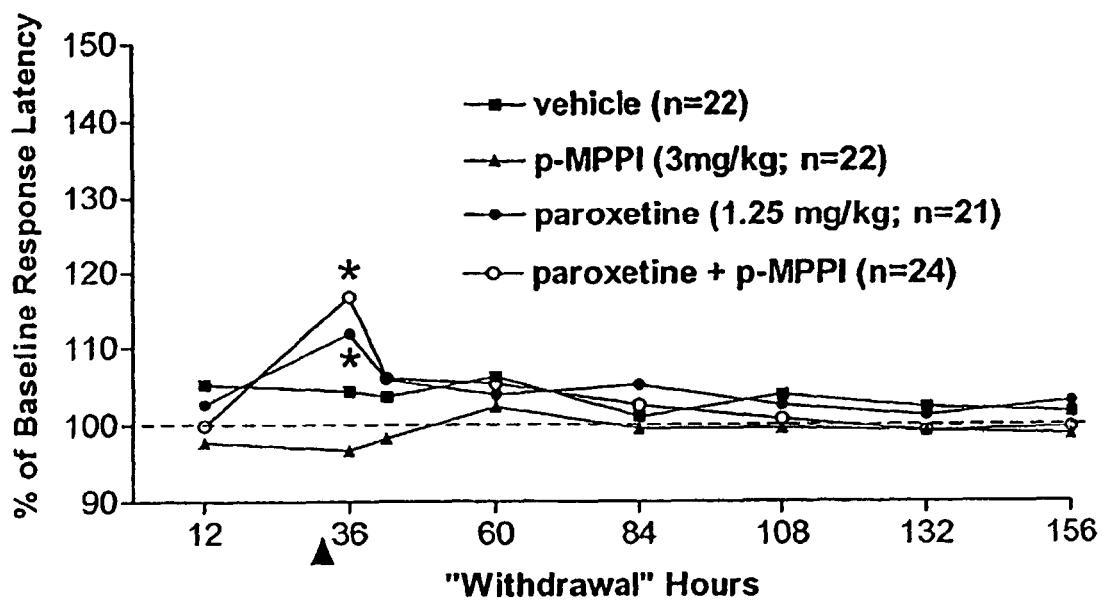
FIG. 21 illustrates the effects of amphetamine withdrawal and serotonergic treatments on response latencies (mean±SEM). The arrow indicates the time-point at which the acute drug treatment was administered. Asterisks (*) denote statistically significant differences from the vehicle control group (p<0.05). Squares represent data points from vehicle-treated rats (n=22). Triangles represent data from p-MPPI treated rats (3 mg/kg; n=22). Filled circles represent data from paroxetine treated rats (1.25 mg/kg; n=21). Open circles represent data from rats treated with paroxetine and p-MPPI (n=24).

Analysis of response latencies during withdrawal revealed a significant time×acute treatment interaction [$F(21,567)=4.00$, $p<0.01$]. Acute vehicle or p-MPPI treatment had no effect on response latencies. However, the response latencies of paroxetine, and p-MPPI+paroxetine-treated animals were significantly slower than those of either vehicle or p-MPPI treated rats 36 hr after the final amphetamine or saline injection (FIG. 21).

Figure 22:
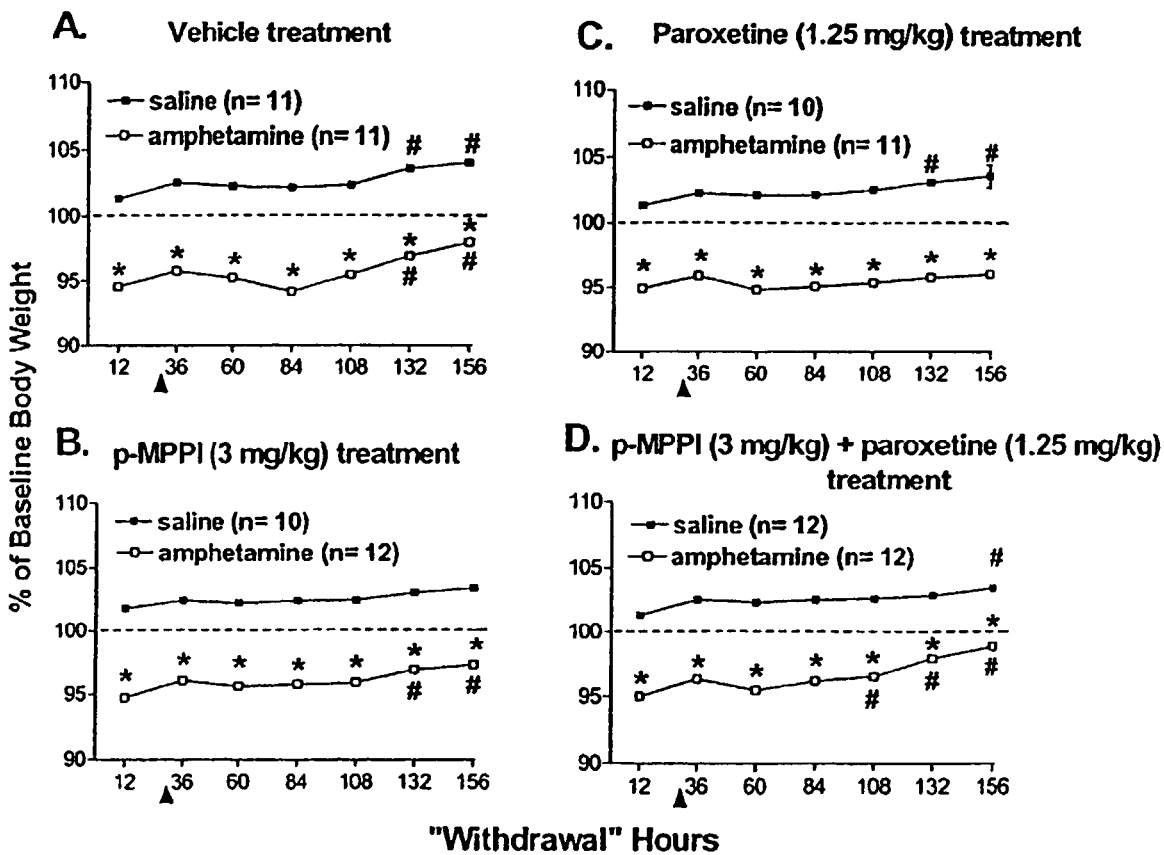
FIGS. 22A-22D illustrate the effects of amphetamine withdrawal and serotonergic treatments on body weight (mean±SEM). The arrow indicates the time-point at which the acute drug treatment was administered. Asterisks (*) denote statistically significant differences between the saline- and amphetamine-exposed groups (p<0.05). Hashes (#) denote statistically significant differences from the 12 hr time point (after chronic treatment and before the acute treatment) within each drug group (p<0.05). Closed squares represent saline-treated groups and open squares represent amphetamine-treated groups. For saline-treated groups, FIG. 22A (Vehicle treatment), n=11.

Amphetamine-exposed animals had lower percentage body weights relative to saline-exposed rats after the final amphetamine injection [$F(1,81)=427.12$, $p<0.01$; FIG. 22]. Analysis of a significant time×chronic treatment×acute treatment interaction [$F(18,486)=1.69$, $p<0.05$] revealed the following. Both saline-exposed and amphetamine-exposed rats treated with vehicle significantly increased in body weight after cessation of chronic drug administration as demonstrated by significant increases of body weight between time points 12 hr and 132 hr after the final injection (FIG. 22A). Amphetamine-exposed rats treated with p-MPPI alone appeared to gain weight similarly to vehicle-treated rats (FIG. 22B). Amphetamine-exposed rats treated with paroxetine alone did not gain weight during withdrawal (FIG. 22C). Most interestingly, amphetamine-exposed rats treated with the drug combination started gaining weight faster than their respective controls (i.e., saline-exposed rats treated acutely with p-MPPI+paroxetine (FIG. 22D).

Discussion

Acute administration of paroxetine, an SSRI, had no significant effect on reward thresholds or response latencies at the doses tested (FIGS. 17A and 17B). However, slight non-significant elevations of reward thresholds can be seen following the administration of doses above 1.25 mg/kg, whereas paroxetine had less consistent effects on response latencies. Administration of SSRIs have produced either small (10%) or no effects on reward thresholds and response latencies (Harrison and Markou 2001; Harrison et al. 2001; Lin et al. 1999; Lee and Kornetsky 1998; Katz and Carroll 1977). This small elevation of reward thresholds induced by SSRI administration may be related to non-specific effects of these drugs on motor performance, or decreased reward resulting from the pharmacological enhancement of serotonergic neurotransmission.

The administration of p-MPPI, a $5\text{-HT}_{1A}$ receptor antagonist, had no effect on brain reward thresholds or response latencies when administered alone. By contrast, the co-administration of p-MPPI+paroxetine (1.25 mg/kg or 5 mg/kg), doses of paroxetine that had no effect on thresholds when administered alone, significantly elevated thresholds in a p-MPPI dose-related manner. These drug combinations had no effect on response latencies indicating a p-MPPI-induced potentiation of the effects of paroxetine on brain stimulation reward rather than alterations in the animals' ability to perform the operant response. These data are consistent with previous reports that $5\text{-HT}_{1A}$ receptor antagonism, by p-MPPI, had no effects on brain stimulation reward when administered alone, yet potentiated the reward-reducing effects of another SSRI, fluoxetine (Harrison et al. 2001; Harrison and Markou 2001). The reward reducing effects of the co-administration of a 5-HT1A receptor antagonist and an SSRI may be due to p-MPPI-induced augmentation of the paroxetine-evoked increase in extracellular serotonin (Bel and Artigas 1993; Blier and de Montigny 1994; Hjorth 1993). On the basis of these results indicating that p-MPPI augments the effects of paroxetine (1.25 mg/kg) on brain stimulation reward, this dose of paroxetine was administered either alone or in combination with p-MPPI (3 mg/kg) in an attempt to alleviate amphetamine withdrawal-induced reward deficits.

During chronic drug treatment, brain stimulation reward thresholds were measured before the first daily injection of either amphetamine or saline (on drug days 2, 3 and 4; this testing occurred 12 hr after the last injection on the previous day). Reward thresholds of amphetamine-exposed animals were significantly elevated on drug days 2, 3 and 4 compared to those of the saline-exposed rats. The reward thresholds of the amphetamine-exposed animals increased in a treatment duration-dependent manner indicating that measurement of reward thresholds, at this time each day, permitted the assessment of the progressive formation of amphetamine withdrawal-induced reward deficits. However, the progressive nature of the formation of these reward deficits was limited. This is indicated by the lack of increases in the magnitude of the reward deficits after 2 days of amphetamine administration (drug day 3) compared to after three days of treatment (drug day 4) (FIG. 19A). This result is consistent with previous reports of limitations of the magnitude of reward threshold elevations after a variety of amphetamine administration regimens (Lin et al. 1999; Paterson et al. 2000). Chronic amphetamine administration had no effect on response latencies compared to those of saline control animals indicating that the elevations of reward thresholds were due to a specific effect on reward and not related to alterations in the animal's ability to perform the operant response.

Chronic amphetamine administration resulted in a treatment duration-dependent reduction of body weight. A progressive reduction of body weight was observed after every day of amphetamine treatment. By contrast, animals chronically treated with saline increased in body weight during this phase of the experiment (see FIG. 18C). These data are consistent with reports of the anorectic effects of amphetamine (Caul et al. 1988). In contrast to the reduction of body weight observed during amphetamine administration, chronic nicotine administration suppressed body weight gain, resulting in no change of body weight during the nicotine administration period, compared to saline-exposed controls that increased in weight over time (Harrison et al. 2001). Although the present study did not address the cause of weight loss, it has been reported that amphetamine administration may reduce body weight by altering food consumption, metabolic rate and fat metabolism (Caul et al. 1988; Jones et al. 1992). Alternatively, the reduction of body weight observed during chronic amphetamine administration in the present study may be the result of a disruption of behavior due to drug-induced stereotypy which has been reported to be augmented by multiple daily amphetamine injections (Segal et al. 1980).

During amphetamine withdrawal animals increased in body weight at a similar rate to saline-exposed control rats (FIG. 22A). These data are consistent with previous reports of similar increases in body weight of amphetamine-withdrawing and saline control rats (Mucha et al. 1990). Acute paroxetine treatment prevented weight gain during the 7 days of amphetamine withdrawal. It has been reported that in rats a single high dose of paroxetine (120-300 mg/kg) administered orally produces a reduction in body weight and food consumption (Ryan et al. 2001). Thus, the failure of the paroxetine-treated animals to gain weight during amphetamine withdrawal may be the result of this anorectic effect of paroxetine treatment. By contrast, the co-administration of paroxetine+p-MPPI resulted in earlier weight gain during amphetamine withdrawal compared to non-withdrawing animals and to vehicle-treated amphetamine-withdrawing animals. These data suggest that the co-administration of a 5-HT1A receptor antagonist with paroxetine facilitated the reversal of amphetamine withdrawal-induced weight loss, whereas the administration of paroxetine alone prevented (during 7 days) or delayed weight gain during amphetamine withdrawal.

In replication of previous findings, amphetamine withdrawal resulted in a reward deficit, reflected in elevated brain reward thresholds relative to saline-exposed rats and to pre-drug baseline thresholds (Leith and Barrett 1976; Kokkinidis and Zacharko 1980; Harrison et al. 2001; Lin et al. 1999; Paterson et al. 2000). Acute p-MPPI or paroxetine administration had no consistent effect on withdrawal-induced reward deficits, but paroxetine significantly increased response latencies of both amphetamine- and saline-exposed rats. Acute administration of p-MPPI+paroxetine reduced the duration of the withdrawal-induced reward deficits by 48 hr indicating a rapid return of sensitivity to the rewarding electrical stimulation in the amphetamine-withdrawing animals. In contrast to the rapid alleviation of amphetamine-withdrawal induced reward deficits, the same combination drug treatment appears to have augmented amphetamine-withdrawal reward deficits during the 36 hr test session (2 hours after administration of the combination drug treatment) as indicated by elevated reward thresholds compared to amphetamine-withdrawing vehicle-treated rats. Similarly, this combination treatment resulted in a small and transient elevation of reward thresholds (i.e. a decrease in reward) in saline-exposed rats during the 36 hr test.

Acute paroxetine and p-MPPI+paroxetine treatment reduced the speed of responding during the test session 2 hr after drug treatment in both amphetamine- and saline-withdrawing rats. In the case of paroxetine-treated animals this decrease in the speed of responding does not appear to have affected reward thresholds of either amphetamine-withdrawing or saline control animals. However, the apparent augmentation of amphetamine withdrawal-induced deficits and elevations of reward thresholds (i.e. reduced reward) of the saline-exposed animals treated with the drug combination may be related to a non-specific effect of this drug treatment on performance of the behavioral task. Although previous findings have indicated that reward thresholds are a valid and reliable measure of reward that are minimally affected by performance manipulations (Markou and Koob, 1992), when elevations in reward thresholds are accompanied by a reduction of the speed of responding (i.e., increased response latency) it is possible that these results are related to disruption of performance rather than alterations of brain reward function.

The present data are strikingly similar to the effects of fluoxetine, another SSRI, in the same experimental procedure (Harrison et al. 2001; Harrison and Markou 2001). In both cases acute administration of the SSRI reduced the duration of amphetamine withdrawal-induced elevations of reward thresholds by 24 hr, an effect that was dramatically augmented by the co-administration of a 5-HT$_{1A}$ receptor antagonist with the SSRI. Further, in contrast to the rapid alleviation of reward deficits observed during amphetamine withdrawal, the combination of either SSRI and a 5-HT$_{1A}$ receptor antagonist reduced the sensitivity of control animals to the rewarding electrical stimulation. One difference between these studies is the doses of the SSRI used to alleviate the reward deficits. When administered alone, 5 mg/kg fluoxetine reduced the duration of the reward deficits, but 2.5 mg/kg fluoxetine did not. The co-administration of p-MPPI with either dose of fluoxetine reversed the reward deficits observed during amphetamine withdrawal. In the present study 1.25 mg/kg paroxetine produced similar results to 5 mg/kg fluoxetine. However, in clinical practice, similar doses of these drugs are prescribed for the treatment of depression suggesting similar antidepressant potency of these two drugs in humans (Tignol 1993; Nemeroff 1993; Dunner and Dunbar 1992; Chouinard et al. 1999; Wagstaff et al. 2002). The present data indicate that paroxetine may be more potent than fluoxetine in reversing the reward deficits associated with amphetamine withdrawal. These data together with previous reports that paroxetine is a more selective and potent serotonin reuptake inhibitor than fluoxetine (Tulloch and Johnson, 1992) suggest that reduced serotonergic transmission plays an important role in the mediation of psychostimulant withdrawal-induced reward deficits. This hypothesis is consistent with in vivo microdialysis data indicating reduced serotonergic transmission during withdrawal from drugs of abuse (Parsons et al. 1995; Weiss et al. 1996). Although these data do not preclude a role of noradrenergic transmission in reward deficits associated with psychostimulant withdrawal, the present data offer strong support to the serotonergic hypothesis.

The rapid restoration of the sensitivity to the electrical stimulation observed following the co-administration of either paroxetine or fluoxetine and a 5-HT$_{1B}$ receptor antagonist may be attributable to increased serotonergic transmission in forebrain structures such as the frontal cortex, hippocampus and the striatum (Bel and Artigas 1993: Dreshfield et al. 1996; 1997; Invernizzi et al. 1994; Gobert and Millan 1999). These data are consistent with the hypothesis that the rapid onset of action of the clinical antidepressant action of SSRIs when combined with pindolol (Bordet et al 1998; Tome et al 1997a; 1997b; Zanardi et al 1998; however, see Berman et al 1999) is partly attributable to pindolol's 5-HT$_{1A}$ receptor antagonist properties. However, other receptors such as 5-HT$_{1B}$ and β-adrenergic receptors may also contribute to pindolol's augmentation of SSRI antidepressant effects (see Introduction).

In contrast to the short lasting elevations of reward thresholds in control rats after the combination drug treatments, which is typical of acute drug treatments, these acute treatments permanently reversed withdrawal-induced reward deficits. This result is perhaps more surprising after acute paroxetine treatment than after fluoxetine treatment. Unlike fluoxetine which has a long half-life due to its active metabolite norfluoxetine, paroxetine has a half-life of approximately 24 hours (Lemberger et al. 1985; Prakash and Foster 1999). Therefore, the effectiveness of these acute treatments in reversing withdrawal-induced reward deficits may be related to the limited duration of the withdrawal-induced reward deficits. Thus, over time the declining enhancement of serotonergic neurotransmission, induced by the acute drug treatments, may coincide with the gradual return of reward thresholds to baseline levels as withdrawal symptoms diminish. Further, the reward deficits in these experiments were transiently induced by drug manipulation (amphetamine withdrawal) in healthy subjects. Thus, acute treatments may be more effective in reversing such reward deficits in healthy subjects in comparison to similar deficits related to a chronic imbalance of the brain reward system.

The elevation of reward thresholds in saline-exposed control rats after the co-administration of an SSRI and a $5\text{-HT}_{1A}$ receptor antagonist appear to be incompatible with the hypothesis that enhancement of serotonergic transmission by antidepressant treatment elevates mood and alleviates reward deficits in depressed individuals (present data; Harrison et al. 2001; Harrison and Markou 2001). This apparent discrepancy is also observed in the present data between the effects of such treatment on brain reward function of amphetamine-withdrawing rats (increased reward) and control rats (decreased reward). These data suggest that the effects of enhanced serotonergic transmission on brain reward function are dependent upon the "hedonic" state of the subjects at the time of treatment (Ahmed and Kood 1998; Koob and LeMoal 1997; Harrison et al. 2001; Harrison and Markou 2001).

In summary, the present data indicated that the co-administration of a $5\text{-HT}_{1A}$ receptor antagonist with paroxetine potentiated the brain stimulation reward-reducing effects of the SSRI in "normal" subjects. In contrast to the reward-reducing effects induced by the co-administration of paroxetine and a $5\text{-HT}_{1A}$ receptor antagonist in "normal" subjects, the same drug combination alleviated brain stimulation reward deficits observed during amphetamine withdrawal (increased reward in anhedonic subjects). These data with paroxetine extend the previous data with fluoxetine by indicating that a second chemically and pharmacokinetically distinct SSRI with higher selectivity for the serotonin tranporter reverses reward deficits associated with amphetamine withdrawal. Thus, these data enhance the predictive validity of amphetamine withdrawal-induced elevations of reward thresholds as a model of depression. Furthermore, these SSRI data (present data; Harrison et al. 2001) support the hypothesis that reduced serotonergic transmission may be one of the neurobiological abnormalities underlying the symptom of "diminished interest or pleasure" seen during amphetamine withdrawal (American Psychiatric Association 1994; Markou et al. 1998; Harrison et al. 2001). Further, considering the substantial evidence suggesting that reduced serotonergic transmission is associated with non-drug-induced depression, the present data may indicate similarities in the neurobiological substrates of both drug- and non-drug-induced depression (Markou et al. 1998; Markou and Kenny 2002; Barr et al. 2002). Specifically, reduced serotonergic transmission may underlie, in part, the affective symptom of "diminished interest or pleasure" in both of these types of depression.

REFERENCES CITED IN EXAMPLE 4

Ahmed S, Koob G F (1998) Transition from moderate to excessive drug intake: Change in hedonic set point. Science 282:298-300

American Psychiatric Association (1994) Diagnostic and statistical manual of mental disorders, $4^{th}$ ed. American Psychiatric Press, Washington D.C.

Artigas F, Romero L, de Montigny C, Blier P (1996) Acceleration of the effect of selected antidepressant drugs in major depression by 5-HT1A antagonists. Trends Neurosci 19:378-383

Assie M B, Koek W (1996) (-)-pindolol and (+)-tertatolol affect rat hippocampal 5-HT levels through mechanisms involving not only $5\text{-HT}_{1A}$ but also $5\text{-HT}_{1B}$ receptors. Neuropharmacology 35:213-222

Auerbach S B, Hjorth S (1995) Effect of chronic administration of the selective serotonin (5-HT) uptake inhibitor citalopram on extracellular 5-HT and apparent autoreceptor sensitivity in rat forebrain in vivo. Naunyn-Schmiedebergs Arch Pharmacol 352:597-606

Barr A M, Markou A, Phillips A G (2002) A "crash" course on psychostimulant withdrawal as a model of depression. Trends Pharmacol Sci 23:475-482

Bel N, Artigas F (1993) Chronic treatment with fluvoxamine increases extracellular serotonin in the frontal cortex but not in raphe nuclei. Synapse 15:243-245

Berman R M, Anand A, Cappiello A, Miller H L, Hu X S, Oren D A, Charney D S (1999) The use of pindolol with fluoxetine in the treatment of major depression: Final results from a double-blind, placebo-controlled trial. Biol Psychiatry 45:1170-1177

Blier P, de Montigny C (1994) Current advances and trends in the treatment of depression. Trends Pharmacol Sci 15:220-226

Blier P, de Montigny C (1999) Serotonin and drug-induced therapeutic responses in major depression, obsessive-compulsive disorder and panic disorders. Neuropsychopharmacology 21(2 Suppl):91S-98S Bordet R, Thomas P, Dupuis B (1998) Effect of pindolol on onset of action of paroxetine in the treatment of major depression: Intermediate analysis of a double-blind, placebo-controlled trial. Am J Psychiatry 155:1346-1351

Bourin M, Chue P, Guillon Y (2001) Paroxetine: a review. CNS Drug Rev 7:25-47

Bourin M, Redrobe J P, Baker G B (1998) Pindolol does not act only on $5\text{-HT}_{1A}$ receptors in augmenting antidepressant activity in the mouse forced swimming test. Psychopharmacology 136:226-234

Caldecott-Hazard S, Morgan D G, DeLeon-Jones M, Overstreet D H, Janowsky D (1991) Clinical and biochemical aspects of depressive disorders: II. Transmitter/receptor theories. Synapse 9:251-301

Caul W F, Jones J R, Barret R J (1988) Amphetamine's effects on food consumption and body weight: The role of adaptive processes. Behav Neurosci 102:441-450

Chouinard G, Saxena B, Belanger M C, Ravindran A, Bakish D, Beauclair L, Morris P, Vasavan Nair N P, Manchanda R, Reesal R, Remick R, O'Neill M C (1999) A Canadian multicenter, double-blind study of paroxetine and fluoxetine in major depressive disorder. J Affect Disord 54:39-48

Clifford E M, Gartside S E, Umbers V, Cowen P J, Hajos M, Sharp T (1998) Electrophysiological and neurochemical evidence that pindolol has agonist properties at the 5-HT$_{1A}$ autoreceptor in vivo. Br J Pharmacol 124:206-212

Cremers T I, Wiersma L J, Bosker F J, den Boer J A, Westerink B H, Wikstrom H V (2000) is the beneficial antidepressant effect of coadministration of pindolol really due to somatodendritic autoreceptor antagonism? Biol Psychiatry 50:13-21

Dreshfield L J, Rocco V P, Wong D T (1997) Greater effects of fluoxetine and its combination with (−)-pindolol in elevating hypothalamic serotonin in rats during dark hours. Chin J Physiol 40: 57-61

Dreshfield U, Wong D T, Perry K W, Engleman E A (1996) Enhancement of fluoxetine-dependent increase of extracellular serotonin (5-HT) levels by (−)-pindolol, an antagonist at 5-HT$_{1A}$ receptors. Neurochem Res 21:557-562

Dunner D L, Dunbar G C (1992) Optimal dose regimen for paroxetine. J Clin Psychiatry 53(Suppl): 21-26

Epping-Jordan M P, Watkins S S, Koob G F, Markou A (1998) Dramatic decreases in brain reward function during nicotine withdrawal. Nature 393:76-79

Gobert A, Millan M J (1999) Modulation of dialysate levels of dopamine, noradrenaline, and serotonin (5-HT) in the frontal cortex of freely-moving rats by (−)-pindolol alone and in association with 5-HT reuptake inhibitors: Comparative roles of β-adrenergic, 5-HT$_{1A}$, and 5-HT$_{1B}$ receptors. Neuropsychopharmacology 21:268-284

Harrison A A, Liem Y T, Markou A (2001) Fluoxetine combined with a serotonin-1A receptor antagonist reversed reward deficits observed during nicotine and amphetamine withdrawal in rats. Neuropsychopharmacology 25:55-71

Harrison A A, Markou A (2001) Serotonergic manipulations both potentiate and reduce brain stimulation reward in rats: Involvement of serotonin-1A receptors. J Pharmacol Exp Ther 297: 316-325

Hinkle D E, Weirsma W, Jurs S G (1998) Applied statistics for the behavioral sciences. Houghton Mifflin Co., Boston, pp 405-410

Hjorth S (1993) Serotonin 5-HT$_{1A}$ autoreceptor blockade potentiates the ability of the 5-HT reuptake inhibitor citalopram to increase nerve terminal output of 5-HT in vivo: A microdialysis study. J Neurochem 60:776-779

Invernizzi R, Bramante M, Samanin R (1994) Chronic treatment with citalopram facilitates the effect of a challenge dose on cortical serotonin output: Role of presynaptic 5-HT$_{1A}$ receptors. Eur J Pharmacol 260:243-246

Jones J R, Caul W F, Hill J O (1992) The effects of amphetamine on body weight and energy expenditure. Physiol Behav 51:607-611

Katz R J, Carroll B J (1977) Intracranial reward after Lilly 110140 (fluoxetine HCL): evidence for an inhibitory role for serotonin. Psychopharmacology 51:189-193

Kokkinidis L, Zacharko R M (1980) Response sensitization and depression following long-term amphetamine treatment in a self-stimulation paradigm. Psychopharmacology 68:73-76

Koob G F, Le Moal M (1997) Drug abuse: Hedonic homeostatic dysregulation. Science 278:52-58

Kornestsky C, Esposito R U (1979) Euphorigenic drugs: Effects on the reward pathways of the brain. Federation Proc 38:2473-2476

Kreiss D S, Lucki I (1995) Effects of acute and repeated administration of antidepressant drugs on extracellular levels of 5-hydroxytryptamine measured in vivo. J Pharmacol Exp Ther 274:866-876

Kung H F, Kung M-P, Clarke W, Maayani S, Zhuang Z-P (1994) A potential 5-HT$_{1A}$ receptor antagonist: p-MPPI. Life Sci 55:1459-1462

Lee K, Kornetsky C (1998) Acute and chronic fluoxetine treatment decreases the sensitivity of rats to rewarding brain stimulation. Pharmacol Biochem Behav 60:539-544

Leith N J, Barrett R J (1976) Amphetamine and the reward system: Evidence for tolerance and post-drug depression. Psychopharmacologia 46:19-25

Lemberger L, Bergstrom R F, Wolen R L, Farid N A, Enas G G, Aronoff G R (1985) Fluoxetine: Clinical pharmacology and physiologic disposition. J Clin Psychiatry 46:14-19

Lin D, Koob G F, Markou A (1999) Differential effects of withdrawal from chronic amphetamine or fluoxetine administration on brain stimulation reward in the rat: Interactions between the two drugs. Psychopharmacology 145: 283-294

Markou A, Kenny P J (2002) Neuroadaptations to chronic exposure to drugs of abuse: relevance to depressive symptomatology seen across psychiatric diagnostic categories. Neurotox Res 4:297-313

Markou A, Koob G F (1991) Postcocaine anhedonia: An animal model of cocaine withdrawal. Neuropsychopharmacology 4:17-26

Markou A, Koob G F (1992) Construct validity of a self-stimulation threshold paradigm: Effects of reward and performance manipulations. Physiol Behav 51:111-119

Markou A, Kosten T R, Koob G F (1998) Neurobiological similarities in depression and drug dependence: A self-medication hypothesis. Neuropsychopharmacology 18:135-174

McAskill R, Mir S, Taylor D (1998) Pindolol augmentation of antidepressant therapy. Br J Psychiatry 173:203-208

Mucha R F, Walker M J K, Fassos F F (1990) Parker and Radow test of drug withdrawal aversion: Opposite effect in rats chronically infused with sufentanil or amphetamine. Pharmacol Biochem Behav 35:219-224

Nemeroff C B (1993) Paroxetine: An overview of the efficacy and safety of a new selective serotonin reuptake inhibitor in the treatment of depression. J Clin Psychopharmacol 13:10S-17S Parsons L H, Koob G F, Weiss F (1995) Serotonin dysfunction in the nucleus accumbens of rats during withdrawal after unlimited access to intravenous cocaine. J Pharmacol Exp Ther 274:1182-1191

Paterson N E, Myers C, Markou A (2000) Effects of repeated withdrawal from continuous amphetamine administration on brain reward function in rats. Psychopharmacology 152:440-446

Pauwels P J, Palmier C (1994) Differential functional activity of 5-hydroxytryptamine receptor ligands and beta adrenergic receptor antagonists at 5-hydroxytryptamine$_{1B}$ receptor sites in Chinese hamster lung fibroplasts and opossum renal epithelial cells. J Pharmacol Exp Ther 270: 938-945

Pellegrino L J, Pellegrino A S, Cushman A J (1979) A stereotaxic atlas of the rat brain, $2^{nd}$ ed. Plenum Press, New York.

Prakash A, Foster R H (1999) Paroxetine: a review of its use in social anxiety disorder. CNS Drugs 12:151-169

Rickels K, Amsterdam J, Clary C, Fox I, Schweizer E, Weise C (1989) A placebo-controlled, double-blind, clinical trial of paroxetine in depressed outpatients. Acta Psychiatr Scand Suppl 350:117-123

Romero L, Bel N, Artigas F, de Montigny C, Blier P (1996) Effect of pindolol on the function of pre- and postsynaptic 5-HT$_{1A}$ receptors: In vivo microdialysis and electrophysiological studies in the rat brain. Neuropsychopharmacology 15:349-360

Ryan P M, Kelly J P, Chambers P L, Leonard B E (2001) The toxicity profile of a single dose of paroxetine: An alternative approach to acute toxicity testing in the rat. Pharmacol Toxicol 88:59

Schulteis G, Markou A, Gold L H, Stinus L, Koob G F (1994) Relative sensitivity to naloxone of multiple indices of opiate withdrawal: A quantitative dose-response analysis. J Pharmacol Exp Ther 271:1391-1398

Schulteis G, Markou A, Cole M, Koob G F (1995) Decreased brain reward produced by ethanol withdrawal. Proc Natl Acad Sci USA 92:5880-5884

Segal D S, Weinberger S B, Cahill J, McCunney S J (1980) Multiple daily amphetamine administration: Behavioral and neurochemical alterations. Science 207:905-907

Spielewoy C, Markou A (2003) Withdrawal from chronic phencyclidine treatment induces long-lasting depression in brain reward function. Neuropsychopharmacology 28:1106-1116

Tignol J (1993) A double-blind, randomized, fluoxetine-controlled, multicenter study of paroxetine in the treatment of depression. J Clin Psychopharmacol 13(6 Suppl. 2): 18S-22S Tome M B, Cloninger C R, Watson J P, Isaac M T (1997a) Serotonergic autoreceptor blockade in the reduction of antidepressant latency: Personality variables and response to paroxetine and pindolol. J Affect Disord 44:101-109

Tome M B, Isaac M T, Harte R, Holland C (1997b) Paroxetine and pindolol: A randomized trial of serotonergic autoreceptor blockade in the reduction of antidepressant latency. Int Clin Psychopharmacol 12:81-89

Tulloch I F, Johnson A M (1992) The pharmacologic profile of paroxetine, a new selective serotonin reuptake inhibitor. J Clin Psychiatry 53(Suppl 2): 7-12

Wagstaff A J, Cheer S M, Matheson A J, Ormrod D, Goa K L (2002) Spotlight on paroxetine in psychiatric disorders in adults. CNS Drugs 16:425-434

Weiss F, Parsons L H, Schulteis G, Hyytia P, Lorang M T, Bloom F E, Koob G F (1996) Ethanol self-administration restores withdrawal-associated deficiencies in accumbal dopamine and 5-hydroxytryptamine release in dependent rats. J Neurosci 16:3474-3485

Wong D T, Bymaster F P, Engleman E A (1995) Prozac (fluoxetine, Lilly 110140), the first selective serotonin uptake inhibitor and an antidepressant drug: Twenty years since its first publication. Life Sci 57:411-441

Zanardi R, Franchini L, Gasperini M, Lucca A, Smeraldi E, Perez J (1998) Faster onset of action of fluvoxamine in combination with pindolol in the treatment of delusional depression: A controlled study. J Clin Psychopharmacol 18:441-446

Example 5

Bupropion Enhances Brain Reward Function and Reverses the Affective and Somatic Aspects of Nicotine Withdrawal in the Rat This example illustrates that the antidepressant bupropion enhances brain reward function and reverses the affective and somatic aspects of nicotine withdrawal.

Rationale: Bupropion is an atypical antidepressant and the only non-nicotine-based therapy approved for smoking cessation. Its use has raised much debate as to how a non-nicotine-based agent can aid in smoking cessation.

Objectives: We assessed the effects of bupropion on brain reward function under baseline conditions and subsequent to withdrawal from chronic nicotine administration in rats.

Methods: A discrete-trial intracranial self-stimulation paradigm procedure was used that provides one with current intensity thresholds, a measure of reward in rats under baseline conditions and subsequent to withdrawal from chronic nicotine (3.16 mg/kg per day for 7 days via osmotic minipump). Somatic signs were recorded based on a checklist of nicotine abstinence signs in animals withdrawn from nicotine. Results: Bupropion (10-60 mg/kg) dose-dependently lowered reward thresholds in non-withdrawing subjects indicating an increase in reward. Interestingly, a sub-effective dose of bupropion (5 mg/kg) blocked completely the threshold lowering effects of acute nicotine (0.25 mg/kg). Animals withdrawn from chronic nicotine exhibited increases in somatic signs of withdrawal and elevated brain reward thresholds, which is indicative of "diminished interest or pleasure" (i.e. anhedonia) in the rewarding stimuli. Bupropion (10-40 mg/kg) reversed both the reward deficit and the somatic signs, with the highest dose (40 mg/kg) inducing a protracted reversal of the threshold elevation.

Conclusions: Bupropion acts on multiple levels to alter brain reward circuits influenced by nicotine, in addition to reducing the expression of somatic signs of withdrawal. First, bupropion, unlike other antidepressants, increases brain reward function under baseline conditions in non-withdrawing subjects. Second, at low doses bupropion blocks the rewarding effects of nicotine. Third, bupropion reverses the negative affective aspects of nicotine withdrawal. Such actions are likely to act in concert to mediate the unique anti-smoking properties of bupropion.

Introduction

Tobacco smoking is a major public health problem worldwide. Estimates of tobacco related deaths account for 20% of all deaths in developed countries (Peto et al. 1992). Accumulating evidence indicates that nicotine is one of the active ingredients in tobacco smoke that leads to and maintains tobacco addiction (Stolerman and Jarvis 1995). Despite the fact that as many as 40% of smokers attempt to quit each year, only about 6% of these succeed in maintaining abstinence (Jorenby et al. 1999). Therefore, there is great impetus to understand the neurobiological mechanisms underlying both nicotine addiction and therapies that are currently used in smoking cessation programs.

Two types of pharmacological therapies have been approved for smoking cessation by the Food and Drug Administration of the United States (Hughes et al. 1999; Glover and Glover 2001). The first are the nicotine replacement therapies that allow the smoker to substitute the nicotine from cigarettes with other safer nicotine formulations such as chewing gum, transdermal patches, or inhalers (Hughes et al. 1999). The second therapy that is non-nicotine based is the atypical antidepressant bupropion (Hurt et al. 1997; Jorenby et al 1999; Hays et al. 2001; Tashkin et al. 2001; Ahluwalia et al. 2002; George et al. 2002). Whilst the rationale behind the use of nicotine replacement therapies is intuitive, it remains unclear why bupropion is effective in this indication. Bupropion's utility was first realized serendipitously by the clinical observations that depressed patients on the drug decreased their tobacco smoking (Balfour 2001). A possible rationale for the effectiveness of bupropion is provided from the multitude of clinical studies showing a strong link between negative affect and the propensity to smoke and difficulty in quitting (Breslau et al. 1992; 1998; Lipkus et al. 1994; Laje et al. 2001). Indeed, among smokers, symptoms of nicotine dependence are correlated with the magnitude of affective depressive symptomatology (Anda et al. 1990; Glassman et al. 1990). However, a recent study demonstrated that bupropion was equally effective for smoking cessation independent of a past history of major depression, suggesting that this therapeutic effect is independent of, or not exclusive to, its antidepressant properties (Hayford et al. 1999). Furthermore, the initial trials assessing bupropion's effectiveness in smoking cessation excluded depressed patients (e.g. Jorenby et al. 1999). Moreover, other antidepressants, including the selective serotonin reuptake inhibitors, with the possible exception of the tricyclic nortryptiline, have been shown to be rather ineffective in reducing quit rates in non-depressed smokers (see Kotlyar et al. 2001). Therefore, there may be unique neurochemical and behavioral sequelae of bupropion administration, beyond that of its antidepressant properties that engender its antismoking efficacy.

Reward deficits associated with withdrawal from drugs of abuse can be used as an animal model to measure symptoms of "diminished interest or pleasure" that characterizes both drug-withdrawal-induced and nondrug-induced depressions with construct, convergent, and predictive validity (Geyer and Markou 1995; Barr et al. 2002; Cryan et al. 2002; 2003). The use of intracranial self-stimulation (ICSS) has provided investigators with a reliable behavioral readout to assess such alterations in brain reward after cessation of drug administration (i.e. drug withdrawal) (Leith and Barrett 1976; Markou and Koob 1991; Epping Jordan et al. 1998; Cryan et al. 2002; Spielewoy and Markou 2002). Using this paradigm, we have previously shown that withdrawal from chronic nicotine induces a dramatic decrease in brain reward function as reflected by elevations in brain reward thresholds (Epping-Jordan et al. 1998; Harrison et al. 2001a; Semenova and Markou 2003). This threshold elevation is one of the few operational measures of the affective aspects of the nicotine withdrawal syndrome (Kenny and Markou 2001). In addition to the affective symptoms, nicotine withdrawal in humans is also characterized by somatic symptoms such as bradycardia, insomnia, gastrointestinal discomfort, and increased appetite (Hughes et al. 1991). These symptoms are amenable to visual assessment in withdrawing animals (Malin et al. 1992; Malin 2001). A clear dissociation has been demonstrated recently between the neuroanatomical sites of elevations in brain stimulation reward thresholds that are mediated through central mechanisms, and those somatic withdrawal signs that appear to be both centrally and peripherally mediated (Hildebrand et al. 1999; Watkins et al. 2000). It has been postulated that affective signs are of great motivational significance in contributing to relapse and continued nicotine use (Markou et al. 1998). Further, somatic signs of nicotine withdrawal also may contribute to smoking behavior. Thus, animal models of the affective and somatic aspects of nicotine withdrawal are important tools for understanding the neurobiological bases of nicotine dependence and for developing effective treatment strategies to facilitate nicotine abstinence (Kenny and Markou 2001; Malin 2001). The present studies investigated the effects of bupropion on brain reward function under baseline conditions and subsequent to withdrawal from chronic nicotine. In addition, the effects of bupropion on the somatic signs of withdrawal were assessed.

Materials and Methods

Animals

Male Wistar rats (Charles River, Raleigh-Durham, N.C., USA), 275-350 g upon arrival were housed in pairs with food and water available ad libitum, except during testing, in a temperature and humidity controlled vivarium (21° C.). Rats were maintained on a 12-h reverse light/dark cycle with lights on at 1800 hours. All experimental procedures occurred during the dark cycle, and in accordance with the Institutional Animal Care and Use Committee of The Scripps Research Institute. Animals were allowed to habituate to their new environment for at least one week before the start of any procedure, during which time they were handled at least twice.

ICSS apparatus

All training and testing occurred in 16 Plexiglas test chambers (25×31×24 cm; Med Associates, Georgia, Vt., USA) separately housed in larger sound-attenuating boxes (San Diego Instruments, San Diego, Calif., USA). Centered on a side wall of each operant chamber was a metal wheel manipulandum (5 cm wide) requiring approximately 0.2 N force to rotate it a quarter turn. Brain stimulation was delivered using constant current stimulators (Stimtech model 1200; San Diego Instruments). Subjects were connected to the stimulation circuit via bipolar leads (Plastics One, Roanoke, Va., USA) attached to gold-contact swivel commutators (model SL2C; Plastics One) that were mounted above the chamber. Stimulation parameters, data collection and all test session functions were controlled by a microcomputer.

Surgery

ICSS Electrode Implantation

When the subjects reached a minimal weight of 325 g, stainless steel bipolar electrodes, with a diameter of 0.25 mm (model MS303/2; Plastics One) cut to 11 mm in length, were implanted into the medial forebrain bundle at the level of the posterior lateral 348 hypothalamus. Brief electrical stimulation of this region is reinforcing as indicated by the fact that rats perform an operant (turn a wheel) to receive the electrical stimuli (Markou and Koob 1992). A discrete-trial ICSS procedure was used that provides one with current-intensities thresholds, a measure of reward (Markou and Koob 1992). Many drugs of abuse increase brain reward function, as indicated by a decrease in ICSS threshold, whereas withdrawal from drugs of abuse decreases brain reward as indicated by elevations in thresholds.

Subjects were anesthetized with an isoflurane/oxygen vapor mixture (1-3% isoflurane) and secured in a stereotaxic frame (David Kopf Instruments, Tujunga, Calif., USA) with the incisor bar elevated 5.0 mm above the interaural line. Electrodes were implanted according to the following coordinates: AP −0.5 mm from bregma; ML±1.7 mm; and DV −8.3 mm from dura. Half of the subjects received electrodes on the right side of the brain, and half on the left to counterbalance for possible brain asymmetries. Dental acrylic (Teets methyl methacrylate denture material; CoOral-Lite Mfg. Co., Diamond Springs, Calif., USA) anchored the electrode to four stainless steel screws embedded in the skull. The surgical wound was flushed with a solution of 13.3 mg/ml gentamicin sulfate dissolved in physiological saline, closed with silk sutures, and covered with a povidone-iodine antiseptic ointment. After surgery, animals were allowed to recover at least 7 days before the start of behavioral training.

Osmotic Pump Implantation and Removal

Subjects were anesthetized with an isoflurane/oxygen vapor mixture (1-3% isoflurane) and prepared with subcutaneous osmotic minipumps [Alzet model 2ML1 (7 days); Alza Corporation, Palo Alto, Calif., USA] along the back, parallel to the spine, with the flow meter directed posteriorly. Pumps were filled with either physiological saline or nicotine solution. The concentration of the latter was adjusted according to animal weight and pumping rate to deliver a dose of 3.16 mg/kg per day (9 mg/kg per day nicotine hydrogen tartrate). The wound was closed with stainless steel wound clips and covered with a povidone-iodine antiseptic ointment. Pumps were surgically removed seven days later under isoflurane anesthesia, the wounds re-clipped and treated with the antiseptic ointment.

Brain Stimulation Reward Threshold Procedure (ICSS)

Subjects were initially trained to turn the wheel manipulandum on a fixed ratio 1 (FR1) schedule of reinforcement. For each quarter turn, subjects received a 500 ms train of 0.1 ms cathodal square wave pulses at a frequency of 100 Hz. After successful acquisition of the response, defined as 200 consecutive reinforcements within allotted time period (usually <20 min) subjects were trained on a modification of the Kornetsky and Esposito discrete-trial currentthreshold procedure (Kornetsky and Esposito 1979), as described previously by Markou and Koob (1992).

Trials began with an electrical stimulus followed by a 7.5-s response window within which the animal could make a response to receive a second contingent stimulus identical to the initial noncontingent stimulus. A response during this 7.5-s window was considered a positive response, whereas the lack of a response was considered a negative response. Additional responses during a 2-s period immediately following a positive response had no consequence. The intertrial interval (ITI) that followed either a positive response or the end of the response window (in the case of a negative response) ranged from 7.5 to 12.5 s with an average duration of 10 s. Responses that occurred during the ITI resulted in a further 12.5 s delay before the onset of the subsequent trial. During training on the discrete-trial procedure, the duration of the ITI and time-out response delays were gradually increased until the animals performed consistently at a fixed stimulation intensity. Subjects then were tested on a current-threshold procedure in which stimulus intensities were varied during four alternating descending and ascending series with a step size of 5 mA. Blocks of three trials were offered at each current step with the starting current of the first descending series set at 30-40 mA above the subjects' individual baseline thresholds estimated at the end of preliminary training. A descending series was terminated after two consecutive blocks of trials during which the animal failed to make a positive response on at least two out of the three trials or after 15 successive decrements were presented. An ascending series was terminated after two consecutive blocks of trials during which the animal made positive responses on at least two out of the three trials or after 15 successive increments were presented. The mean of the four current thresholds from the alternating series was defined as the subject's ICSS threshold for that session. A series was terminated after either 15 stimulus increments (or decrements) had occurred, or after the determination of the threshold for the series (see below). Each test session typically lasted 30 min.

Thresholds

The current threshold for each descending series was defined as the stimulus intensity between the successful completion of a set of trials (positive responses during two or more of the three trials) and the stimulus intensity for the first set of trials, of two consecutive sets, during which the animal failed to respond positively on two or more of the three trials. During the ascending series, the threshold was defined as the stimulus intensity between the unsuccessful completion of a set of trials (negative responses during two or more of the three trials) and the stimulus intensity for the first set of trials, of two consecutive sets, during which the animal responded positively on two or more of the trials. Thus, during each test session, four thresholds were determined and the mean of these values was taken as the threshold for each subject. After training in the above-mentioned brain stimulation reward procedure, rats were tested until stable baseline thresholds had been achieved (±10% over a 5-day period). Drug testing was initiated only after performance had stabilized, which typically occurred after 2-3 weeks of baseline testing. Return to baseline threshold levels was required between drug injections.

Ratings of Somatic Signs of the Withdrawal Syndrome

Rats were placed individually in transparent plastic cylindrical containers (30×38 cm) in which they could move freely. Subjects were habituated to the containers for 10 min each day over 3 days before the first test session. During the test sessions the rats were observed blindly by an experienced observer for 10 min and the frequency of the following signs was recorded based on a checklist of nicotine abstinence signs (Hildebrand et al. 1999; Watkins et al. 2000; Malin 2001): body shakes, chews, cheek tremors, escape attempts, eye blinks, foot licks, gasps, genital licks, head shakes, ptosis, scratches, teeth chattering, writhes and yawns. Multiple successive counts of any sign required a distinct pause between episodes. Ptosis, if present continuously, was only counted once per minute. For statistical analyses, the total number of somatic signs was defined as the sum of individual occurrences of the above mentioned withdrawal signs. Further, the categories of "abdominal constrictions" included gasps and writhes; "facial fasciculation" included cheek tremors, chews, and teeth chattering; and "miscellaneous other signs" included shakes, escape attempts, licks, scratches, and yawns.

Drugs (−)-Nicotine hydrogen tartrate salt (Sigma, St Louis, Mo., USA) was dissolved in sterile physiological saline (0.9% sodium chloride). Bupropion hydrochloride generously provided by Glaxo-SmithKline, Research Triangle Park, N.C., USA) was dissolved in sterile distilled water. Nicotine doses are expressed as the free base, while bupropion doses are expressed as the salt. All injections were administered in a volume of 1 mvkg.

Experiment 1: Effects of Acute Bupropion Treatment on ICSS Reward Thresholds under Baseline Conditions Bupropion (0, 10, 20, 30 mg/kg, IP, n=8) was administered (30 min pretreatment) according to a within-subjects Latin square design, with a minimum of 3 days between consecutive drug treatments. After return to baseline values, all animals were given an injection of bupropion (40 mg/kg, IP), followed by another injection of 60 mg/kg bupropion IP at least 3 days later. These two highest bupropion doses were administered last to avoid any potential longlasting effects of high bupropion doses. Nevertheless, no such effects were observed. Although the doses used in these studies are higher than the recommended daily dose in humans (300 mg/day) [see GlaxoSmithKline product information on Zyban (bupropion hydrochloride) sustained release tablets 2002, available from on the internet at us.gsk.com/products/assets/us_zyban-.pdf, such comparisons are at best rough because of differences in pharmacokinetics and metabolism of drugs in different species. It should be noted that the doses of bupropion used are in the range that produce robust antidepressant-like behavioural effects in rodents (e.g. Cryan et al. 2001) and that increase hypothalamic concentrations of extracellular dopamine and norepinephrine (Li et al. 2002).

Experiment 2: Effects of Acute Bupropion on Acute Nicotine-Induced Lowering of ICSS Thresholds In a separate naive group of animals bupropion (0, 5, 10, 20 mg/kg, IP, n=10) was administered (30 min pretreatment) in combination with nicotine (0, 0.25 mg/kg, SC; 15 min pretreatment) according to a within-subjects Latin square design, with a minimum of 3 days between consecutive drug treatments. The dose of nicotine was selected from previous dose-response studies from our laboratory showing maximal rewarding effects of acute nicotine at this dose (Harrision et al. 2002), and the dose of bupropion was selected based on the results from experiment 1 described above.

Experiment 3: Effects of Acute Bupropion Treatment on ICSS Reward Thresholds Subsequent to Withdrawal from Chronic Nicotine or Saline Administration Naive animals were prepared with osmotic minipumps containing either an individualized nicotine solution (3.16 mg/kg per day, free base) or saline. The dose of nicotine was selected based on extensive previous dose-response studies which showed that exposure to this dose for 7 days results in a robust and reproducible withdrawal syndrome as assessed by both ICSS (elevations in brain reward thresholds) and somatic signs of withdrawal (Epping-Jordan et al. 1998; Harrison et al. 2001a; Malin 2001). This dose maintains stable plasma nicotine levels (44 ng/ml) comparable to those reported for smokers consuming 30 cigarettes daily (4042 ng/ml) (see Epping-Jordan et al. 1998). After implantation of the minipumps, thresholds were assessed daily thereafter to assess the effects of chronic nicotine exposure on reward thresholds. Seven days (exactly seven 24-h periods) after pump insertion, the pumps were removed in order to precipitate the nicotine withdrawal syndrome. ICSS thresholds were measured 12, 18, 24, 36, 48 and 72 h after pump removal. Animals were injected with bupropion (0, 10, 20, 40 mg/kg IP; n=8-11) 30 min prior to the 18-h time point. This time point was selected because it is the time point when maximal withdrawal-induced deficits (elevations in brain reward thresholds) were observed in previous experiments (Epping-Jordan et al. 1998; Harrison et al. 2001a; Semenova and Markou 2003).

Experiment 4: Effects of Acute Bupropion Treatment on Somatic Signs Subsequent to Withdrawal from Chronic Nicotine Administration Separate drug-naive rats were prepared with osmotic minipumps containing nicotine (3.16 mg/kg per day for 7 days) dissolved in saline. As stated above, this dose of nicotine was selected based on extensive dose-response studies and is one which results in a robust withdrawal syndrome in the rat (Malin et al. 1992; Epping-Jordan et al. 1998; Harrison et al. 2001a; Malin 2001; Skjei and Markou 2003). Further, this nicotine dose was selected to allow direct comparison of the effects of bupropion on somatic signs (present experiment 4) and on reward threshold elevations (experiment 3 described above) observed during nicotine withdrawal. To induce the somatic signs of nicotine withdrawal the minipumps were removed 6 days and 18 h after implantation. The behavioral observations were conducted 6, 12 and 24 h after the removal of the minipumps. The rats were injected with bupropion (0, 5, 10, 20, 40 mg/kg, IP; n=6-8), 30 min prior to the 12-h time point. The selection of the time points was based on the time-course of the expression of the somatic signs after the termination of nicotine exposure (Epping-Jordan et al. 1998; Harrison et al. 2001a; Semenova and Markou 2003; Skjei and Markou 2003).

Data Analyses and Statistics

Threshold data were expressed as a percentage of the previous three to 5-day baseline values before each drug manipulation or the implantation of the minipump. Percent values are used for the statistical analyses of threshold data because raw current intensity threshold values of individual rats vary during baseline conditions due to minor variations in electrode placement and other poorly understood individual subject factors. Extensive previous work in our laboratory has indicated that the use of within-subject designs as the ones described in this manuscript and the expression of threshold data as a percentage of stable baseline thresholds before the implementation of any manipulation is a reliable and validated method for assessing changes in brain reward function (see Markou and Koob 1992). All data were analyzed using the appropriate within-subject, and mixed-design ANOVAs. Statistically significant effects were followed where appropriate with Fisher's individual comparison tests. The level of significance was set at $P<0.05$.

Results

Figure 23:
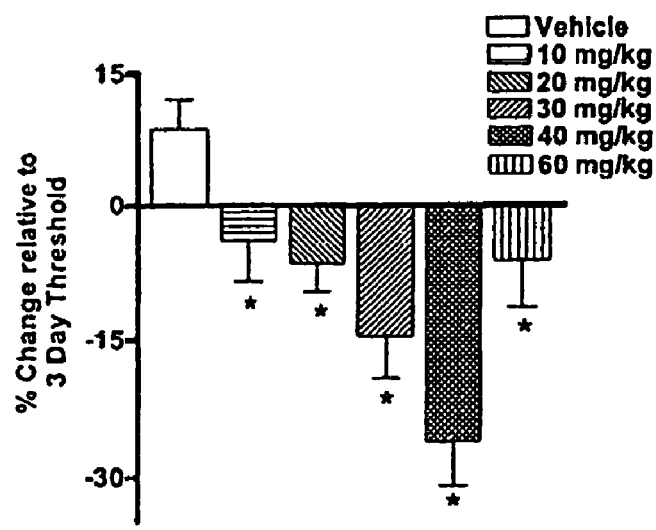
FIG. 23 illustrates the effects of acute treatment with the antidepressant bupropion on brain reward thresholds. Bupropion at all doses (n=8) tested and in a dose-dependent fashion up to 40 mg/kg resulted in a reduction in brain reward thresholds when compared with vehicle-treated animals, which is indicative of an enhancement of brain reward function. All bars represent mean values with vertical lines indicating 1 SEM. * indicates groups that differed significantly from vehicle-treated animals; P<0.05. Open bar is Vehicle; horizontal line bar is 10 mg/kg, upper left to lower right lined bar is 20 mg/kg; lower left to upper right lined bar is 30 mg/kg; cross-hatched bar is 40 mg/kg; and vertical line bar is 60 mg/kg.

Experiment 1: Effects of Acute Bupropion Treatment on ICSS Current Thresholds under Baseline Conditions Acute bupropion treatment induced a pronounced lowering of brain reward thresholds [$F(5, 35)=7.445$, $P<0.001$] which is indicative of an increase in brain reward function (FIG. 23). Post-hoc analyses indicated that bupropion at all doses tested and in a dose-dependent fashion up to 40 mg/kg (40 mg/kg was significantly different from 10 mg/kg bupropion-treated animals) lowered brain reward thresholds compared to the vehicle conditions. Raw mean 3-day baseline thresholds were in the range of 128.19-143.63 mA.

Figure 24:
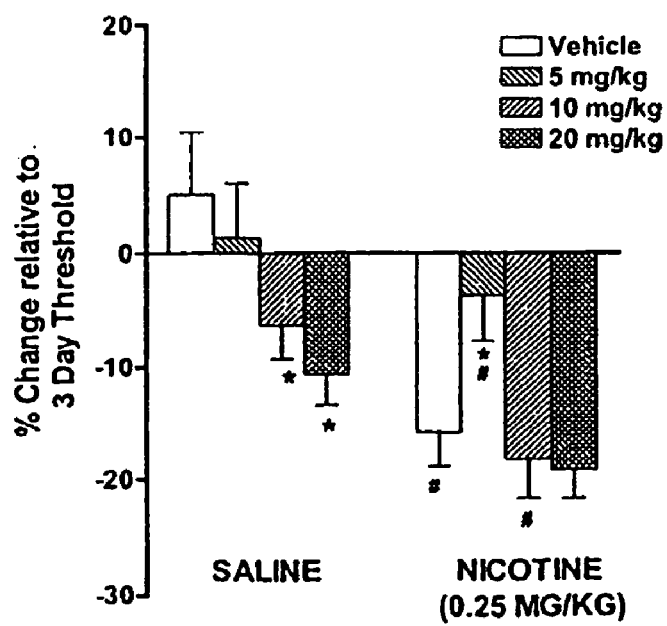
FIG. 24 illustrates the effects of the antidepressant bupropion on nicotine (0.25 mg/kg)-induced enhancement of brain reward function. Bupropion administration (10 and 20 mg/kg) resulted in a lowering of brain reward thresholds (n=10). Nicotine treatment resulted in a similar reduction in reward thresholds. This rewarding effect of nicotine was completely countered by bupropion (5 mg/kg) pretreatment, which was without effect on reward thresholds when given alone. All bars represent mean values with vertical lines indicating 1 SEM. * indicates thresholds that differed significantly from the relevant vehicle condition; P<0.05. # indicates groups that differed significantly from relevant saline co-treated control; P<0.05. Left group of bars are from saline-treated rats. Right group of bars are from nicotine (0.25 mg/kg) treated rats. Open bar is Vehicle; upper left to lower right lined bar is 5 mg/kg; lower left to upper right lined bar is 10 mg/kg; cross-hatched bar is 20 mg/kg.

Experiment 2: Effects of Acute Bupropion on Acute Nicotine-Induced Lowering of ICSS Thresholds As in experiment 1, bupropion (10 and 20 mg/kg, but not 5 mg/kg) lowered brain reward thresholds in animals that were co-treated with saline [$F(3,54)=7.822$, $P<0.001$] (FIG. 24). Similarly, nicotine treatment resulted in lowering of brain reward thresholds [$F(1,18)=11.550$, $P<0.003$], which is consistent with previous findings (Harrison et al. 2002; Skjei and Markou 2003). ANOVA revealed a strong trend towards a significant interaction between the factors nicotine and bupropion [$F(3, 54)=2.405$, $P=0.077$]. Planned comparisons indicated that bupropion at a dose that was ineffective on its own (5 mg/kg) completely reversed the reward-enhancing effects of acute nicotine. However, higher bupropion doses (10 and 20 mg/kg) in combination with nicotine resulted in threshold lowerings that were not significantly different from threshold lowerings induced by nicotine administration alone. Raw mean 3-day baseline thresholds were in the range of 111-133.26 mA.

Figure 25:
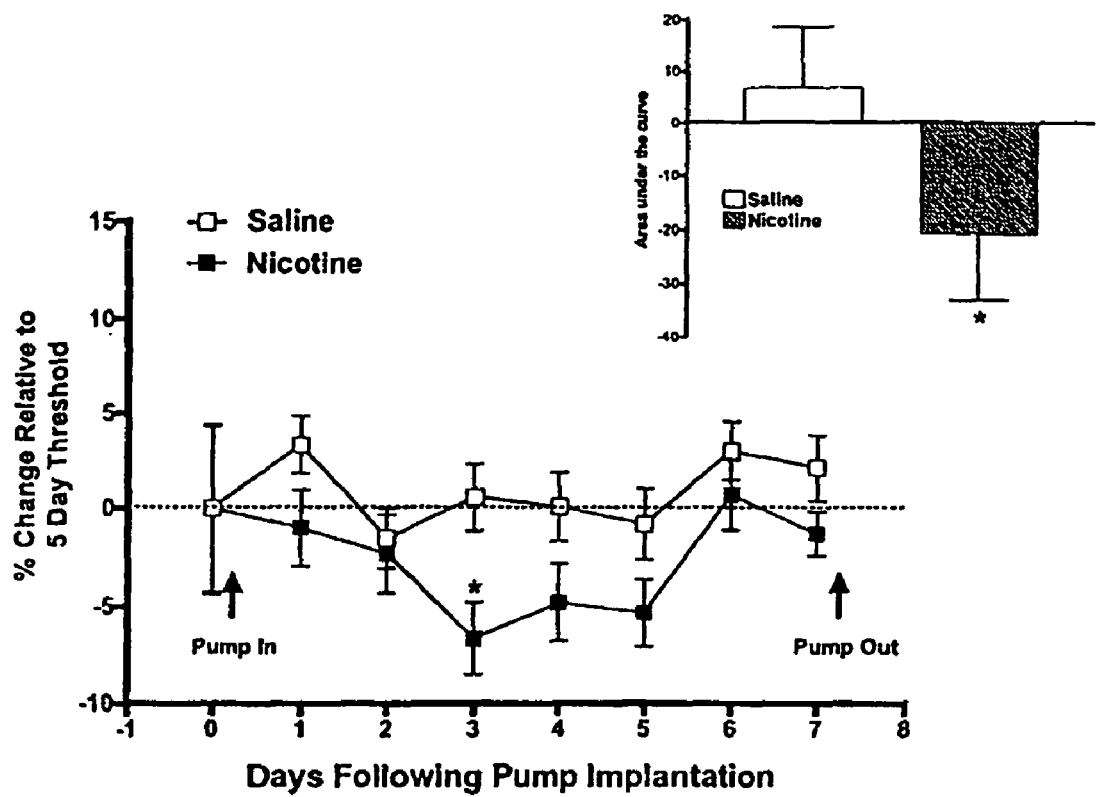
FIG. 25 illustrates the effects of continuous infusion of nicotine (3.16 mg/kg free base per day for 7 days) on brain reward thresholds. Nicotine administration (n=38) resulted in a time-dependent lowering of brain reward thresholds compared to animals prepared with saline pumps (n=38). The peak threshold lowering effect was on day 3. Thresholds returned to baseline levels by day 7. All data points represent mean values with vertical lines indicating 1 SEM. Inset: The area under the curve analysis clearly shows that animals treated with nicotine had significantly lower thresholds over the duration of the 7 days of treatment. All bars represent mean values with vertical lines indicating 1 SEM. * indicates thresholds that differed significantly from the saline-treated animals; $P<0.05$. Open bar and squares represent saline-treated rats. Filled bar and squares represent nicotine-treated rats.

Experiment 3: Effects of Acute Bupropion Treatment on ICSS Current Thresholds During and Subsequent to Withdrawal from Chronic Nicotine or Saline Administration Administration of nicotine via minipumps resulted in a small yet significant reduction in brain reward threshold [$F(1, 74)=5.75$, $P<0.05$], with the maximal effect seen on day 3 of administration. However, the threshold values returned to baseline levels ($P>0.8$) and were not different from those of saline-treated animals at the time of pump removal on day 7 ($P>0.1$). This pattern of results suggests that there was tolerance development to the mild threshold-lowering effects of nicotine (see FIG. 25). Raw mean 5-day baseline values before the implantation of the pumps were 119.75 mA for saline-treated animals and 120.08 mA for animals prepared with nicotine-containing minipumps.

To assess the effects of nicotine withdrawal on brain reward thresholds, thresholds after the removal of the minipumps were expressed as percent of the 5-day baseline threshold values assessed under baseline conditions before the implantation of the minipump. Thus, these percent changes reported for the withdrawal period reflect changes from baseline brain reward thresholds and not changes from thresholds during nicotine exposure when thresholds could have been altered under the influence of nicotine. Nevertheless, as described above, thresholds of nicotine-treated rats were back to baseline threshold levels by day 7 of exposure to nicotine. As anticipated, withdrawal from chronic nicotine administration significantly elevated brain reward thresholds [$F(1,68)=22.219$, $P<0.001$] compared to thresholds of saline-pretreated animals. In addition, the ANOVA revealed that there was a significant change in thresholds over time [F(5, 340)=23.047, P<0.001]. Further, there were significant interactions between the factors pretreatment (nicotine or vehicle) and time [F(5, 340)=5.731, P<0.001], and the factors treatment (bupropion or vehicle) and time [F(15,340)=13.568, P<0.001].

Figure 26:
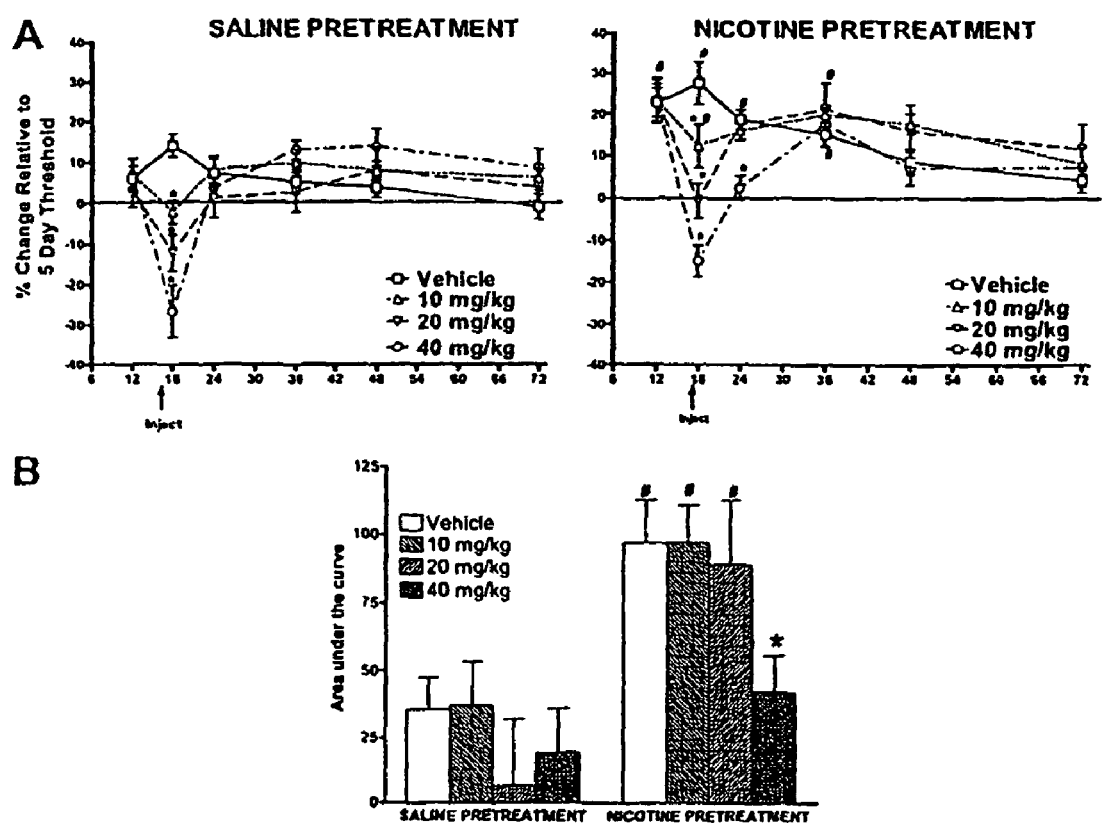
FIGS. 26A-26B illustrate the effects of the antidepressant bupropion on brain reward thresholds following withdrawal from chronic nicotine (3.16 mg/kg per day for 7 days) or saline administration.

Planned comparisons revealed that nicotine withdrawal resulted in a significant elevation in reward thresholds in saline-injected animals at all time points tested up to 36 h post-withdrawal. At the 48- and 72-h time points, the withdrawal-induced deficits had normalized. Thirty minutes following administration of bupropion (17.5 h post withdrawal) there was a significant and dose-dependent lowering of reward thresholds at all doses, regardless of whether the animals had been pretreated with nicotine or not. Furthermore, following injection of bupropion (40 mg/kg) there was no longer any significant difference between animals that had been pretreated with saline and those pretreated with nicotine. Moreover, in saline pretreated animals, this reduction in threshold was short-lived and completely reversed at the next time point tested (24 h) in all animals, which was similar to the results of experiment 1. Interestingly, however, animals pretreated with nicotine and injected with 40 mg/kg bupropion still exhibited a significant (P<0.001) reduction in reward thresholds compared to nicotine-pretreated animals that were injected with saline (see FIG. 26A).

Analysis of the area under the curve of the threshold data (over the entire 72-h withdrawal period) demonstrated a significant effect of nicotine pretreatment [F(1,68)=13.705, P<0.001]. There was no overall statistically significant effect of drug (bupropion) treatment, or a drug×pump interaction. Planned comparisons indicated that animals pretreated with nicotine had a higher area under the curve threshold level than corresponding animals pretreated with saline. This elevation was completely reversed in animals treated with the highest dose of bupropion (40 mg/kg) tested (see FIG. 26B). Raw mean 5-day baseline thresholds were in the range of 108.69-131.83 mA.

Figure 27:
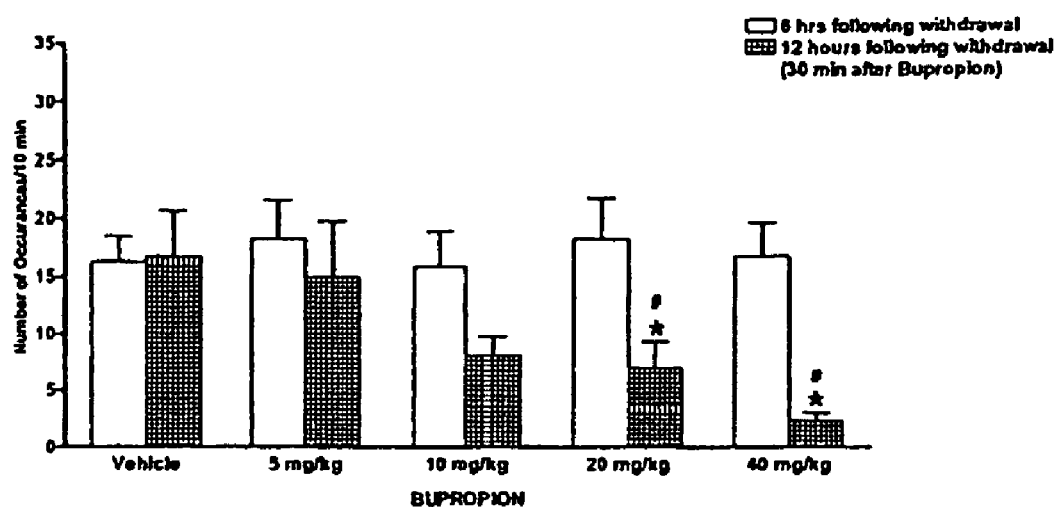
FIGS. 27A-B illustrate the effects of the antidepressant bupropion on somatic signs 12 h following withdrawal from chronic nicotine treatment (3.16 mg/kg per day for 6.75 days).
Figure 27:
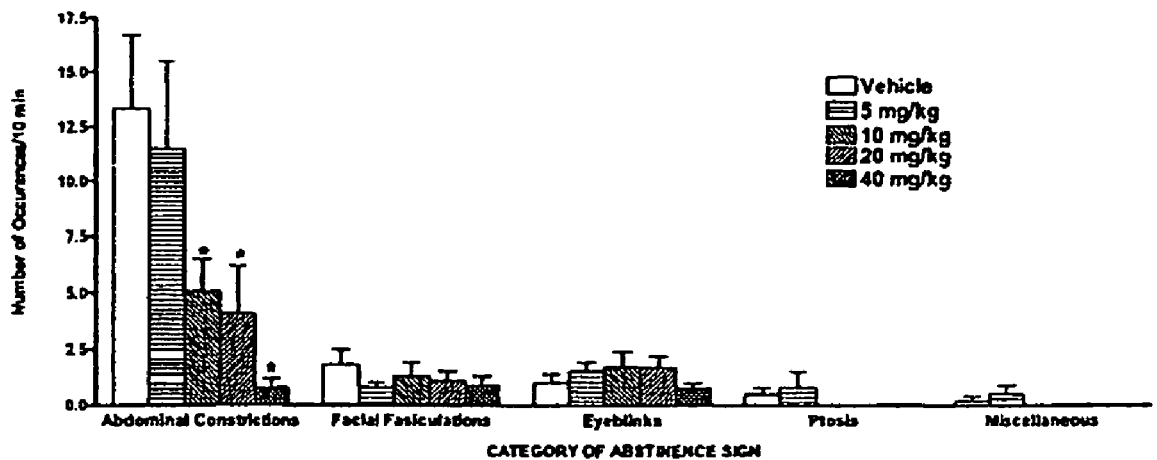

Experiment 4: Effects of Acute Bupropion Treatment on Somatic Signs Subsequent to Withdrawal from Chronic Nicotine Administration Six hours after removal of the nicotine-containing minipumps and prior to any drug manipulation, there was a significant increase in the amount of total somatic signs of abstinence. These signs were also evident to the same extent 12 h following withdrawal in nicotineexposed rats that were treated with vehicle before the 12-h observation time point. There was a significant interaction of bupropion treatment with time [F(4,31)=23.76 P<0.001]. Post hoc comparisons revealed that bupropion (20-40 mg/kg) administered 30 min prior to the 12-h withdrawal timepoint resulted in a reversal of the expression of total somatic signs compared to the number of somatic signs exhibited by the same animals at the 6-h time point before the bupropion administration (withinsubjects comparison) and those of vehicle-treated rats that also were undergoing nicotine withdrawal (betweensubjects comparison) (see FIG. 27A). Finally, it should be noted that there were no significant differences between the groups' total number of somatic signs before the administration of bupropion (6 h post-pump removal; see FIG. 27A) or several hours posttreatment (24 h post pump removal and 12.5 h postbupropion administration; P>0.05; vehicle=20.7±7.3; bupropion 5 mg/kg=18.6±4; bupropion 10 mg/kg=17.1±4.6; bupropion 20 mg/kg=14.1±2.2; bupropion 40 mg/kg=14.6±2.6). These data indicate that the difference between the saline and bupropion-treated rats (12 h postpump removal) is not due to baseline differences, and that acute treatment with bupropion has no long-term (12.5 h) effect on the expression of the somatic signs of nicotine withdrawal.

One-way ANOVAs were used to examine the effects of bupropion on the individual somatic signs at the 12-h withdrawal time point. It was demonstrated that there was a significant decrease in the amount of abdominal constrictions (writhes and gasps) with bupropion administration [F(4,31)= 4.037 P<0.01], but not on other signs. Planned comparison revealed that bupropion (10-40 mg/kg) reversed the withdrawal-induced increase in abdominal constrictions (see FIG. 27B).

Discussion

The present studies provide striking evidence that bupropion acts to alter brain reward circuits influenced by nicotine. First, bupropion increases brain reward function under baseline conditions. Second, at low doses it blocks the reward facilitating effects induced by acute nicotine. Third, it reverses both the negative affective aspects of nicotine withdrawal that are expressed as reward deficits and the somatic signs of withdrawal. The ability of bupropion to increase brain reward function under baseline conditions, as indicated by lowering of ICSS thresholds, is in stark contrast to data that we and others previously generated with other antidepressants using ICSS. Such studies showed that acute administration of antidepressants such as desipramine, paroxetine or fluoxetine had no effect or induced elevations in thresholds under baseline conditions (Atrens et al. 1977; Katz and Carroll 1977; Binks et al. 1979; Hall et al. 1990; Markou et al. 1992; Lee and Kornetsky 1998; Lin et al. 1999; Harrison et al. 2001a; 2001b; Cryan and Markou, unpublished observations). This differential effect of bupropion may underlie its superiority over many other antidepressants in smoking cessation. In contrast, Mc-Carter and Kokkinidis (1988) demonstrated that 28-day treatment with bupropion had no effect on the rate of responding for ICSS. It is difficult to draw comparisons between these two data sets, however, because the McCarter and Kokkinidis procedure is operationally different from ours and used only one bupropion dose (20 mg/kg). It has been suggested, given the high incidence of smoking among psychiatric populations including depressed patients (Leonard et al. 2001), that smokers may be using nicotine to self-medicate depressive symptomatology (Glassman et al. 1990; Markou et al. 1998; Markou and Kenny 2002). Indeed, these largely epidemiological observations have recently been confirmed neurochemically, where it was shown that locus coeruleus a2 noradrenergic receptors are down-regulated in smokers to a similar extent as previously reported with antidepressant medications (Klimeck et al. 2001). Furthermore, withdrawal from nicotine results in deficits in brain reward function similar to those observed in major affective disorders (Markou and Kenny 2002). Taken together, these observations suggest that antidepressant medications may be an effective treatment in decreasing smoking rates, because they treat the underlying depressive symptomatology. However, there is growing evidence that antidepressants, such as the selective serotonin reuptake inhibitors, may reduce nicotine intake only, if at all, in certain subsets of depressed patients and may have limited efficacy in non-depressed patients (Kotlyar et al. 2001). In contrast, bupropion is equally effective in healthy and psychiatric populations and therefore its efficacy extends beyond that of its antidepressant properties (Hayford et al. 1999). We suggest here that the antismoking efficacy of bupropion may be due to its additional effects on brain reward function even under baseline non-withdrawal conditions, effects not shared by other antidepressants.

The neurochemical mechanisms underlying bupropion's actions are still not well elucidated. Recent data indicate that bupropion's behavioural effects may be due to its effects on the noradrenergic system (Ascher et al. 1995; Cryan et al. 2001; Dong and Blier 2001). Nonetheless, unlike many antidepressants it also acts as a dopamine reuptake inhibitor (albeit in the micromolar range) (Ascher et al. 1995) and microdialysis studies have shown that acute administration of bupropion in the dose range that decreases brain reward thresholds in the current studies, increases extracellular dopamine (Nomikos et al. 1989; Li et al. 2002). Given that the dopamine system long has been associated with brain reward mechanisms, this property of bupropion may contribute to its rewardenhancing effects. Dopaminergic mechanisms also have been implicated in both the rewarding aspects of nicotine and in the manifestation of the nicotine withdrawal syndrome (Hildebrand et al., 1998, 1999; Kenny and Markou 2001; Ferrari et al. 2002; Mansvelder et al. 2002;

Picciotto and Corrigall 2002). However, recent studies have shown that whereas increases in nucleus accumbens dopamine concentrations are essential for ICSS responding to occur, they do not parallel the temporal dynamics of ICSS (Garris et al. 1999). Thus, whilst dopamine is involved in certain aspects of reward (most likely novelty or expectancy), other reciprocal neurochemical mechanisms are recruited to sustain the rewarding "hedonic" aspects of self-stimulation (Wise and Stein 1969; Herberg et al. 1976; Garris et al. 1999). Thus, by using ICSS at the level of the lateral hypothalamus we are able to obtain an index of trans-synaptic modulation of activity in limbic areas, such as the nucleus accumbens, an area strongly but not exclusively implicated in the mediation of reward, thus allowing the detection of non-dopaminergic neurotransmitter modulation. Such modulation is relevant to the current studies because bupropion has effects at both dopaminergic and noradrenergic transporters. Indeed, recent electrophysiological data suggest that sustained bupropion treatment (for 2 days by minipump) altered the firing of locus coereleus noradrenergic neurons and to a lesser extent serotonergic raphe neurons but not dopaminergic ventral tegmental area neurons (Dong and Blier 2001). Furthermore, a recent imaging study in humans demonstrated that at therapeutically effective doses bupropion has only 22% occupancy at the dopamine transporter (Meyer et al. 2002), indicating that the efficacy of bupropion is probably not solely dopamine-mediated.

Moreover, recent evidence suggests that bupropion may act as a functional antagonist at neuronal nicotinic acetylcholine receptors (Fryer and Lukas 2002; Slemmer et al. 2000; Miller et al. 2002). Our data showing blockade of the acute rewarding effects of nicotine by bupropion at a dose that was ineffective on its own supports this hypothesis. At higher doses bupropion's independent effects in facilitating brain reward function are manifested, making it difficult to disentangle its potential nicotinic antagonist effects. Nonetheless, our observations also give neurochemical credence to the clinical practice of initiating bupropion therapy prior to nicotine cessation (Hughes et al. 1999). It is likely that bupropion may act acutely to attenuate the rewarding effects of nicotine, thus increasing the likelihood of cessation. Indeed, mecamylamine, a classical nicotinic receptor antagonist, has been shown to be effective as a smoking cessation aid when used in combination with a nicotine patch (Rose et al. 1994). Interestingly, bupropion generalizes to nicotine in drug discrimination paradigms. However, unlike nicotine's discriminatory properties, those of bupropion are insensitive to blockade by mecamylamine, indicating a differential mechanism of action mediating the discriminatory cues of bupropion and nicotine (Young and Glennon 2002; Wiley et al. 2002).

The reversal of the affective aspects of withdrawal by all doses of bupropion tested here (10, 20 and 40 mg/kg) further suggests that its effects on reward systems are relevant to its therapeutic efficacy. Further, our data show clear differential effects of bupropion on reward thresholds in nicotine-pretreated animals compared with salinetreated controls. In the case of the latter, bupropion induced a short-lasting lowering of thresholds that returned to baseline at the next time point tested, which is consistent with the results of our initial dose-finding studies. Animals that had been pretreated with chronic nicotine, whilst showing minor reductions in thresholds during continuous nicotine exposure exhibited marked elevations in thresholds upon cessation of nicotine administration, as shown previously (Epping-Jordan et al. 1998). The highest dose of bupropion tested (40 mg/kg) exhibited a protracted reversal of these withdrawal deficits, with thresholds still significantly lower than those of vehicle-challenged animals previously treated with nicotine at the second post-injection testing period (6.5 hours post-bupropion). Furthermore, an analysis of reward thresholds over the entire 72-h period indicates that there was no difference in animals undergoing nicotine withdrawal and injected with bupropion (40 mg/kg) and those not undergoing withdrawal. Administration of lower bupropion doses (10 and 20 mg/kg) also reversed the reward deficits, although this effect was not as protracted as that seen after administration of 40 mg/kg bupropion. These findings indicate that bupropion induces reversal of a withdrawal deficit that is differential from its effects on reward function under baseline conditions. It is likely that this prolongation of the attenuation of withdrawal-induced reward deficits is of prime importance to the anti-smoking properties of bupropion, as the affective aspects of withdrawal are considered to be a critical factor in motivating further drug use (Kenny and Markou 2001). These data are in contrast to previous data with the antidepressants fluoxetine and paroxetine which did not much alter the negative affective aspects of withdrawal syndrome when given alone (Harrison et al 2001a, 2001 b). However, such deficits in reward function were counteracted when a selective serotonin reuptake inhibitor was given in combination with a serotonin1A autoreceptor antagonist (Harrison et al 2001a; 2001 b). These findings are consistent with recent data demonstrating a role for the serotonergic dorsal raphe nucleus in mediating some of the affective aspects of nicotine withdrawal (Cheeta et al. 2000). Further, Rasmussen and colleagues (1997; 2000) have shown that 5-HT1A receptor antagonists reversed the increases in the auditory startle reflex observed during nicotine withdrawal in rats.

In addition to counteracting the affective components of nicotine withdrawal, bupropion also reversed the expression of the somatic aspects of the spontaneous nicotine withdrawal syndrome. This observation is consistent with a preliminary study reporting that bupropion reversed somatic signs of nicotine withdrawal (Malin 2001). The mechanisms underlying this reversal are not clear. Because reduced dopaminergic signaling is thought to be a key factor in the manifestation of somatic signs of nicotine withdrawal (Hildebrand et al. 1999), it is probable that bupropion's direct effects on the dopamine system may counteract this deficit. However, bupropion's effects on other pathways such as the noradrenergic and serotonergic systems cannot be excluded, as they also have been implicated in mediating the expression of somatic signs (Kenny and Markou 2001; Malin 2001). The reversal of both the affective and the somatic aspects of nicotine withdrawal also may explicate the marked efficacy of bupropion in smoking cessation, as the negative aspects of withdrawal are postulated to contribute to the tobacco smoking habit (Glassman et al. 1990; Breslau et al. 1992; Laje et al. 2001). Indeed, recent clinical studies demonstrated that negative affect was a significant mediator of bupropion's effects on smoking cessation (Shiffman et al. 2000; Lerman et al. 2002).

It should be noted that as all of the effects of bupropion in the present studies were investigated following acute administration, it is not known yet whether such effects persist with chronic administration. The only previous study on bupropion's effects on brain reward function was with chronic administration under baseline conditions (McCarter and Kokkinidis 1988). This study demonstrated that 28-day treatment with bupropion had no effect on the rate of responding for ICSS. It is difficult to draw comparisons between these two data sets, however, because McCarter and Kokkinidis investigated the effects of bupropion only under baseline conditions and their procedure is operationally different from ours. The fact that only one bupropion dose (20 mg/kg) was used in their studies, and that no acute testing was carried out makes it more difficult to assess whether such negative effects are relevant to the present data. One of the major drawbacks of using brain reward thresholds and somatic signs of nicotine withdrawal in the rat as indices of similar effects in humans is that these aspects of withdrawal are relatively short-lasting, in the range of 2-3 days (Kenny and Markou 2001). Thus, this short duration makes investigating the effects of chronic administration of potential therapies more difficult. Nevertheless, this window of 2-3 days may be sufficient to allow the detection of potential therapeutic effects of novel treatments, similarly to models of other psychiatric disorders (e.g. Geyer et al. 2001; Lucki 2001; Cryan et al. 2002; Seong et al. 2002), and thus furnish the model with predictive validity (Geyer and Markou 1995). Further studies are warranted to clarify these issues and to assess the effects of chronic bupropion administration on the various aspects of nicotine withdrawal.

In conclusion, these data demonstrate that the utility of bupropion as an aid to smoking cessation may be due to its ability to alter the rewarding aspects of acute nicotine and to reverse the negative affective and somatic aspects of the nicotine withdrawal syndrome. The bupropioninduced increases in brain reward function even under non-nicotine withdrawal conditions also may contribute to a shift in the motivational priorities of smokers, and thus lead to decreases in tobacco consumption. Further studies will be needed to assess the effects of chronic bupropion treatment on brain reward and nicotine withdrawal.

REFERENCES CITED IN EXAMPLE 5

Ahluwalia J S, Harris K J, Catley D, Okuyemi K S, Mayo M S (2002) Sustained-release bupropion for smoking cessation in African Americans: a randomized controlled trial. JAMA 288:468-474

Anda R F, Williamson D F, Escobedo L G, Mast E E, Giovino G A, Remington P L (1990 Depression and the dynamics of smoking. A national perspective. JAMA 264:1541-1545

Ascher J A, Cole J O, Colin J N, Feighner J P, Ferris R M, Fibiger H C, Golden R N, Martin P, Potter W Z, Richelson E et al. (1995) Bupropion: a review of its mechanism of antidepressant activity. J Clin Psychiatry 56:395-401

Atrens D M, Ungerstedt U, Ljungberg T (1977) Specific inhibition of hypothalamic self-stimulation by selective reuptake blockade of either 5-hydroxytryptamine or noradrenaline. Psychopharmacology 52:177-80

Balfour D J (2001) The pharmacology underlying pharmacotherapy for tobacco dependence: a focus on bupropion. Int J Clin Pract 55:53-57 Barr A M, Markou A, Phillips A G (2002) A "crash" course on psychostimulant withdrawal as a model of depression. Trends Pharmacol Sci 23:475-482

Binks S M, Murchie J K, Greenwood D T (1979) A reward-reduction model of depression using self stimulating rats: an appraisal. Pharmacol Biochem Behav 10:441-443

Breslau N, Kilbey M, Andreski P (1992) Nicotine withdrawal symptoms and psychiatric disorders: findings from an epidemiological study of young adults. Am J Psychiatry 149: 464-469

Breslau N, Peterson E L, Schultz L R, Chilcoat H D, Andreski P (1998) Major depression and stages of smoking. A longitudinal investigation. Arch Gen Psychiatry 55:161-166

Cheeta S, Irvine E E, Kenny P J, File S E (2001) The dorsal raphe nucleus is a crucial structure mediating nicotine's anxiolytic effects and the development of tolerance and withdrawal responses. Psychopharmacology 155:78-85

Cryan J F, Dalvi A, Jin S H, Hirsch B R, Lucki I, Thomas S A (2001) Use of dopamine-beta-hydroxylase-deficient mice to determine the role of norepinephrine in the mechanism of action of antidepressant drugs. J Pharmacol Exp Ther 298:651-657

Cryan J F, Markou A, Lucki 1 (2002) Assessing antidepressant activity in rodents: recent developments and future needs. Trends Pharmacol Sci 23:238-45

Cryan J F, Hoyer D, Markou A (2003) Withdrawal from chronic amphetamine induces depression-like behavioural effects in rodents. Biol Psychiatry 23:238-245 Dong J, Blier P (2001) Modification of norepinephrine and serotonin, but not dopamine, neuron firing by sustained bupropion treatment. Psychopharmacology 155:52-57

Epping-Jordan M P, Watkins S S, Koob G F, Markou A (1998) Dramatic decreases in brain reward function during nicotine withdrawal. Nature 393:76-9

Ferrari R, Le Novere N, Picciotto M R, Changeux J P, Zoli M (2002) Acute and long-term changes in the mesolimbic dopamine pathway after systemic or local single nicotine injections. Eur J Neurosci 15:1810-1818

Fryer J D, Lukas R J (1999) Noncompetitive functional inhibition at diverse, human nicotinic acetylcholine receptor subtypes by bupropion, phencyclidine, and ibogaine. J Pharmacol Exp Ther 288:88-92 356

Garris P A, Kilpatrick M, Bunin M A, Michael D, Walker O D, Wightman R M (1999) Dissociation of dopamine release in the nucleus accumbens from intracranial self-stimulation. Nature 398:67-9

George T P, Vessicchio J C, Termine A, Bregartner T A, Feingold A, Rounsaville B J, Kosten T R (2002) A placebo controlled trial of bupropion for smoking cessation in schizophrenia. Biol Psychiatry 52:53-61

Geyer M A, Markou A (1995) Animal models of psychiatric disorders. In: Bloom R E, Kupfer D J (eds) Psychopharmacology: the fourth generation of progress. Raven Press, New York, pp 787-798

Geyer M A, Krebs-Thomson K, Braff D L, Swerdlow N R (2001) Pharmacological studies of prepulse inhibition models of sensorimotor gating deficits in schizophrenia: a decade in review. Psychopharmacology 156:117-154

Glassman A H, Heizer J E, Covey L S, Cottler L B, Stetner F, Tipp J E, Johnson J (1990) Smoking, smoking cessation, and major depression JAMA 264:1546-1549 Glover ED, Glover P N (2001) Pharmacologic treatments for the nicotine dependent smoker. Am J Health Behav 25:179-182

Hall F S, Stellar J R, Kelley A E (1990) Acute and chronic desipramine treatment effects on rewarding electrical stimulation of the lateral hypothalamus. Pharmacol Biochem Behav 37:277-281

Harrison A A, Liem Y T, Markou A (2001a) Fluoxetine combined with a serotonin-1A receptor antagonist reversed reward deficits observed during nicotine and amphetamine withdrawal in rats. Neuropsychopharmacology 25:55-71

Harrison A A, Chevrette J, Hoyer D, Markou A (2001 b) Paroxetine combined with a 5-HT1A receptor antagonist reversed amphetamine withdrawal-induced anhedonia in rats. Soc Neurosci Abstr Program Number 665.15

Harrison A A, Gasparini F, Markou A (2002) Nicotine potentiation of brain stimulation reward reversed by DHE and SCH 23390, but not by eticlopride, LY 314582 of MPEP in rats. Psychopharmacology 160:56-66

Hayford K E, Patten C A, Rummans T A, Schroeder D R, Offord K P, Croghan I T, Glover E D, Sachs D P, Hurt R D (1999) Efficacy of bupropion for smoking cessation in smokers with a former history of major depression or alcoholism. Br J Psychiatry 174:173-178

Hays J T, Hurt R D, Rigotti N A, Niaura R, Gonzales D, Durcan M J, Sachs D P, Wolter T D, Buist A S, Johnston J A, White J D (2001) Sustained-release bupropion for pharmacologic relapse prevention after smoking cessation. A randomized, controlled trial. Ann Int Med 135:423-433

Herberg L J, Stephens D N, Franklin K B (1976) Catecholamines and self-stimulation: evidence suggesting a reinforcing role for noradrenaline and a motivating role for dopamine. Pharmacol Biochem Behav 4:575-582

Hildebrand B E, Nomikos G G, Hertel P, Schilstrom B, Svensson T H (1998) Reduced dopamine output in the nucleus accumbens but not in the medial prefrontal cortex in rats displaying a mecamylamine-precipitated nicotine withdrawal syndrome. Brain Res 779:214-225

Hildebrand B E, Panagis G, Svensson T H, Nomikos, G G (1999) Behavioral and biochemical manifestations of mecamylamineprecipitated nicotine withdrawal in the rat: role of nicotinic receptors in the ventral tegmental area. Neuropsychopharmacology 21:560-574

Hughes J R, Gust S W, Skoog K, Keenan R M, Fenwick, J W (1991) Symptoms of tobacco withdrawal. A replication and extension. Arch Gen Psychiatry 48:52-59

Hughes J R, Goldstein M G, Hurt R D, Shiffman S (1999) Recent advances in the pharmacotherapy of smoking. JAMA 281:72-76

Hurt R D, Sachs D P, Glover E D, Offord K P, Johnston J A, Dale L C, Khayrallah M A, Schroeder D R, Glover P N, Sullivan C R et al (1997) A comparison of sustained-release bupropion and placebo for smoking cessation. N Engll J Med 337:1195-1202

Jorenby D E, Leischow S J, Nides M A, Rennard S J, Johnston J A, Hughes A R, Smith S S, Muramoto M L, Daughton D M, Doan K, Fiore M C, Baker T B (1999) A controlled trial of sustainedrelease bupropion, a nicotine patch, or both for smoking cessation. N Engl J Med 340:685-691 Katz R J, Carroll B J (1977)

Intracranial reward after Lilly 110140 (fluoxetine HCl): evidence for an inhibitory role for serotonin. Psychopharmacology 51:189-193 Kenny P J, Markou A (2001) Neurobiology of the nicotine withdrawal syndrome. Pharmacol Biochem Behav 70:531-549

Klimek V, Zhu M Y, Dilley G, Konick L, Overholser J C, Meltzer H Y, May W L, Stockmeier C A, Ordway G A (2001) Effects of long-term cigarette smoking on the human locus coeruleus. Arch Gen Psychiatry 58:821-827

Kornetsky C, Esposito R U (1979) Euphorigenic drugs: effects on the reward pathways of the brain. Fed Proc 38:2473-2476

Kotlyar M, Golding M, Hatsukami D K, Jamerson B D (2001) Effect of nonnicotine pharmacotherapy on smoking behavior. Pharmacotherapy 21:1530-1548

Laje R P, Berman J A, Glassman A H (2001) Depression and nicotine: preclinical and clinical evidence for common mechanisms. Curr Psychiatry Rep 3:470-476

Lee K, Kornetsky C (1998) Acute and chronic fluoxetine treatment decreases the sensitivity of rats to rewarding brain stimulation. Pharmacol Biochem Behav 60:539-544

Lerman C, Roth D, Kaufmann V, Audrain J, Hawk L, Liu A, Niaura R, Epstein L (2002) Mediating mechanisms of the impact of bupropion in smoking cessation treatment. Drug Alcohol Depend 67:219-223

Leith N J, Barrett R J (1976) Amphetamine and the reward system: evidence for tolerance and post-drug depression. Psychopharmacology 46:19-25

Leonard S, Adler L E, Benhammou K, Berger R, Breese C R, Drebing C, Gault J, Lee M J, Logel J, Olincy A, Ross R G, Stevens K, Sullivan B, Vianzon R, Virnich D E, Waldo M, Walton K, Freedman R (2001) Smoking and mental illness. Pharmacol Biochem Behav 70:561-570

Li S X, Perry K W, Wong D T (2002) Influence of fluoxetine on the ability of bupropion to modulate extracellular dopamine and norepinephrine concentrations in three mesocorticolimbic areas of rats. Neuropharmacology 42:181-190

Lin D, Koob G F, Markou A (1999) Differential effects of withdrawal from chronic amphetamine or fluoxetine administration on brain stimulation reward in the rat-interactions between the two drugs Psychopharmacology 145: 283-294

Lipkus I M, Barefoot J C, Williams R B, Siegler I C (1994) Personality measures as predictors of smoking initiation and cessation in the UNC Alumni Heart Study. Health Psychol 13:149-155

Lucki 1 (2001) A prescription to resist proscriptions for murine models of depression. Psychopharmacology 153: 395-398

Malin D H (2001) Nicotine dependence: studies with a laboratory model. Pharmacol Biochem Behav 70:551-559

Malin D H, Lake J R, Newlin-Maultsby P, Roberts L K, Lanier J G, Carter V A, Cunningham J S, Wilson O B (1992) Rodent model of nicotine abstinence syndrome. Pharmacol Biochem Behav 43:779-784

Mansvelder H D, Keath J R, McGehee D S (2002) Synaptic mechanisms underlie nicotine-induced excitability of brain reward areas. Neuron 33:905-919

Markou A, Kenny P J (2002) Neuroadaptations to chronic exposure to drug of abuse: Relevance to depressive symptomatology seen across psychiatric diagnostic categories. Neurotox Res 4:297-313

Markou A, Koob G F (1991) Postcocaine anhedonia. An animal model of cocaine withdrawal. Neuropsychopharmacology 4:17-26

Markou A, Koob G F (1992) Construct validity of a self-stimulation threshold paradigm: effects of reward and performance manipulations. Physiol Behav 51:111-119

Markou A, Hauger R L, Koob G F (1992) Desmethylimipramine attenuates cocaine withdrawal in rats Psychopharmacology 109:305-314 357

Markou A, Kosten T R, Koob G F (1998) Neurobiological similarities in depression and drug dependence: a self-medication hypothesis. Neuropsychopharmacology 18:135-174

McCarter B D, Kokkinidis L (1988) The effects of long-term administration of antidepressant drugs on intracranial self-stimulation responding in rats. Pharmacol Biochem Behav 31:243-247

Meyer J H, Goulding V S, Wilson A A, Hussey D, Christensen, B K, Houle S (2002) Bupropion occupancy of the dopamine transporter is low during clinical treatment. Psychopharmacology 163:102-105

Miller D K, Sumithran S P, Dwoskin L P (2002) Bupropion inhibits nicotine-evoked [(3)H]overflow from rat striatal slices preloaded with [(3)H]dopamine and from rat hippocampal slices preloaded with [(3)H]norepinephrine. J Pharmacol Exp Ther 302:1113-1122

Nomikos G G, Damsma G, Wenkstern D, Fibiger H C (1989) Acute effects of bupropion on extracellular dopamine concentrations in rat striatum and nucleus accumbens studied by in vivo microdialysis. Neuropsychopharmacology 2:273-279

Peto R, Lopez A D, Boreham J, Thun M, Heath C Jr (1992) Mortality from tobacco in developed countries: indirect estimation from national vital statistics. Lancet 339:1268-1278

Picciotto M R, Corrigall W A (2002) Neuronal systems underlying behaviors related to nicotine addiction: neural circuits and molecular genetics. J Neurosci 22:3338-3341

Rasmussen K, Kallman M J, Helton D R (1997) Serotonin-1A antagonists attenuate the effects of nicotine withdrawal on the auditory startle response. Synapse 27:145-152

Rasmussen K, Calligaro D O, Czachura J F, Dreshfield-Ahmad L J, Evans D C, Hemrick-Luecke S K, Kallman M J, Kendrick W T, Leander J D, Nelson D L, Overshiner C D, Wainscott D B, Wolff M C, Wong D T, Branchek T A, Zgombick J M, Xu Y C (2000) The novel 5-hydroxytryptamine(1A) antagonist LY426965: effects on nicotine withdrawal and interactions with fluoxetine. J Pharmacol Exp Ther 294:688-700

Rose J E, Behm F M, Westman E C, Levin E D, Stein R M, Ripka G V (1994) Mecamylamine combined with nicotine skin patch facilitates smoking cessation beyond nicotine patch treatment alone. Clin Pharmacol Ther 56:86-99

Semenova S, Markou A (2003) Clozapine treatment attenuated somatic and affective signs of nicotine and amphetamine withdrawal in subsets of rats that exhibited hyposensitivity to the initial effects of clozapine. Biol Psychiatry (in press)

Seong E, Seasholtz A F, Burmeister M (2002) Mouse models for psychiatric disorders. Trends Genet 18:643-650 Shiffman S, Johnston J A, Khayrallah M, Elash C A, Gwaltney C J, Paty J A, Gnys M, Evoniuk G, DeVeaugh-Geiss J (2000) The effect of bupropion on nicotine craving and withdrawal. Psychopharmacology 148:33-40

Skjei K L, Markou A (2003) Effects of repeated withdrawal episodes, nicotine dose, and duration of nicotine exposure on the severity and duration of nicotine withdrawal in rats. Psychopharmacology (DOI 10.1007/s00213-003-1414-1)

Slemmer J E, Martin B R, Damaj M I (2000) Bupropion is a nicotinic antagonist. J Pharmacol Exp Ther 295:321-327 Spielewoy C, Markou A (2002) Withdrawal from chronic phencylidine treatment induces long-lasting depression in brain reward function Neuropsychopharmacology (in press)

Stolerman I P, Jarvis M J (1995) The scientific case that nicotine is addictive. Psychopharmacology 117:2-10

Tashkin D, Kanner R, Bailey W, Buist S, Anderson P, Nides M, Gonzales D, Dozier G, Patel M K, Jamerson B. (2001) Smoking cessation in patients with chronic obstructive pulmonary disease: a double-blind, placebo-controlled, randomised trial. Lancet 357:1571-1575

Watkins S S, Stinus L, Koob G F, Markou A (2000) Reward and somatic changes during precipitated nicotine withdrawal in rats: centrally and peripherally mediated effects. J Pharmacol Exp Ther 292:1053-1064

Wiley J L, Lavecchia K L, Martin B R, Damaj M I (2002) Nicotinelike discriminative stimulus effects of bupropion in rats. Exp Clin Psychopharmacol 10:129-135

Wise C D, Stein L (1969) Facilitation of brain self-stimulation by central administration of norepinephrine. Science 163:299-301 Young R, Glennon R A (2002) Nicotine and bupropion share a similar discriminative stimulus effect. Eur J Pharmacol 443:113-118

While the invention has been described in detail with reference to certain preferred embodiments thereof, it will be understood that modifications and variations are within the spirit and scope of that which is described and claimed.

What is claimed is:

1. A method for treating drug dependence in a subject, comprising administering to a subject with drug dependence an effective amount of (a) a first antagonist which modulates metabotropic glutamate receptor 2 and/or metabotropic glutamate receptor 3, and (b) a second antagonist which modulates metabotropic glutamate receptor 5, thereby treating the disorder; wherein the drug dependence is selected from the group consisting of nicotine addiction, alcohol addiction, opiate addiction, amphetamine addiction, cocaine addiction, and methamphetamine addiction.

2. A method for treating drug dependence in a subject, comprising administering to a subject with drug dependence an effective amount of (a) a first antagonist which modulates metabotropic glutamate receptor 2, and (b) a second antagonist which modulates metabotropic glutamate receptor 5, thereby treating the disorder; wherein the drug dependence is selected from the group consisting of nicotine addiction, alcohol addiction, opiate addiction, amphetamine addiction, cocaine addiction, and methamphetamine addiction.

3. A method for treating drug dependence in a subject, comprising administering to a subject with drug dependence an effective amount (a) a first antagonist which modulates metabotropic glutamate receptor 3 and (b) a second antagonist which modulates metabotropic glutamate receptor 5, thereby treating the disorder; wherein the drug dependence is selected from the group consisting of nicotine addiction, alcohol addiction, opiate addiction, amphetamine addiction, cocaine addiction, and methamphetamine addiction.

4. The method of claim 1, wherein the drug dependence is nicotine addiction.

5. The method of claim 1, wherein the drug dependence is cocaine addiction.

6. The method according to claim 1, wherein the antagonist which modulates metabotropic glutamate receptor 5 is 2-methyl-6-(phenylethynyl)-pyridine, and the antagonist which modulates metabotropic glutamate receptor 2 and/or metabotropic glutamate receptor 3 is 2S-2-amino-2-(1S,2S-2-carboxycyclopropan-1-yl)-3-(xanth-9-yl)propionic acid.

7. A method of treating a warm-blooded animal having an addictive disorder comprising administering to the animal a combination comprising (a) at least a first active ingredient selected from a metabotropic glutamate receptor 2 antagonist and a metabotropic glutamate receptor 3 antagonist, and (b) at least a second active ingredient being a metabotropic glutamate receptor 5 antagonist, in which the active ingredients are present in each case in free form or in the form of their pharmaceutically acceptable salts, and optionally at least one pharmaceutically acceptable carrier, wherein the active ingredients are in a quantity which is jointly therapeutically effective against an addictive disorder; wherein the addictive disorder is selected from the group consisting of nicotine addiction, alcohol addiction, opiate addiction, amphetamine addiction, cocaine addiction, and methamphetamine addiction.

8. A method for treating an addictive disorder, comprising: a) administering to a subject in need thereof, an effective amount of a first antagonist that modulates mGluR5 during a first time period, wherein the first time period is a time period wherein the subject expects to be in an environment wherein, or exposed to stimuli in the presence of which, the subject habitually uses an addictive substance; and b) administering a second antagonist that modulates mGluR2 and/or 3 during a second time period, wherein the second time period is a time period wherein the subject is suffering from withdrawal; wherein the addictive disorder is selected from the group consisting of nicotine addiction, alcohol addiction, opiate addiction, amphetamine addiction, cocaine addiction, and methamphetamine addiction.

9. The method of claim 8, wherein the antagonist that modulates mGluR5 is 2-methyl-6-(phenylethynyl)-pyridine and the antagonist that modulates mGluR2 and/or 3 is 2S-2-amino-2-(1S,2S-2-carboxycyclopropan-1-yl)-3-(xanth-9-yl) propionic acid.

10. The method of claim 1, wherein the first antagonist and the second antagonist are administered to the subject sequentially or simultaneously.

* * * * *